United States Patent
Chen et al.

(10) Patent No.: US 12,163,132 B2
(45) Date of Patent: Dec. 10, 2024

(54) GAPMER ANTISENSE OLIGONUCLEOTIDES TARGETING SARS-CoV-2 FOR TREATING COVID 19

(71) Applicant: CHILDREN'S NATIONAL MEDICAL CENTER, Washington, DC (US)

(72) Inventors: Yi-Wen Chen, Bethesda, MD (US); Alexander E. Liu, St. Louis, MO (US)

(73) Assignee: CHILDREN'S NATIONAL MEDICAL CENTER, Washington, DC (US)

(*) Notice: Subject to any disclaimer, the term of this patent is extended or adjusted under 35 U.S.C. 154(b) by 0 days.

(21) Appl. No.: 17/471,719

(22) Filed: Sep. 10, 2021

(65) Prior Publication Data

US 2022/0090082 A1 Mar. 24, 2022

Related U.S. Application Data

(60) Provisional application No. 63/077,250, filed on Sep. 11, 2020.

(51) Int. Cl.
*C12N 15/11* (2006.01)
*A61P 31/14* (2006.01)
*C12N 15/113* (2010.01)

(52) U.S. Cl.
CPC .......... *C12N 15/1131* (2013.01); *A61P 31/14* (2018.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3233* (2013.01); *C12N 2310/341* (2013.01)

(58) Field of Classification Search
None
See application file for complete search history.

(56) References Cited

U.S. PATENT DOCUMENTS

2005/0100885 A1* 5/2005 Crooke .............. C12N 15/1137
435/5

* cited by examiner

*Primary Examiner* — Ekaterina Poliakova-Georgantas
(74) *Attorney, Agent, or Firm* — Oblon, McClelland, Maier & Neustadt, L.L.P.

(57) ABSTRACT

SARS-CoV-2 causes pandemic COVID19. Developing an effective treatment to directly target the virus could significantly impact viral burden in those most vulnerable to the devastating effects of this virus. The invention provides antisense oligonucleotides (AOs) to target the single stranded RNA genome of the SARS-CoV-2 viruses. The administration of AOs can significantly reduce the target viral RNAs.

15 Claims, 6 Drawing Sheets
Specification includes a Sequence Listing.

GAPMER ANTISENSE OLIGONUCLEOTIDES TARGETING SARS-CoV-2 FOR TREATING COVID 19

CROSS-REFERENCE TO RELATED APPLICATION

The application claims priority to U.S. Provisional Application No. 63/077,250 filed on Sep. 11, 2020, which is incorporated by reference in its entirety.

REFERENCE TO A SEQUENCE LISTING

In accordance with 37 CFR § 1.52(e)(5), the present specification makes reference to a Sequence Listing (submitted electronically as a .txt file named "539103US_ST25.txt". The .txt file was generated on Sep. 10, 2021, and is 44,030 bytes in size. The entire contents of the Sequence Listing are herein incorporated by reference.

BACKGROUND OF THE INVENTION

Field of the Invention. The disclosure relates to antisense oligonucleotides ("AOs") and AO cocktails targeting SARS-CoV-2 RNA or different locations on target RNA and to methods for using AOs to degrade SARS-CoV-2 RNA, inhibit SARS-CoV-2 replication and to treatment of SARS-CoV-2.

Description of Related Art. Severe acute respiratory syndrome coronavirus 2 (SARS-CoV-2) is responsible for a global pandemic. Like other coronaviruses, SARS-CoV-2 has a single-stranded RNA genome. The genome is approximately 30 kb, non-segmented, and is positive-sense RNA. The RNA genome has a 5' cap structure and a 3' poly-A tail, which allows the viral RNA genome to be translated like an mRNA once it enters the host cell. The viral genome encodes non-structural proteins for the viral replication machinery, accessory proteins, and structural proteins, including spike (S), envelope (E), membrane (M), and nucleocapsid (N) proteins. In addition to coding sequences, the genome contains various cis-acting RNA elements in the 5' and 3' untranslated region (UTRs), which regulate viral replication, RNA synthesis, and viral packaging. SARS-CoV-2 enters the cells via interactions between the spike-glycoprotein on the surface of the virus and a host cellular receptor, angiotensin converting enzyme 2 (ACE2), which expresses in the respiratory tract. In addition, ACE2 is expressed at relatively higher levels in kidney, heart and intestine based on gene expression data of tissues from the GTEx RNA-seq study and other studies. Indeed, the tissues that express ACE2 at higher level were also reported to be affected by the SARS-CoV-2.

Signs and symptoms of COVID-19, caused by SARS-CoV-2, include fever or cough, and signs such as oxygen saturation or lung auscultation, findings which can be used to either rule out COVID-19 disease or select patients for further diagnostic testing. Signs and symptoms are also incorporated by reference to *Signs and symptoms to determine if a patient presenting in primary care or hospital outpatient settings has COVID-19 disease* COCHRANE DATABASE SYST REV. 2020 July; 2020(7): CD013665. Diagnostic tests include PCR and serological tests such as ELISA. Human coronaviruses (HCoVs) are often known as the viruses causing common cold. Healthy individuals infected with HCoVs often are non-symptomatic or show mild symptoms. However, HCoVs can cause more severe diseases in younger children, older individuals and individuals with certain health issues, such as being immunocompromised or asthmatic. COVID19 was first reported in December 2019, which was caused by SARS-CoV-2. While the main symptoms are associated with pneumonia and respiratory symptoms; the other organs, including heart, kidney and digestive system, have been reported to be affected. In addition, it was reported to be associated with multisystem inflammatory syndrome in children. Subjects with COVID-19 may have pneumonia or cytokine storm or may be asymptomatic carriers.

Proposed treatments include administration of remdesivir, azithromycin, hydroxychloroquine, chloroquine, or agents such as zinc, zinc ionophores, vitamins A, B complex, C, D and E, passive immunization with serum from a person who has recovered from infection (convalescent plasma), and protein or DNA-based vaccines.

Various AO-based therapies for viral disease have been proposed. For example, an AO treatment for influenza was developed and reported to be safe in a phase I clinical trial. However, no effective AO therapy has been developed for SARS-CoV or SARS-CoV-2 infections; Beigel, J. H., et al., *Safety, tolerability, and pharmacokinetics of radavirsen (AVI-7100), an antisense oligonucleotide targeting influenza a M1/M2 translation*, BR J CLIN PHARMACOL. 2018. 84, 25-34. However, prior attempts to develop morpholino-based AOs for the SARS-CoV have been limited by the chemistry and design. Moreover, morpholino-based AOs act via a steric blocking mechanism instead of RNA degradation; Neuman, B. W., et al., *Inhibition, escape, and attenuated growth of severe acute respiratory syndrome coronavirus treated with antisense morpholino oligomers*, J. VIROL. 2005. 79, 9665-76; Neuman, B. W., et al., *Antisense morpholino-oligomers directed against the 5' end of the genome inhibit coronavirus proliferation and growth*, J. VIROL. 1004, 78, 5891-9.

SUMMARY OF THE INVENTION

The present invention provides gapmer AOs that can effectively target SARS-CoV-2 RNA and efficiently degrade its RNA using a combination of in silico and bioinformatic analysis and in vitro testing, with the objective of providing antisense therapy for treating coronavirus disease 2019 (COVID-19) using gapmer antisense oligonucleotides (AOs).

One aspect of the invention is directed to gapmers that bind to SARS-CoV-2 RNA and degrade it. These gapmers include those targeting SEQ ID NOs: 1-293. They are preferably based on gapmers comprising nucleotides comprising domains of locked nucleic acids (LNA), 2'-O-methyl (2'-O-Me), or 2'-O-methoxyethyl (2'-MOE). Additional modifications to AOs may be made, for example, to increase potency, biological half-life, safety or reduce toxicity. Other AO chemistries besides those of LNA, 2'-O-Me, and 2'-MOE may be used. Another aspect of this invention is directed to a method for preventing or treating infection by SARS-CoV-2 by administering these gapmers, for example, into the respiratory system.

Embodiments of the invention include, but are not limited to the following.

1. A composition comprising a nucleotide sequence comprising: (i) an RNA-binding domain from about 5, 10, 15, 20, 25 to about 30 nucleotides complementary to a region of a SARS-CoV-2 RNA and (ii) at least one locked nucleic acid (LNA) domain comprising from about 1, 2, 3, 4, 5, 6, 7, 8, 9 to about 10 nucleotides; at least one 2'-O-methoxyethyl (2'-MOE) domain comprising from about 1, 2, 3, 4, 5, 6, 7, 8, 9 to about 10 nucleotides; and/or at least one 2'-O-methyl (2'-O-Me) domain comprising from about 1, 2, 3, 4, 5, 6, 7, 8, 9 to about 10 nucleotides, or a salt thereof. In some embodiments, a target sequence for a gapmer may be in an RNA encoding S, E, M or N proteins or in any of the ORFs of SARS-CoV-2 such as those shown in FIG. 2. A gapmer may also target a non-coding region such as cis-acting RNA elements in the 5' and 3' untranslated region (UTRs), which regulate viral replication, RNA synthesis, and viral packaging. In some preferred embodiments, gapmers comprise or consist of 16, 17, 18, 19 to 20 bases.

2. The composition of embodiment 1, wherein the RNA binding domain comprises 1 or 2 nucleotide mismatches with the complementary region of a SARS-CoV-2 RNA.

3. The composition of embodiment 1, wherein the nucleotide sequence is complementary to a segment of SARS-CoV-2 RNA encoding the S protein. Usually, the AO sequences described herein are selected for potency using bioinformatic algorithms and target different regions of the virus.

4. The composition of embodiment 1 that comprises a nucleotide sequence of about 8, 10, 20, 50, 100 to 120 nucleotides complementary to a genome of SARS-CoV-2, wherein the nucleotide sequence is complementary to at least 8, 9, 10, 11, 12, 13, 14, or 15 contiguous nucleotides encoding the S protein.

5. The composition of embodiment 1, wherein the nucleotide sequence is complementary to a segment of SARS-CoV-2 RNA encoding the E protein.

6. The composition of embodiment 1 that comprises a nucleotide sequence of about 8, 10, 20, 50, 100 to 120 nucleotides complementary to a genome of SARS-CoV-2, wherein the nucleotide sequence is complementary to at least 8, 9, 10, 11, 12, 13, 14, or 15 contiguous nucleotides encoding the E protein.

7. The composition of embodiment 1, wherein the nucleotide sequence is complementary to a segment of SARS-CoV-2 RNA encoding the M protein.

8. The composition of embodiment 1 that comprises a nucleotide sequence of about 8, 10, 20, 50, 100 to 120 nucleotides complementary to a genome of SARS-CoV-2, wherein the nucleotide sequence is complementary to at least 8, 9, 10, 11, 12, 13, 14, or 15 contiguous nucleotides encoding the M protein.

9. The composition of embodiment 1, wherein the nucleotide sequence is complementary to a segment of SARS-CoV-2 RNA encoding the N protein.

10. The composition of embodiment 1 that comprises a nucleotide sequence of about 8, 10, 20, 50, 100 to 120 nucleotides complementary to a genome of SARS-CoV-2, wherein the nucleotide sequence is complementary to at least 8, 9, 10, 11, 12, 13, 14, or 15 contiguous nucleotides encoding the N protein.

11. The composition of embodiment 1 that comprises at least one sequence which is complementary to any of SEQ ID NOS: 1-293.

12. The composition of embodiment 1 that comprises at least two sequences which are complementary to any of SEQ ID NOS: 1-293 which bind to RNA encoding different SARS-CoV-2 antigens or regulatory sequences.

13. The composition of any of embodiments 1 through 12, wherein the nucleotide sequence comprises one or a plurality of locked nucleic acid (LNA) domains, one or a plurality of 2'-O-methoxyethyl (2'-MOE) domains, or one or a plurality of 2'-O-methyl (2'-O-Me) domains.

14. The composition of any of embodiments 1 through 12, wherein the nucleotide sequence comprises two locked nucleic acid (LNA) domains, two 2'-O-methoxyethyl (2'-MOE) domains, or two 2'-O-methyl (2'-O-Me) domains.

15. The composition of any of embodiments 1 through 12, wherein each LNA domain, 2'-O-methoxyethyl (2'-MOE) domain, or 2'-O-methyl (2'-O-Me) domain individually comprises from about 1 to about 5 nucleotides.

16. The composition of any of embodiments 1 through 12, wherein the nucleotide sequence comprises one or a plurality of DNA gap domains.

17. The composition of embodiment 12, wherein the DNA gap domain comprises from about 6 to about 11 nucleotides.

18. The composition of any of embodiments 1 through 12, wherein the nucleotide sequence comprises a central DNA gap domain flanked by a first LNA domain, 2'-O-methoxyethyl (2'-MOE) domain, or 2'-O-methyl (2'-O-Me) domain at a 5' end of the nucleotide sequence and a second LNA domain, 2'-O-methoxyethyl (2'-MOE) domain, or 2'-O-methyl (2'-O-Me) domain on a 3' end of the nucleotide sequence.

19. The composition of any of embodiments 1 through 18, wherein the nucleotide sequence further comprises from about 1% to about 99% modified nucleotides chosen from: 2'-O-methyl (2'-O-Me) modification, a 2'O methylphosphorothioate (2'OMePS) modification, a phosphorodiamidate morpholino (PMO) modification, a 2'methoxyethoxy (2'-MOE) modification, a vivo-morpholino (vPMO) modification, a peptide conjugate, a peptide nucleic acid (PNA), or LNA.

20. The composition of any of embodiment 18, wherein the nucleotide sequence comprises a peptide conjugate.

21. A pharmaceutical composition comprising: (i) a therapeutically effective amount of any composition of embodiments 1-20; and (ii) a pharmaceutically acceptable carrier.

22. The pharmaceutical composition of embodiment 21, wherein the therapeutically effective amount ranges from about 0.01 µg/ml to about 100 mg/ml.

23. The pharmaceutical composition of embodiment 21 or 22, wherein the pharmaceutically acceptable carrier is distilled water or saline.

24. The pharmaceutical composition of any of embodiments 21 through 23, further comprising a particle that encapsulates the nucleotide sequence.

25. A method for degrading coronavirus RNA or inhibiting replication of coronavirus comprising contacting coronavirus RNA with the compositions or pharmaceutical compositions of any one of embodiments 1-24, optionally, after addition of RNAse H.

26. The method of embodiment 25 that comprises treating a subject at risk of being infected with SARS-CoV-2.

27. The method of embodiment 25 that comprises treating a subject who has been infected with SARS-CoV-2.

28. The method of embodiment 25 that comprises treating a subject having one or more signs or symptoms of COVID-19.

29. The method of any one of embodiments 25-28 that comprises administering the composition or pharmaceutical composition intravenously, intramuscularly, topically, intradermally, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, transmucosally, or transdermally.

30. The method of any one of embodiments 25-29 that comprises administering the composition or pharmaceutical composition intranasally or into the upper or lower respiratory system.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

DETAILED DESCRIPTION OF THE INVENTION

Figure 1A:
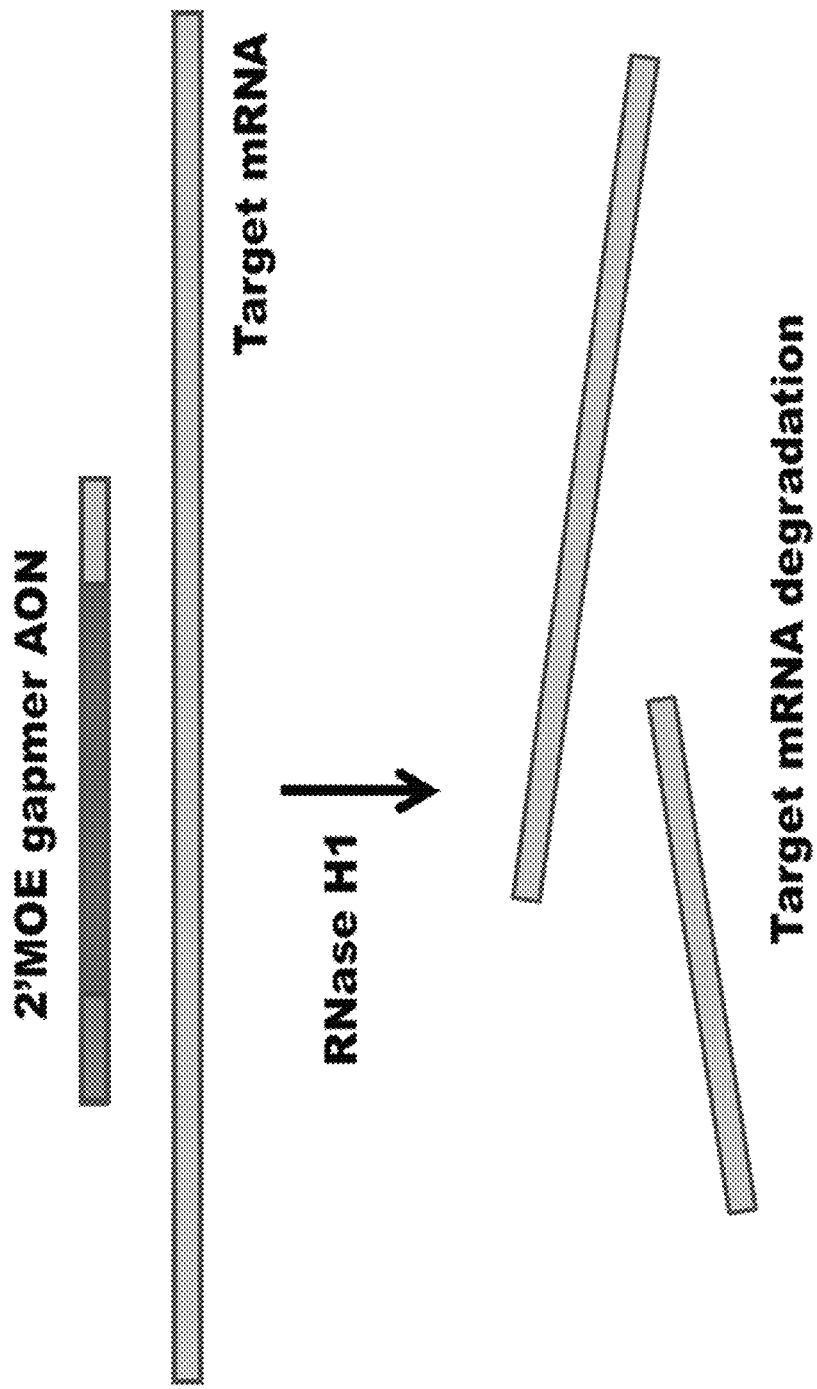
FIG. 1A shows the mechanism of 2'-MOE gapmer AOs silencing via RNase H1-mediated degradation. 2'-MOE gapmers are composed of a central DNA gap (center) and flanked by 2'-MOE monomers at the 5' and 3'-ends (ends). The central DNA gap is targeted by RNase H1 activity. The 2'-MOE flanks increase target binding affinity to the mRNA sequence and stability.
Figure 1B:
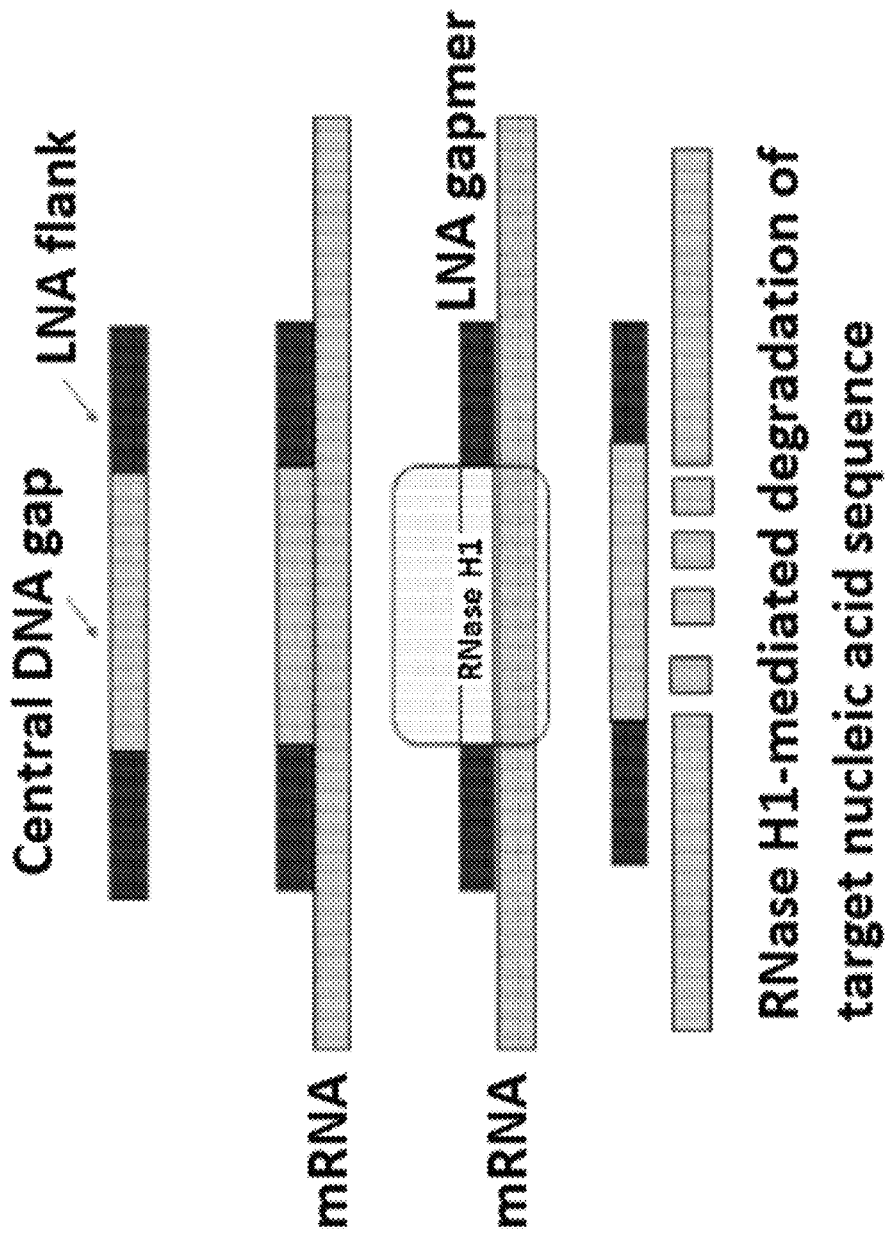
FIG. 1B shows the mechanism of antisense silencing via RNase H1-mediated degradation. RNase H1-mediated degradation of target mRNA can occur via LNA gapmers. LNA gapmers are composed of a central DNA gap and flanked by LNA monomers at the 5' and 3'-ends. The central DNA gap works through RNase H1 activity, whereas the LNA flanks are used to target binding affinity to the mRNA sequence.

AO gapmers or cocktails of AOs can be used to knock down target RNAs. Gapmers having different sequences generally exhibit different properties in binding to target RNAs for knocking down the RNA expression. The present application discloses design methods and chemical types of gapmers to provide safe and effective gapmers for SARS-CoV-2 knock down. The present application provides an AO strategy using a short single-stranded synthetic DNA molecule to selectively hybridize to their RNA targets via Watson-Crick base pairing. Oligonucleotides can be chemically-modified and are usually between 8 and 30 nucleotides in length. Once an AO binds to its target mRNA sequence, the AO can modulate gene expression via exon skipping, splice modulation or through degradation of the target RNA. The present application provides a design that the DNA/RNA duplex formed is subject to the RNase H digestion and the targeted gene transcripts are cleaved then degraded as shown in FIG. 1. The first FDA approved AO drug was an antiviral drug, Fomivirsen, which is a synthetic 21 nucleotide AO targeting cytomegalovirus (CMV) for treating CMV retinitis. The genome of SARS-CoV-2 is a positive-strand RNA which can be targeted by AOs directly. In addition to the viral genome RNA, mRNA transcripts that contain the target sequences will also be targeted for degradation by the AOs disclosed herein.

The present application provides two hundred and ninety-three different target sequences in the SARS-CoV-2 genome for targeting by antisense oligonucleotides based on in silico analysis and prioritized for analysis for AOs which act via the RNase H1-dependent RNA degradation mechanism which targets the SARS-CoV-2 viral genome and its transcript mRNAs for degradation. AO sequence selection was based on selection of conserved sequences among different strains of SARS-CoV-2. Furthermore, AOs were identified for binding to multiple stains or mutated forms of the virus which may have one or two mismatches in a target sequence compared to a reference strain. It was found that an AO with a few mismatches to a target sequence did not completely eliminate its binding to a target or eliminate its knock-down of viral RNA. This is advantageous as it could increase the scope of protection when viral variants have point mutations and are not fully complementary to a particular AO.

Gapmer AOs that were 16-20 nucleotides long were designed targeting SARS-CoV-2 sequences. The gapmer designs that showed highest in vitro and in vivo efficacies were gapmers with either locked nucleic acid (LNA) or 2'-O-methoxyethyl (2'-MOE) modified nucleotides at the 3' and 5' ends. Both the LNA and 2'-MOE are widely used chemistries for designing AOs and has been used in FDA approved drugs; see Lee, J. J. & Yokota, T., *Antisense therapy in neurology*, JOURNAL OF PERSONALIZED MEDICINE. 2013. 3, 144-76; Scoles, D. R. & Pulst, S. M., *Oligonucleotide therapeutics in neurodegenerative diseases*, RNA BIOLOGY, 2018. 1-8. Shen, X. & Corey, D. R., *Chemistry, mechanism and clinical status of antisense oligonucleotides and duplex RNAs*, Nucleic acids research. 2018. 46, 1584-1600; and Raal, F. J., et al., *Mipomersen, an apolipoprotein B synthesis inhibitor, for lowering of LDL cholesterol concentrations in patients with homozygous familial hypercholesterolaemia: a randomised, double-blind, placebo-controlled trial*, LANCET. 2010. 375, 998-1006. All of the above references are incorporated by reference. Nucleotides with chemical modifications in addition to the LNA and 2'-MOE have been used to improve stability and efficacy of the AOs, including a 2'-O-methyl (2'-O-Me) modification, 2'O-methylphosphorothioate (2'O-MePS) modification, a phosphorodiamidate morpholino (PMO) modification, a vivo-morpholino (vPMO) modification, a peptide conjugate, a peptide nucleic acid (PNA), and a 2'-Fluoro (2'-F) modification.

While the LNA modification provides higher affinity, liver toxicity was reported associated with AOs modified with LNA. In some treatments, the 2'-MOE chemistry has better safety record, such as a FDA approved drug, nusinersen, for treating spinal muscular atrophy (SMA). Advantageously, it was found that 2'-MOE gapmers were highly effective and safe in in vitro studies for SARS-CoV-2.

Since the SARS-CoV-2 infects the respiratory system and can affect additional organs, gapmer AOs can be safely delivered via either tracheal or systemic routes. Additional advantages include that the AOs enter cells via gymnosis therefore conjugation or other delivery system is not required. In addition to regular systemic delivery, the respiratory track provides an ideal path for delivery using nebulizing technology.

Conditions mimicking both systemic and aerosol delivery of the AOs using a 3D tissue system (MucilAir™) are assessed after the initial screening providing information regarding delivery, efficacy and safety. The MucilAir™ 3D tissue model has been used successfully for studying tissue responses to viral infections and toxicological testing and the company, Epithelix SaRL, which generated the 3D tissue model, also conducts in vitro studies for viral disease such as influenza and SARS-CoV-2, in their BL3 facility. This model is used to test t prioritized AOs based on initial screening to determine efficacy and toxicity of the AOs; Boda, B., et al., *Antiviral drug screening by assessing epithelial functions and innate immune responses in human 3D airway epithelium model*, ANTIVIRAL RES. 2018, 156, 72-79; Balogh et al., A 3D *Human Airway Model Enables Prediction of Respiratory Toxicity of Inhaled Drugs In Vitro*, TOXICOL SCI. 2018, 162, 301-308. Baxter, A., et al., *Targeted omics analyses, and metabolic enzyme activity assays demonstrate maintenance of key mucociliary characteristics in long term cultures of reconstituted human airway epithelia*, TOXICOL IN VITRO. 2015. 29, 864-75.

Example 1

Designing Gapmer AOs Targeting SARS-CoV-2 RNA

The genomes of several SARS-CoV-2 have been sequenced. Based on this genomic sequence information, AO targeting sequences having lengths up to 20 nucleotides were identified and prioritized. To implement screening of the AOs, new sets of screening criteria were developed including determining whether a target sequence for AOs was conserved among coronavirus or SARS-CoV-2 genomic sequences, evaluating secondary structure of target or AO sequences, testing AO affinity for a target sequence, and evaluating AO specificity for SARS-CoV-2 RNA.

Figure 2:
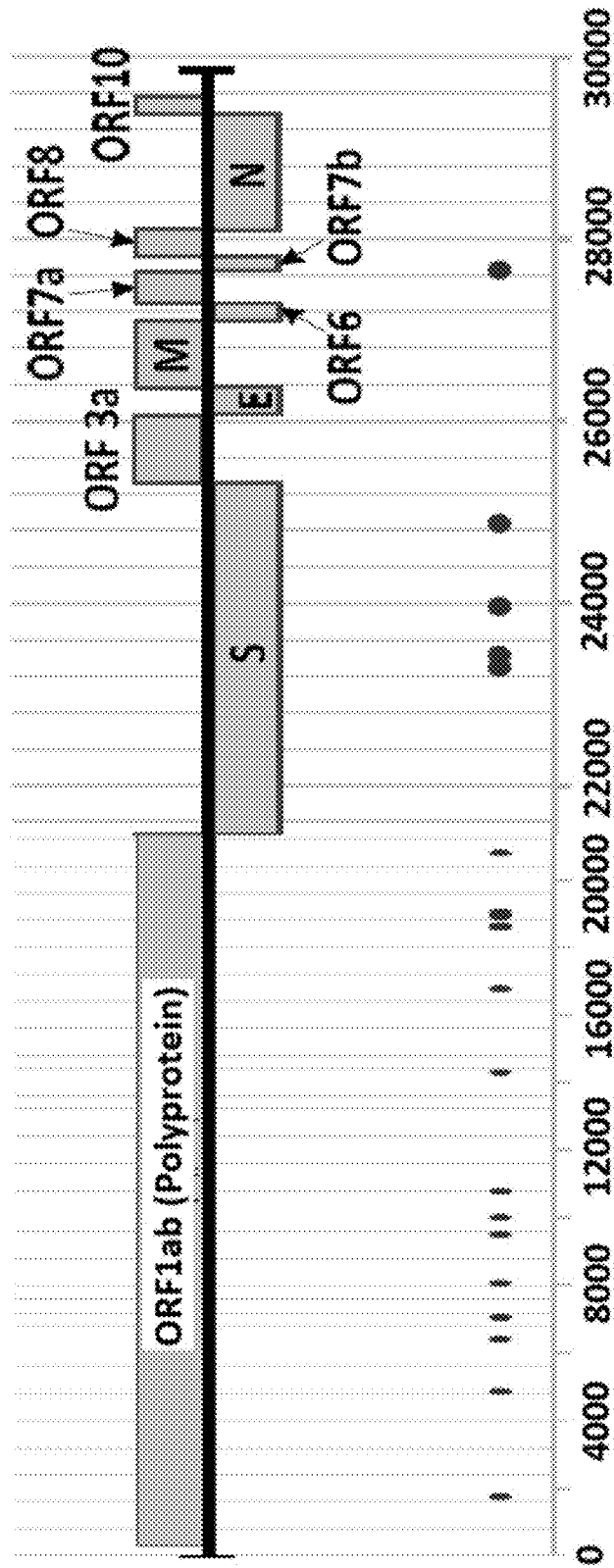
FIG. 2 shows approximate locations of AO targets (dots) in the SARS-CoV-2 RNA genome.

Using these criteria, 293 targeting sequences were identified that met these criteria as shown in FIG. 2, including (1) having a desired RNA structure (2) a desired range of adenosine/pyrimidine ratio, (3) having a length up to 20 nucleotides, and (4) not containing CG or a stretch of more than 2Cs or 2Gs. The sequences of AO targets are described in Table 1. The approximate locations of these nucleic acids in the SARS-CoV-2 genome are shown in FIG. 2.

Example 2

Knock-Down Efficiency of AOs Using A549 Cells

In order to identify which of the AOs most efficiently reduced levels of their respective target RNAs, human alveolar basal epithelial cells, A549 cells, were transfected with expression vectors carrying the target sequences for the AOs.

The cells were transfected with the expression vectors expressing mRNA transcripts or an RNA fragment of the viral genome that contained the respective target sequence. The A549 cells were transfected with the expression vectors and then treated with three different concentrations (10 nM, 20 nM, or 100 nM) of the respective AOs and dose responses for each AO were determined.

The A549 cells were cultured as described by and incorporated by reference to Chen, Y., et al., *Dexamethasone-mediated repression of MUC5AC gene expression in human lung epithelial cells*, AM J RESPIR CELL MOL BIOL. 2006. 34, 338-47. Briefly, the cells were seeded in 6 well plates at $4 \times 10^5$/well, and then transfected with expression vectors that expressed Red Fluorescent Protein (RPF) tagged viral proteins using Lipofectamine 2000™ or a generic equivalent. Expression vectors were purchased from Origene® containing ORFs plus RFP tag. The RFP tag permits visualization of the protein products and reduction of them.

Twenty-four hours after the transfection, the cells were treated with gapmer AOs to determine efficacy and to evaluate dose-responses as described previously by Neuman, B. W., et al., *Inhibition, escape, and attenuated growth of severe acute respiratory syndrome coronavirus treated with antisense morpholino oligomers*, J VIROL. 2005. 79, 9665-76. Briefly, the cells were transfected with gapmers at three different concentrations (10 nM, 50 nM, 100 nM) using Lipofectamine RNAiMAX reagent.

Total RNA from the cells were extracted 24 hours after the treatment. Real-time qRT-PCR was conducted to determine the efficiency of RNA knockdown by of each of the gapmers. A control gapmer having the same 2'-O-methyl (2'-O-Me) design but with a random, non-specific sequence was used as an AO control in addition to a transfection only control. The experiments were conducted in quadruplicate and repeated three times.

Figure 3:
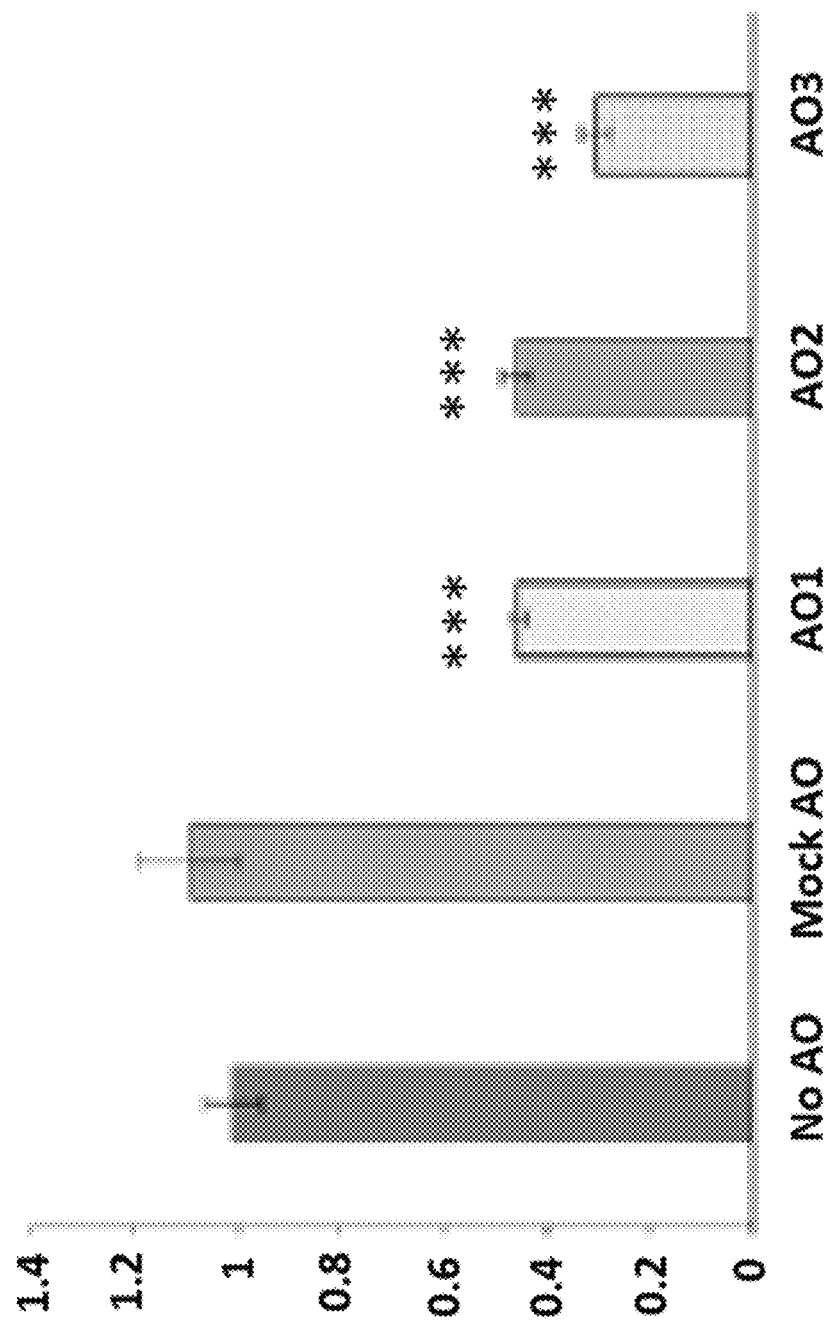
FIG. 3 shows that 2'-O-methyl (2'-O-Me) gapmers targeting SARS-CoV-2 sequences significantly reduced the viral RNAs. The target viral RNAs transiently expressed in A549 cells were reduced after the cells were treated with AOs (100 nM) targeting the RNA for 24 hours (n=6). Two-tailed student t-test. ***p<0.005.

In an experiment performed following the above protocol, the results showed that 100 nM of three AOs targeting different sequences significantly reduced the viral mRNA levels, as shown in FIG. 2. AO1, AO2 and AO3 caused significant knockdown of target RNA compared to two controls as shown in FIG. 3. The sequence of AO1 was 5'-TGATAGAGGTTTGTGGTGGT-3' which was complementary to the targeting sequence SEQ ID NO: 108 in Table 1. AO1 comprised two 2'-O-Me domains located at 5' and 3' ends respectively. Each 2'-O-Me domain comprised 5 nucleotides. The sequence of AO2 was 5'-ACCATGTGTT-GAACCTTTCT-3' which was complementary to the targeting sequence SEQ ID NO: 211 in Table 1. AO2 comprised two 2'-O-Me domains located at 5' and 3' ends respectively. Each 2'-O-Me domain comprised 5 nucleotides. The sequence of AO3 was 5'-TTGAGGTACACACTTAATAG-3' which was complementary to the targeting sequence SEQ ID NO: 292 in Table 1. AO3 comprised two 2'-O-Me domains located at 5' and 3' ends respectively. Each 2'-O-Me domain comprised 5 nucleotides.

Figure 4A:
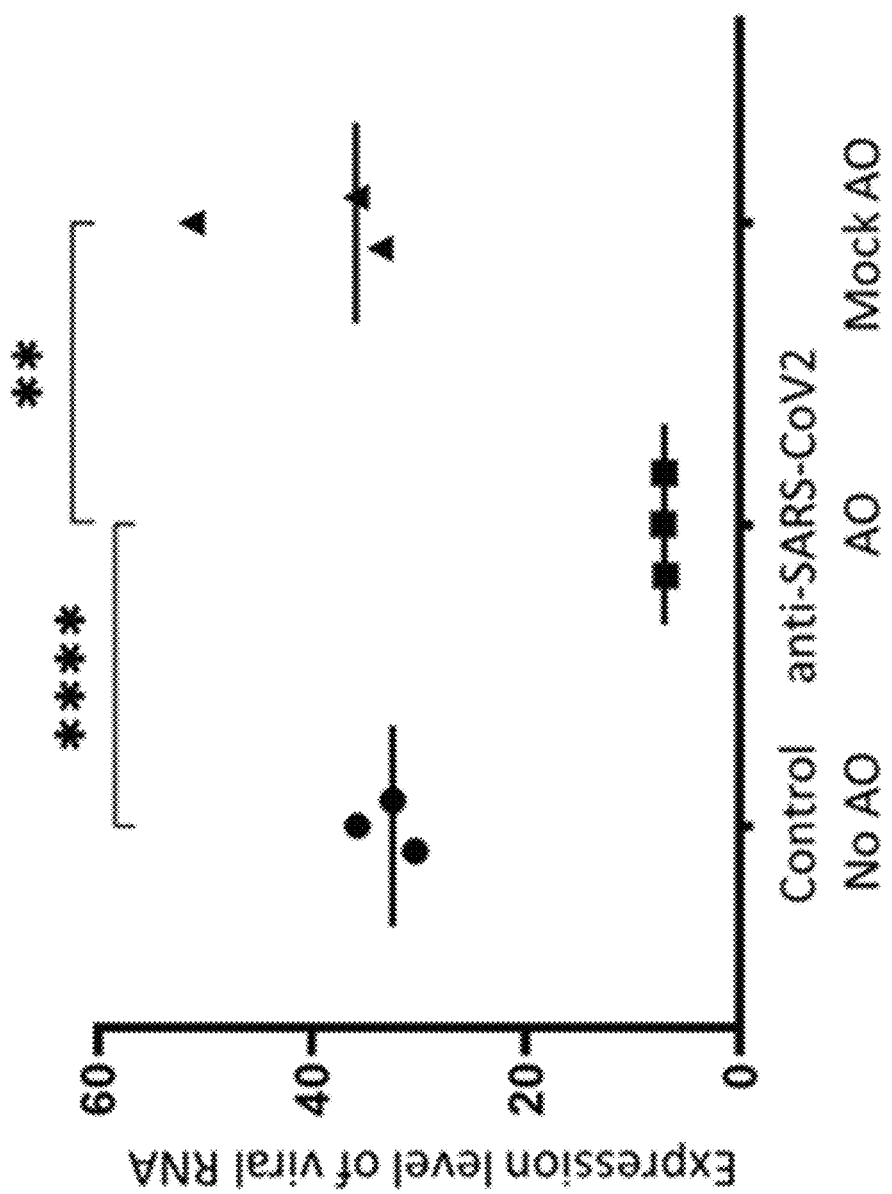
FIGS. 4A and 4B show that 2'-MOE gapmers targeting SARS-CoV-2 sequences significantly reduced the viral RNAs. The target viral RNAs transiently expressed in A549 cells were reduced after the cells were treated with AOs (100 nM, transfection) targeting the RNA for 24 hours (n=3) (FIG. 4A); or treated with AOs (1 µM, no transfection) targeting the RNA for 24 hours (n=3) (FIG. 4B). Two-tailed student t-test. p<0.01, *p<0.005.
Figure 4B:
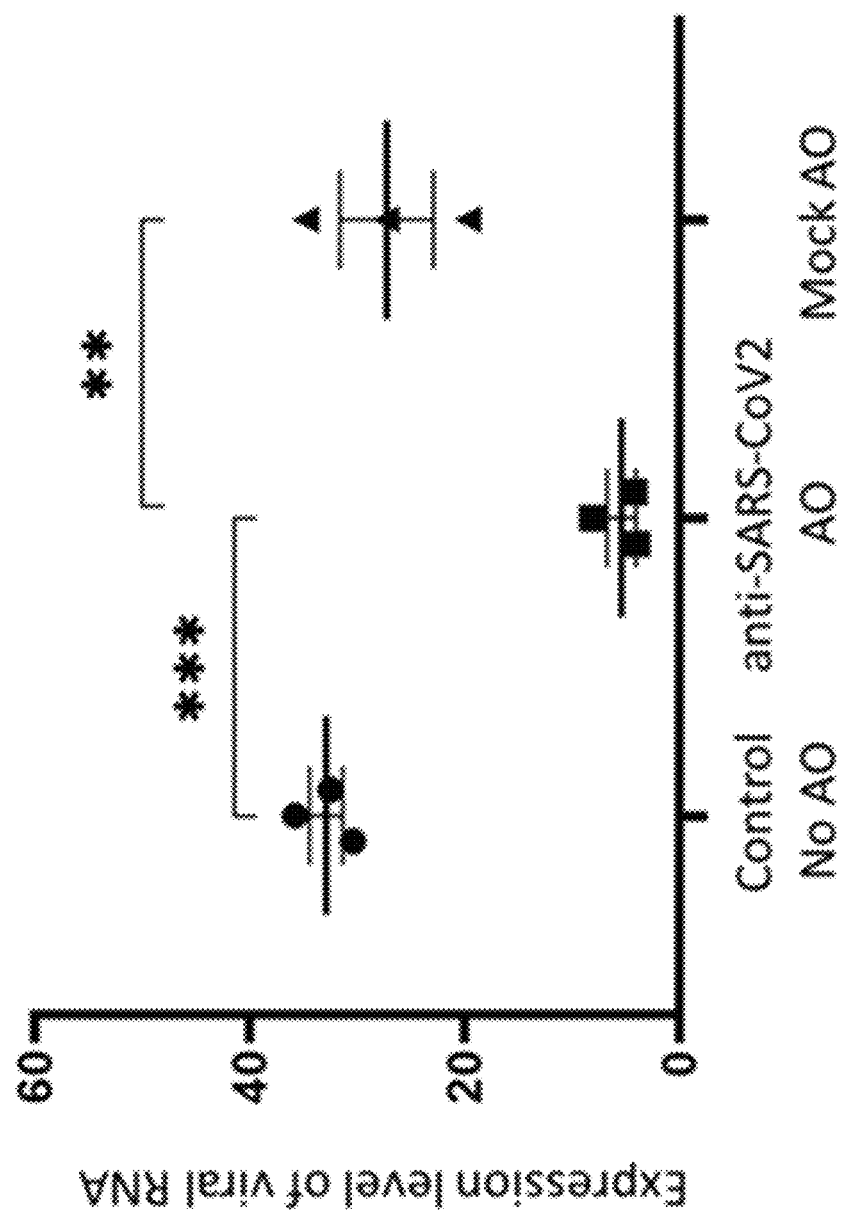

AO4 (2'-MOE modified nucleotides) was tested with or without transfection using the same experimental protocol. The data demonstrated high knockdown efficiency under both conditions as shown in FIG. 4. The sequence of AO4 was 5'-TTGAGGTACACACTTAATAG-3' which was complementary to the targeting sequence SEQ ID NO: 292 in Table 1. AO4 comprised two 2'-MOE domains located at 5' and 3' ends respectively. Each 2'-MOE domain comprised 5 nucleotides.

Other examples of AOs include AO5, AO6, AO7, AO8, and AO9 which comprised two 2'-MOE domains or two 2'-O-Me domains at 5' and 3' ends respectively. Each 2'-MOE domain or 2'-O-Me domains comprised 5 nucleotides. The sequence of AO5 was 5'-TTAAACCCTGACCCGGGTAA-3' which was complementary to the targeting sequence SEQ ID NO: 45 in Table 1. The sequence of AO6 was 5'-GTCTCCTA-CAACTTCGGTAG-3' which was complementary to the targeting sequence SEQ ID NO: 77 in Table 1. The sequence of AO7 was 5'-TGACACCCCTCGACATCGAA-3' which was complementary to the targeting sequence SEQ ID NO: 206 in Table 1. The sequence of AO8 was 5'-TAGGTCAAC-CACGTTCCCGA-3' which was complementary to the targeting sequence SEQ ID NO: 284 in Table 1. The sequence of AO9 was 5'-CAGAAAGAGGTCCTAGTATG-3' which was complementary to the targeting sequence SEQ ID NO: 293 in Table 1. Some of the designs of AOs comprised LNA domains. The AOs comprised two LNA domains at 5' and 3' ends respectively. Each LNA domain comprised from about 3 to about 5 nucleotides.

Example 3

Knock-Down Efficiency Using Human Epithelial Cells (NHBE)

The knockdown efficiency is validated using a different cell line: normal human bronchial epithelium (NHBE) and primary cells from the upper respiratory tract; see Gutierrez, M. J., et al., *Airway Secretory microRNAome Changes during Rhinovirus Infection in Early Childhood*, PLoS ONE. 2016, 11, e0162244; Wolf, S., et al. *Conditional reprogramming of pediatric airway epithelial cells: A new human model to investigate early-life respiratory disorders*, PEDIATR ALLERGY IMMUNOL. 2017, 28, 810-817 both of which are incorporated by reference. A control AO with the same 2'-MOE gapmer design but which contains a random, non-specific sequence. The expression vectors express RFP tagged viral proteins and the expression of RFP is used to evaluate transfection efficiency. The experiments are conducted in quadruplicate and repeated three times.

Example 4

Off-Target Evaluation of AOs

To determine whether AOs having potential binding affinity for RNA other than SARS-CoV-2 RNA ("off-target binders'), RNA-seq and quantitative RT-PCR are conducted to determine expression changes in the treated cells.

The global expression pattern of RNA from treated cells (n=5) is compared with those of untreated cells. RNA-seq data of cells that are transfected with empty vector are used as baseline. High throughput TruSeq (Illumina) stranded mRNA sequencing (RNA-seq) are performed by New York Genome Center which recently performed RNA-seq for human myoblasts treated with LNA gapmers, Lim, et al., supra. These data show which AOs share sequence similarity to the human transcriptome and could be potential off-targets.

For data analysis of the off-targets, multiple testing correction is performed (FDR, p<0.05) by the New York Genome Center to provide a data list identifying transcripts that are differentially expressed. In addition to the specific genes identified by sequence similarity, a pathway analysis is performed to determine whether any related molecular networks and pathways are affected. RNA-seq data is validated by quantitative RT-PCR. The off-target effects are determined based on how many potential off-target genes are knocked down and by the percentage of knockdown.

Example 5

Effects of AOs on Immune System

To evaluate potential toll-like receptor (TLR)-mediated immune responses quantitative RT-PCR and ELISA are performed. Unmodified bases and/or sequence motifs in oligonucleotides such as AOs can trigger secretion of cytokines such as TNFα, IL1β, and IFNα I adherent PBMC cells. Exogenous nucleic acids may trigger the TLR-mediated immune responses to different extents depending on the sequences; see Judge, A. & MacLachlan, I., *Overcoming the innate immune response to small interfering RNA*, HUMAN GENE THERAPY. 2008. 19, 111-24. For example, innate immune responses can be triggered through toll-like receptors (TLRs) which are activated by molecules typically associated with viral, bacterial, or fungal pathogens.

Effects of each AO on toll-like receptor (TLR)-mediated immune responses are determined by quantifying using ELISA cytokines released by human peripheral blood mononuclear cells (PBMC). To evaluate whether the AOs trigger innate immune responses, human peripheral blood mononuclear cells (PBMC) are seeded in a round bottom 96-well plate at ~1-6,000,000 cells/well in 150 uL/well of RPMI medium. The cells are then treated with the AOs (100 nM) using RNAiMax, Lipofectamine 2000. Poly(dA:dT) at 1-10 ng/m and ImStim duplex at 100 nM as a positive control for IL1β/INFα response and INFα/TNFα response, respectively. Supernatants are harvested 24-48 hours after the AO treatment for ELISA assays to determine whether the IL1β, INFα TNFα are induced by the treatment. qRT-PCRs are performed to quantify the transcripts.

Example 6

In Vitro Efficacy and Toxicity Assessment of AOs

A 3D human respiratory airway cell model constructed by Epithelix is used to test the delivery and efficacy of AO treatment. The tissue model is infected with SARS-CoV-2 for testing and results are used to further prioritize selected AOs.

Prior to evaluation using the Epithelix model, AOs are prioritized based on capacity to consistently and effectively reduce the viral RNA targets in the cell models and have the least recognition of off-targets and least stimulatory effects on the immune system.

The knockdown effect and toxicity of the AOs upon infection of the model with SARS-COV-2 are determined. The viral strain used by Epithelix is the French circulating strain and evaluations is performed according to Epithelix protocols using fully differentiated human nasal epithelial cells cultured at the air-liquid interface. Epithelia Muci-lAir™ is reconstituted with a mixture of cells isolated from 14 different normal nasal donors.

The infection tests with SARS-COV-2 are conducted at the VirNext SL3 facilities in France. The test includes 1) effect of AO treatment on virus replication based on virus genome copy number is determined by Taqman RT-PCR and infectious titer quantification/TCID50 analysis; 2) toxicity is evaluated by monitoring tissue integrity, including tissue histology, trans-epithelial electrical resistance (TEER) measurement, cell death, and cytokines released from the tissue.

The AOs are tested at three concentrations (200 nM, 500 nM and 1 The concentration is higher than the prior quick screenings. Here, the cells are transfected with a small amount of AOs to determine efficiency. The AOs are delivered without transfection to allow the AOs to enter the cells without a carrier which will allow a more accurate estimation of the dosage in clinical studies. The AOs are administered via apical exposure to mimic delivery via the trachea in a clinic. The experiment is repeated three times with triplicates in each experiment. A PBS vehicle only control is conducted. A positive control for cytotoxicity is based on cells treated with Triton X-100.

The terminology used herein is for the purpose of describing particular embodiments only and is not intended to be limiting. Unless specifically defined herein, all terms used herein have the same meaning as they would to one skilled in the art of the present invention. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present disclosure relates to compositions comprising a nucleotide sequence. In some embodiments, the nucleotide sequence comprises (i) an RNA-binding domain from about 5 to about 30 nucleotides complementary to a region of a SARS-CoV-2 RNA and (ii) at least one locked nucleic acid (LNA) domain or 2'-O-methoxyethyl (2'-MOE) domain comprising from about 1 to about 5 nucleotides, or a salt thereof.

As used herein, "activity" in the context of LNA or 2'-O-methoxyethyl (2'-MOE) gapmer activity refers to the ability of a nucleic acid to bind to a target domain of a nucleic acid sequence and/or bind a cellular receptor or binding partner to a degree and for a period of time sufficient to allow entry of the nucleic acid sequence into a target cell (a cell expressing a mRNA with a target domain), such as a cell in the respiratory mucosa or upper or lower respiratory system. In some embodiments, the activity refers to the ability of a nucleic acid to bind to a target domain of a nucleic acid sequence. Such activity can be measured in a variety of ways as known in the art. For example, mRNA or protein expression, activity, or level of a gene sequence can be measured, and targeting the gene sequence can be assayed for their ability to reduce the expression, activity, or level of the gene. For example, a cell can be transfected with, transformed with, or contacted with a nucleotide sequence disclosed herein. The activity can be measured by monitoring the expression of the target nucleic acid sequence and comparing expression to a cell not transfected, transformed or contacted with disclosed nucleic acid sequences. In some embodiments, LNA gapmer or 2'-O-methoxyethyl (2'-MOE) activity can be measured by SARS-Cov-2 mRNA or protein expression.

The term "analog" as used herein refers to compounds that are similar but not identical in chemical formula and share the same or substantially similar function of the compound with the similar chemical formula. In some embodiments, the analog is a mutant, variant or modified sequence as compared to the non-modified or wild-type sequence upon which it is based. In some embodiments, compositions of the disclosure include modifications or analogs that are at least about 70%, about 75%, about 80%, about 85%, about 90% about 91%, about 92%, about 93%, about 94%, about 95%, about 96%, about 97%, about 98% or about 99% homology to any of the disclosed nucleic acids disclosed herein. In some embodiments the analog is a functional fragment of any of the disclosed nucleic acid sequences. In some embodiments, the analog is a salt of any of the disclosed nucleic acid sequences. In such embodiments, the analog may retain about 99%, 98%, 97%, 96%, 95%, 94%, 93%, 92%, 91%, 90%, 85%, 80%, 75%, 70% or less biological activity as compared to the natural or wild-type sequences upon which it is based.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside. In some embodiments, the nucleotide is characterized as being modified if the 3' phosphate group is covalently linked to a contiguous nucleotide by any linkage other than a phosphodiester bond.

"Oligonucleotide" refers to a compound comprising a plurality of linked nucleotides. In certain embodiments, one or more of the plurality of nucleotides is modified. In certain embodiments, an oligonucleotide comprises one or more ribonucleotides (RNA) and/or deoxyribonucleotides (DNA).

"Internucleoside linkage" means a covalent linkage between adjacent nucleotides of an oligonucleotide.

As used herein, a "gapmer" is a region of a natural or nonnatural nucleotide sequence having one or more nucleotides that can bind to a target oligonucleotide. In some embodiments, the gapmer comprises a domain comprising one or a plurality of modified or unmodified deoxynucleotides. In some embodiments, the gapmer comprises a domain comprising one or a plurality of modified or unmodified ribonucleotides. In some embodiments, the gapmer hybridization to a target sequence induces cleavage of at least a portion of the target oligonucleotide by Rnase H.

In some embodiments, the gapmer is a chimeric antisense compound. In some embodiments, the gapmer is an LNA gapmer comprising a DNA gapmer domain and an LNA domain. In some embodiments, the DNA gapmer domain is flanked by two LNA domains.

In some embodiments, the gapmer is a 2'-O-methoxyethyl (2'-MOE) gapmer comprising a DNA gapmer domain and a 2'-O-methoxyethyl (2'-MOE) domain. In some embodiments, the DNA gapmer domain is flanked by two 2'-O-methoxyethyl (2'-MOE) domains.

In some embodiments, the gapmer has an internal region having a plurality of nucleotides that support RNase H cleavage, positioned between external regions having one or more nucleotides. In some embodiments, the nucleotides comprising the internal region are chemically distinct from the nucleotide or nucleotides comprising the external regions. In certain embodiments, the target oligonucleotide comprises from about 5 to about 200, from about 5 to about 50, from about 10 to about 100, from about 10 to about 50, from about 10 to about 25, from about 15 to about 100, from about 15 to about 50, from about 5 to about 25, or from about 15 to about 25 nucleotides. In some embodiments, the gapmer comprises a series of contiguous or noncontiguous deoxyribonucleic acid and ribonucleic acid.

The disclosure relates to a nucleic acid sequence disclosed herein also comprising one or a plurality of modified nucleotides.

In some embodiments, the compositions of the disclosure comprise a nucleic acid sequence disclosed herein comprising one or a plurality of modified oligonucleotides.

In some embodiments, the composition comprises any, one, two, three or more nucleic acid sequences disclosed herein comprising a modified oligonucleotide consisting of a number of linked nucleotides. Thus, the compound or compounds may include additional substituents or conjugates.

"Modified oligonucleotide" means an oligonucleotide having one or more modifications relative to a naturally occurring terminus, sugar, nucleobase, and/or internucleoside linkage. A modified oligonucleotide may comprise unmodified nucleotides at one or a plurality of any of the positions of the disclosed nucleic acids.

"Single-stranded modified oligonucleotide" means a modified oligonucleotide which is not hybridized to a complementary strand. In some embodiments, the compositions of the disclosure relate to a nucleic acid molecule that is a single-stranded modified oligonucleotide comprising any one or more domains disclosed herein.

The nucleic acid sequences of the disclosure can comprise one or more modified nucleotides.

The terms "modified nucleoside" mean a nucleoside having any change from a naturally occurring nucleoside. A modified nucleoside may have a modified sugar and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

The term "nucleic acid" is defined as a molecule formed by covalent linkage of two or more nucleotides. The terms "nucleic acid," "polynucleotide" and "nucleotide sequence" are used interchangeably herein. The term "nucleic acid analogue" refers to a nonnatural nucleic acid binding compound. Nucleotide analogues and nucleic acid analogues are described in e.g. Freier & Altmann, NUCL. ACID RES., 1997, 25, 4429-4443 and Uhlmann, CURR. OPINION IN DRUG & DEVELOPMENT, 2000, 3(2): 293-213 (both incorporated by reference).

The term "locked nucleic acid" or "LNA" refers to a modified nucleotide, more specifically a nucleotide containing one bicyclic nucleoside analogue, also referred to as an LNA monomer, or an oligonucleotide containing one or more bicyclic nucleoside analogues. In LNA, a 2'O-4'C-methylene linkage locks the furanose ring, making up the ribose sugar, in a C3'-end conformation which mimics the RNA structure. In some embodiments, LNA domains are from about 1 to about 5 nucleotides or from about 1 to about 10 nucleotides in length. In some embodiments, LNA domains are an oligonucleotide of about 3 nucleotides in length.

An "LNA gapmer," as used herein refers to an oligonucleotide composed of LNA segments flanking a central DNA gap that can be phosphorothionated. In some embodiments, the central DNA gap is about 6 or more nucleotides, for example, from about 7 to about 10 nucleotides. In some embodiments, the central DNA gap is 11 or more An "2'-O-methoxyethyl (2'-MOE) gapmer," as used herein refers to an oligonucleotide composed of 2'-O-methoxyethyl (2'-MOE) segments flanking a central DNA gap that can be phosphorothionated.

In some embodiments, the central DNA gap is about 6 or more nucleotides, for example, from about 7 to about 10 nucleotides. In some embodiments, the central DNA gap is 11 or more nucleotides in length.

In some embodiments, the LNA or 2'-O-methoxyethyl (2'-MOE) gapmer (or other gapmer) is from about 8 to about 120 nucleotides. In some embodiments, the gapmer is from about 10 to about 100 nucleotides. In some embodiments, the gapmer is from about 10 to about 80 nucleotides. In some embodiments, the gapmer is from about 10 to about 60 nucleotides. In some embodiments, the gapmer is from about 10 to about 40 nucleotides. In some embodiments, the gapmer is from about 10 to about 30 nucleotides. In some embodiments, the gapmer is from about 10 to about 25 nucleotides. In some embodiments, the gapmer is from about 10 to about 20 nucleotides. In some embodiments, the gapmer is from about 8 to about 30 nucleotides. In some embodiments, the LNA gapmer is from about 8 to about 20 nucleotides. In some embodiments, the LNA gapmer is from about 14 to about 16 nucleotides.

The terms "biophysically effective amount" refers to an amount of nucleic acid in a system under one or a plurality of physiological conditions (such as, temperature, pH, exposure to percent oxygen, etc.) sufficient for a nucleic acid sequence disclosed herein or an analog thereof to associate with a DNA gap domain target or a microRNA target. In some embodiments, the nucleic acid sequence of the disclosure is in a biophysically effective amount.

It should be understood that some nucleic acid sequences (such as LNA or 2'-O-methoxyethyl (2'-MOE) gapmer targets) or any analog thereof described herein are intended to include nucleic acid sequences comprising polynucleotides bearing one or more insertions, deletions, or substitutions, or any combination thereof, of nucleic acid residues as well as modifications other than insertions, deletions, or substitutions of nucleic acid residues.

In some embodiments, in the presence of one or a plurality of proteins (or functional fragments thereof) and a target sequence, the one or plurality of proteins and the nucleic acid element forms a biologically active complex and/or can be enzymatically active on a target sequence.

The term "target nucleic acid", as used herein refers to the DNA or RNA sequence encoding SARS-CoV-2 mRNA or proteins (e.g., for down regulation). In one embodiment, for example when used in research or diagnostics the "target nucleic acid" may be a cDNA, viral sequence embedded in a host genome, or a synthetic oligonucleotide derived from the above DNA or RNA nucleic acid targets. The oligomer according to the invention is preferably capable of hybridizing to the target nucleic acid. In some embodiments, the target nucleic acid is a SARS-Cov-2 RNA or any nucleotide or nucleotide sequence thereof. In some embodiments an AO sequence will have 1, 2 or 3 mismatches with a SARS-CoV-2 target sequence.

The terms "target domain" refers to an amino acid sequence or nucleic acid element or domain within a nucleic acid sequence (or polynucleotide sequence) that binds to an LNA or 2'-O-methoxyethyl (2'-MOE) gapmer either covalently or non-covalently when the LNA or 2'-O-methoxyethyl (2'-MOE) gapmer is in contact with the target domain in a biophysically effective amount.

In some embodiments, the target domain consists of no more than about 5, 10, 15, 20, 25, 30, 35, 40, 45, 50, 60, 70, 80, 90, 100, 110, 120, 130, 140, 150, 160, 170, 180, 190, 200, 210, 220, 230, 240, 250 or more nucleotides in length. In some embodiments, the target domain is expressed by a cell, such as a respiratory system cell.

In some embodiments, the target domain is expressed by a human lung epithelial cells or cultured epithelial cells.

In some embodiments, a target domain or sequence is located in the nucleus or cytoplasm of a cell. In some embodiments, the target sequence may be within, or associated with, an organelle of a eukaryotic cell, for example, mitochondrion or chloroplast. In some embodiments, the compositions of the disclosure comprise one or a plurality of nucleic acid sequences comprising at least one LNA or r 2'-O-methoxyethyl (2'-MOE) gapmer that recognizes one or a plurality of target domains, wherein the target domain or domains are expressed on the surface of a cell.

When multiple, different nucleic acid sequences disclosed herein are used together, a single expression construct may be used to target an LNA gapmer to multiple, different, corresponding target domains sequences within and/or on a cell. In some embodiments, the disclosure relates to a composition with one or a plurality of vectors expressing a first, second, third, and/or fourth or more nucleic acid sequence disclosed herein.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "functional fragment" means any portion of a nucleic acid sequence from which the respective full-length nucleic acid relates that is of a sufficient length and has a sufficient structure to confer a biological affect that is identical, at least similar to or substantially similar to the full-length polypeptide or nucleic acid upon which the fragment is based. In some embodiments, a functional fragment is a portion of a full-length sequence that still biologically functional as compared to the full-length or wild-type sequence. In some embodiments, the functional fragment may have a reduced biological activity, about equivalent biological activity, or an enhanced biological activity as compared to the wild-type or full-length nucleic acid sequence upon which the fragment is based.

In some embodiments, the functional fragment is derived from the sequence of an organism, such as a human. In such embodiments, the functional fragment may retain about 99%, 98%, 97%, 96%, 95%, 94%, 93%, 92%, 91%, or 90% sequence activity to the full-length sequence upon which the sequence is derived. In some embodiments, the functional fragment is about 99%, 98%, 97%, 96%, 95%, 90%, 85%, 80%, 75%, 70%, 65%, or 60% sequence homology to the full-length nucleic acid sequence upon which the sequence is derived. In such embodiments, the functional fragment may retain about 99%, 98%, 97%, 96%, 95%, 94%, 93%, 92%, 91%, 90%, 85%, 80%, 75%, 70% or less biological activity as compared to the full-length sequences upon which it is based. In some embodiments, the composition provided comprises one, two, three or more nucleic acid sequences or salts thereof that is a functional fragment retaining 99%, 98%, 97%, 96%, 95%, 94%, 93%, 92%, 91%, 90%, 85%, 80%, 75%, or 70% sequence identity to any sequence identified in Table 4. In some embodiments, the composition provided comprises a therapeutically effective amount of a nucleic acid molecule or multiple nucleic acid molecules or salts thereof that comprise one, two, three or more nucleic acid sequences or salts thereof that is a variant having 99%, 98%, 97%, 96%, 95%, 94%, 93%, 92%, 91%, 90%, 85%, 80%, 75%, or 70% sequence identity to any sequences identified herein. In the case of LNA or 2'-O-methoxyethyl (2'-MOE) gapmers, such embodiments comprise a composition comprising a therapeutically effective amount of a nucleic acid molecule or multiple nucleic acid molecules or salts thereof, wherein each nucleic acid molecule or salt thereof comprises a first and a second nucleic acid sequences that comprise at least one gapmer domain that is a variant having 99%, 98%, 97%, 96%, 95%, 94%, 93%, 92%, 91%, 90%, 85%, 80%, 75%, or 70% sequence identity to any sequence identified in Table 4 or any sequence capable of binding the target domain identified herein.

The disclosure relates to nucleic acids disclosed herein unsolvated forms as well as solvated forms, including hydrated forms. The compounds of the disclosure also are capable of forming both pharmaceutically acceptable salts, including but not limited to acid addition and/or base addition salts. Furthermore, compounds of the present disclosure may exist in various solid states including an amorphous form (noncrystalline form), and in the form of clathrates, prodrugs, polymorphs, bio-hydrolysable esters, racemic mixtures, nonracemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present disclosure.

A "polymorph" refers to solid crystalline forms of the one or more nucleic acid sequences disclosed herein. In some embodiments, one or more nucleic acids disclosed herein are in a polymorph form.

Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

The nucleotide sequences of the present disclosure can be administered, inter alia, as pharmaceutically acceptable salts, esters, or amides. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like.

The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., *Pharmaceutical Salts, J Pharm Sci*, 66: 1-19 (1977), which discloses salt forms of nucleic acids and which is incorporated by reference in its entirety.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, intrans, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after synthesis or polymerization, such as by conjugation with a labeling component.

The oligonucleotides of the disclosure also include those nucleic acid sequences disclosed herein that comprise nucleotides connected by charged linkages, and/or whose sequences are divided into at least two subsequences. In some embodiments, a first, second, and third subsequence or domains include a DNA gap domain and a locked nucleic acid (LNA) or 2'-O-methoxyethyl (2'-MOE) domain. In some embodiments the nucleic acid sequence comprises two LNA or 2'-O-methoxyethyl (2'-MOE) domains contiguously or non-contiguously flanking a central DNA gap domain.

In the context of this disclosure, the term "oligonucleotide" also refers to a plurality of nucleotides joined together in a specific sequence from naturally and nonnaturally occurring nucleobases. Nucleobases of the disclosure are joined through a sugar moiety via phosphorus linkages, and may include any one or combination of adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The sugar moiety may be a modified deoxyribose or ribose with one or more modifications on the C1, C2, C3, C4, and/or C5 carbons.

The oligonucleotides of the disclosure may also comprise modified nucleobases or nucleobases having other modifications consistent with the spirit of this disclosure and in particular modifications that increase their nuclease resistance in order to facilitate their use as therapeutic, diagnostic or research reagents.

As used herein, "more than one" or "two or more" 2, 3, 4, 5, 6, 7, 8, 9, or 10 or more where "more" may be an positive integer above 10 that corresponding to the length of nucleotides in the nucleotide sequences. In some embodiments, "more than one" means 2, 3, 4, or 5 of the amino acids or nucleic acids or mutations described herein. In some embodiments, "more than one" means 2, 3, or 4 of the amino acids or nucleic acids or mutations described herein. In some embodiments, "more than one" means 2 or 3 of the amino acids or nucleic acids or mutations described herein. In some embodiments, "more than one" means 2 of the amino acids or nucleic acids or mutations described herein.

The terms "therapeutically effective amount" mean a quantity sufficient to achieve a desired therapeutic effect, for example, an amount which results in the prevention or amelioration of or a decrease in the symptoms associated with a disease that is being treated. The amount of composition administered to the subject will depend on the type and severity of the disease such as COVID-19 and on the characteristics of the individual, such as general health, age, sex, body weight and tolerance to drugs. It will also depend on the degree, severity and type of disease. The skilled artisan will be able to determine appropriate dosages depending on these and other factors. The regimen of administration can affect what constitutes an effective amount. The compound of the disclosure can be administered to the subject either prior to or after the onset of disease or disorder. Further, several divided dosages, as well as staggered dosages, can be administered daily or sequentially, or the dose can be continuously infused, or can be a bolus injection. Further, the dosages of the compound(s) of the disclosure can be proportionally increased or decreased as indicated by the exigencies of the therapeutic.

An appropriate dosage of the antisense oligonucleotides disclosed herein can be determined by one skilled in the art depending on pharmacokinetic factors including route of administration, target site, tissue or organ within the body and the severity of infection; Geary, et al., *Pharmacokinetics, biodistribution and cell uptake of antisense oligonucleotides*, ADV DRUG DELIVER REV, 2015, 87:46-51; Geary, et al. *Pharmacokinetic properties of 2'-O-(2-methoxyethyl)-modified oligonucleotide analogs in rats*, J PHARMACOL EXP THER. 2001 March; 296(3):890-7 both incorporated by reference. Effective amounts of the compounds of the present disclosure, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day.

A therapeutically effective amount of a pharmaceutical composition comprising any one or a plurality of any of the nucleic acid sequences disclosed herein can also be administered in combination with two, three, four or more nucleic acid sequences disclosed herein, or with one or more additional therapeutic compounds. Those skilled in the art will recognize and determine a therapeutically effective amount of any of the nucleic acid sequences disclosed herein whether calculated when administered alone or part of a therapeutic regimen that includes one or more other therapeutic agents and/or one or more other therapeutic treatments or interventions.

Generally, therapeutically effective amount refers to an amount of a nucleic acid sequence that alone or in combination with one or a plurality of other therapeutic compounds causes a transfection of the nucleic acid sequence into a target cell (such as a cell of the respiratory system) and/or hybridization of the one or more miRNA domains within the nucleic acid sequences sufficient reduce or inhibit expression of a mRNA sequence with the cell, thereby ameliorating symptoms, or reversing, preventing or reducing the rate of progress of disease, or extend life span of a subject when administered alone or in combination with other therapeutic agents or treatments as compared to the symptoms, rate of progress of disease, or life span of an individual not receiving a therapeutically effective amount the one or plurality of nucleic cells disclosed herein.

The terms "treating" and "to treat", mean to alleviate signs and/or symptoms, eliminate the causation either on a temporary or permanent basis, or to prevent or slow the appearance of signs and symptoms. The term "treatment" includes alleviation, elimination of causation (temporary or permanent) of, or prevention of signs and/or symptoms and disorders associated with any condition, such COVID-19 or other disorders associated with SARS-CoV-2 exposure or infection. The treatment may be a pre-treatment (as a preventative treatment) and/or treatment at the onset of signs and/or symptoms.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

A "base," as used herein, means a group selected from the following: adenine, guanine, cytosine, uracil, thymine, uridine, pyrimidine, purine, pseudouridine, inosine, hypoxanthine, rhodamine, fluorescein, 2-aminopurine, cytidine, 2'-deoxycytidine, 1,3-diaza-2-oxophenothiazine, dihydrouridine, queuosine, wyosine, cyanophage S-2L diaminopurine, isoguanine, isocytosine, diaminopyrimidine, 2,4-difluorotoluene, 4-methylbenzimidazole, isoquinoline, pyrrolo [2,3-b]pyridine, 2-amino-6-(2-thienyl)purine, pyrrole-2-carbaldehyde, 2,6-bis(ethylthiomethyl)pyridine, pyridine-2,6-dicarboxamide, 2'-deoxyinosine, 2-amino-8-(2-thienyl)purine, pyridine-2-one, 7-(2-thienyl)imidazo [4,5-b]pyridine, pyrrole-2-carbaldehyde, 4-[3-(6-aminohexanamido)-1-propynyl]-2-nitropyrrole, or modified derivative thereof.

The term "LNA," as used herein, means any nucleic acid analog disclosed herein comprising a cyclic structure between the C2 and C4 carbon of the sugar moiety of a nucleic acid.

The terms "subject," "individual," and "patient" are used interchangeably herein to refer to a vertebrate, preferably a mammal, more preferably a human, especially those susceptible to infection by, or which are carriers of, coronaviruses, such as SARS-CoV-2. Mammals include, but are not limited to, murines, simians, humans, farm animals, camels, llamas, alpacas, bats, cows, pigs, goats, sheep, horses, dogs, sport animals, and pets. Tissues, cells and their progeny obtained in vivo or cultured in vitro are also encompassed by the definition of the term "subject."

The term "subject" is also used throughout the specification in some embodiments to describe an animal from which a cell sample is taken or an animal to which a disclosed cell or nucleic acid sequences have been administered. In some embodiments, the animal is a human and treatment of those conditions which are specific for a specific subject, such as a human being, the term "patient" may be interchangeably used. In some embodiments a patient will be no more than 0, 0.25, 0.5, 1, 2, 3, 4, 5, 6, 7, 8, 9, 10, 15, 18, 20, 21, 25, 30, 35, 40, 45, 50, 55, 60, 65, 70, 75, 80, 85, 90, 95, 100 or >100 years old or any intermediate value within this range. In some instances in the description of the present disclosure, the term "patient" will refer to human patients suffering from a particular disease or disorder. In some embodiments, the subject may be a non-human animal from which an endothelial cell sample is isolated or provided.

"Variants" is intended to mean substantially similar sequences. For nucleic acid molecules, a variant comprises a nucleic acid molecule having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide.

As used herein, a "native" nucleic acid molecule or polypeptide comprises a naturally occurring nucleotide sequence or amino acid sequence, respectively. For nucleic acid molecules, conservative variants include those sequences that, because of the degeneracy of the genetic code, encode the amino acid sequence of one of the polypeptides of the disclosure. Variant nucleic acid molecules also include synthetically derived nucleic acid molecules, such as those generated, for example, by using site-directed mutagenesis but which still encode a protein of the disclosure. Generally, variants of a particular nucleic acid molecule of the disclosure will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular nucleic acid molecule of the disclosure (i.e., the reference DNA sequence) can also be evaluated by comparison of the percent sequence identity between the polypeptide encoded by a variant nucleic acid molecule and the polypeptide encoded by the reference nucleic acid molecule. Percent sequence identity between any two polypeptides can be calculated using sequence alignment programs and parameters described elsewhere herein. Where any given pair of nucleic acid molecule of the disclosure is evaluated by comparison of the percent sequence identity shared by the two polypeptides that they encode, the percent sequence identity between the two encoded polypeptides is at least about 70%, 75%, 80%, 85%, 90%, 91%, 92%, 93%, 94%, 95%, 96%, 97%, 98%, 99% or more sequence identity. In some embodiments, the term "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins or polynucleotides encompassed by the present disclosure are biologically active, that is they continue to possess the desired biological activity of the native or claimed protein or polynucleotide as described herein. Such variants may result from, for example, genetic polymorphism or from human manipulation. Biologically active variants of a protein of the disclosure will have at least about 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the disclosure may differ from that protein by as few as 1-15 amino acid residues, as few as 1-10, such as 6-10, as few as 5, as few as 4, 3, 2, or even 1 amino acid residue. The proteins or polypeptides of the disclosure may be altered in various ways including amino acid substitutions, deletions, truncations, and insertions. Methods for such manipulations are generally known in the art. For example, amino acid sequence variants and fragments of the proteins can be prepared by mutations in the nucleic acid sequence that encodes the amino acid sequence recombinantly.

In some embodiments, any natural or non-natural nucleic acid formula may be repeated across 1, 2, 3, 4, 5, 6, 7, 8, 9, 10 or more nucleic acids in contiguous nucleic acids or in a non-contiguous nucleotides across the length of the nucleic acid. In some embodiments, the disclosed nucleic acid sequences comprise 1, 2, 3, 4, 5, 6, 7, 8, 9, 10, 11, 12, 13, 14, 15, 16, 17, 18, 19, 20 or more contiguous or non-contiguous modified nucleic acids across a length of the nucleic acid.

In some embodiments, the composition or pharmaceutical composition disclosed herein comprises a nucleic acid disclosed herein that comprises ribonucleic acid and about 10%, 11%, 12%, 13%, 14%, 15%, 16%, 17%, 18%, 19%, 20%, 22%, 25%, 27%, 30%, 32%, 35%, 37%, 40%, 42%, 45%, 47%, 50%, 52%, 55%, 57%, 60%, 62%, or 65% modified nucleotides.

In some embodiments, any of the forgoing formulae may comprise one or a plurality of LNA or 2'-O-methoxyethyl (2'-MOE) molecules positioned between or bound to one or a plurality of modified or unmodified nucleotides.

In some embodiments, the composition or pharmaceutical composition disclosed herein comprises a nucleic acid sequence comprising a total of about 8, 10, 12, 14, 15, 16, 18, 20, 25, 30, 35, 40, 45, 50, 55, 60, 65, 70, 75, 80, 85, 90, 95, 100, or 120 nucleotides in length and comprising in 5' to 3' orientation: LNA domain or 2'-O-methoxyethyl (2'-MOE) domain and a DNA gap domain.

In some embodiments, the composition or pharmaceutical composition disclosed herein comprises a nucleic acid sequence comprising a total of about 8, 10, 12, 14, 15, 16, 18, 20, 25, 30, 35, 40, 45, 50, 55, 60, 65, 70, 75, 80, 85, 90, 95, 100, or 120 nucleotides in length and comprising in 5' to 3' orientation: a first LNA domain, a DNA gap domain and a second LNA or 2'-O-methoxyethyl (2'-MOE) domain. In some embodiments the composition or pharmaceutical composition disclosed herein comprises a nucleic acid sequence comprising a total of about 8, 10, 12, 14, 15, 16, 18, 20, 25, 30, 35, 40, 45, 50, 55, 60, 65, 70, 75, 80, 85, 90, 95, 100, or 120 nucleotides in length and comprising in 5' to 3' orientation: a first LNA or 2'-O-methoxyethyl (2'-MOE) domain, a DNA gap domain, and a second LNA domain all contiguously oriented.

In certain embodiments, the modification of the nucleotide in the DNA gap domain is one or more of 2'-O-methyl, 2'-O-fluoro, or phosphorothioate. In certain embodiments, the nucleotide is modified at the 2' position of the sugar moiety. In some embodiments, the modification at the 2' position of the sugar moiety is 2'-O-methyl or 2'-0 fluoro. In certain embodiments, the nucleotide is modified at the 3' position of the sugar moiety. In certain embodiments, the modification at the 3' position of the sugar moiety is phosphorothioate. In certain embodiments, the nucleotide is modified at both the 2' position of the sugar moiety and at the 3' position of the sugar moiety. In certain embodiments, the nucleotide is not modified at the 2' position of the sugar moiety. In certain embodiments, the nucleotide is not modified at the 3' position of the sugar moiety.

In a particular embodiment, the nucleic acid molecule comprises a DNA gap domain comprising from about 6 to about 11 nucleotides, wherein the DNA gap domain has at least 70%, 80% or 90% sequence homology to a nucleic acid sequence chosen from: SEQ ID NOS 1-293, wherein one or more of the nucleotides are modified.

In certain embodiments of the aforementioned nucleic acid molecules, only the LNA or 2'-O-methoxyethyl (2'-MOE) domain comprises one or more modified nucleotides. In certain embodiments, only the DNA gap domain of the nucleic acid molecule comprises one or more modified nucleotides. In certain embodiments, both the LNA domain and the DNA gap domain comprise one or more modified nucleotides.

The DNA gap domain can be from about 3 to about 150 nucleotides long, or longer (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length, or longer). In some cases, the DNA gap domain is from about 6 to about 50 nucleotides in length (e.g., from about 6 to about 34, 6-46, 6-40; 7-35, 7-30, 7-28, 7-25; or about 25-50, 25-55, 25-60, or 5-20 nucleotides in length).

Generally, the "DNA gap region" or "DNA gap domain" is a nucleic acid sequence designed to complement or substantially complement a target nucleic acid sequence or sequences, such as an mRNA sequence in a target cell. In some embodiments, the region of the nucleic acid is also called a "nucleotide binding region," and such terms are used equivalently in this application, because of its ability to bind to complementary or partially complementary target sequences. In some embodiments, the mRNA sequence in a target cell is a SARS-CoV-2 sequence or any transcript or portion thereof.

The term "2'-O-MOE domain" means a nucleic acid sequence designed to complement or substantially complement a target nucleic acid sequence or sequences, such as an mRNA sequence in a target cell that includes at least one, two, three, four or more 2'-MOE modifications in a nucleotide.

The nucleotide binding domain can incorporate wobble or degenerate bases to bind multiple sequences. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is from about 40% and about 60% (e.g., 40%, 45%, 50%, 55%, 60%). In some cases, the nucleotide binding region can contain modified nucleotides such as, without limitation, methylated, phosphorylated, fluorinated, or hydroxylated nucleotides. In some cases, the nucleotide binding region can contain modified nucleotides such as, without limitation, methylated, phosphorylated, fluorinated, or hydroxylated nucleotides; wherein if the nucleotide is fluorinated, the nucleotide may also be bound to one or more adjacent modified or unmodified nucleotides by a phosphorothioate bond, in either R or S orientation.

In some embodiments, the nucleotide binding region binds or is capable of hybridizing with DNA, RNA, or hybrid RNA/DNA sequences, such as any of those target sequences described herein. In some embodiments, any of the domains or elements comprises DNA, RNA, or hybrid RNA/DNA sequences. In some embodiments, the DNA gap domain comprises from about 5% to about 100% modified nucleotides based upon the total number of the nucleotides in the entire sequence.

In some embodiments, the DNA gap domain comprises from about 5% to about 90% modified nucleotides as compared to an unmodified or naturally occurring nucleotide sequence. In some embodiments, the DNA gap domain comprises from about 5% to about 80% modified nucleotides. In some embodiments, the DNA gap domain comprises from about 5% to about 70% modified nucleotides. In some embodiments, the DNA gap domain comprises from about 5% to about 60% modified nucleotides. In some embodiments, the DNA gap domain comprises from about 5% to about 50% modified nucleotides. In some embodiments, the DNA gap domain comprises from about 5% to about 40% modified nucleotides. In some embodiments, the DNA gap domain comprises from about 5% to about 30% modified nucleotides. In some embodiments, the DNA gap domain comprises from about 5% to about 20% modified nucleotides. In some embodiments, the DNA gap domain comprises from about 5% to about 10% modified nucleotides. In some embodiments, the DNA gap domain comprises from about 5% to about 9% modified nucleotides.

In some embodiments, the DNA gap domain comprises hybrid RNA/DNA sequences of either unmodified or modified nucleotides. In some embodiments, the DNA gap domain comprises no less than about 250, 200, 150, 100, 50, 45, 40, 35, 30, 25, or 20 nucleotides, wherein no more than about 50, 45, 40, 35, 30, 25, 20, 15, 14, 13, 12, 11, 10, 9, 8, 7, 6, 5, 4, 3, 2, or 1 nucleotides is a modified or unmodified deoxyribonucleic acid. In some embodiments, the DNA gap domain comprises no less than about 250, 200, 150, 100, 50, 45, 40, 35, 30, 25, or 20 nucleotides, wherein no more than about 50, 45, 40, 35, 30, 25, 20, 15, 14, 13, 12, 11, 10, 9, 8, 7, 6, 5, 4, 3, 2, or 1 nucleotides from the 5' end of the nucleic acid sequence is a modified or unmodified deoxyribonucleic acid.

Variants of a particular nucleic acid molecule of the disclosure (i.e., the reference DNA sequence) can also be evaluated by comparison of the percent sequence identity between the nucleic acid and the variant nucleic acid molecule and the polypeptide encoded by the reference nucleic acid molecule. In some embodiments the nucleic acid sequence or molecules disclosed herein encompass variants. Percent sequence identity between any two nucleic acid molecules can be calculated using sequence alignment programs and parameters described elsewhere herein. Where any given pair of nucleic acid molecule of the disclosure is evaluated by comparison of the percent sequence identity shared by the two nucleotides such that they encode, the percent sequence identity between the two encoded nucleic acid sequence is at least about 70%, 75%, 80%, 85%, 90%, 91%, 92%, 93%, 94%, 95%, 96%, 97%, 98%, 99% or more sequence identity. In some embodiments, the term "variant" nucleotide sequence is intended to mean a nucleotide sequence derived from the native or disclosed nucleotide by deletion (so-called truncation) of one or more nucleic acid sequences at the 5' prime and 3' prime-terminal and/or terminal end of the native or disclosed nucleotide sequence; deletion and/or addition of one or more amino acids at one or more internal sites in the native or disclosed nucleotide sequence; or substitution of one or more bases or modifications at one or more sites in the native or disclosed nucleotide sequence. Variant nucleotide sequences encompassed by the present disclosure are biologically active, that is they continue to possess the desired biological activity of the disclosed nucleotide acid sequence as described herein. Such variants may result from, for example, genetic polymorphism or from human manipulation. Biologically active variants of a nucleic acid sequences of the disclosure will have at least about 70%, 75%, 80%, 85%, 90%, 91%, 92%, 93%, 94%, 95%, 96%, 97%, 98%, 99% or more sequence identity to the nucleic acid sequence for the disclosed or native protein as determined by sequence alignment programs and parameters disclosed herein. A biologically active variant of a nucleotide sequence of the disclosure may differ from the disclosed nucleotide sequence by as few as about 1, 2, 3, 4, 5, 6, 7, 8, 9, 10, 11, 12, 13, 14 or about 15 nucleobases, as few as about 1 to about 10, such as 6-10, as few as 5, as few as 4, 3, 2, or even 1 nucleobase. The nucleotide sequences of the disclosure may be altered in various ways including base substitutions, deletions, truncations, and insertions. Methods for such manipulations are generally known in the art. For example, nucleotide sequence variants and fragments of the proteins can be prepared by standard PCR-induced mutations in the nucleic acid sequence by the designing primers with the mutations to be added or deleted.

Compositions. The disclosure relates to a nucleic acid molecule or nucleic acid molecules comprising a nucleic acid sequence of two, three, four, five or more domains, each domain comprising or consisting of from about 1 to about 30 nucleic acids; wherein the first domain is an LNA domain and the second domain is a DNA gap domain and the first and second domains appear in the 5' to 3' orientation and optionally, the composition comprising from about 1% to about 100% modified nucleic acids.

In some embodiments, the composition comprises the nucleic acid sequence with a third domain which is a second LNA domain and the domains appear in the 5' to 3' orientation as LNA-DNA gap-LNA or 2'-O-methoxyethyl (2'-MOE)-DNA gap-2'-O-methoxyethyl (2'-MOE). In some embodiments, the domains are contiguous or non-contiguous with from about 1 to about 100 or more nucleotides in between one or more domains.

As a non-limiting example, compositions of the disclosure can comprise a nucleic acid sequence of N'-[Z]n-N"; wherein N' is any modified or unmodified 5' LNA or 2'-O-methoxyethyl (2'-MOE) domain; N" is any modified or unmodified 3' LNA domain; any n is any positive integer from about 1 to about 250, wherein each position of Z in the formula may have independently selected positions at their respective R1, R2, R3, and R4 subgroups. As a nonlimiting example, compositions of the disclosure relate to a nucleic acid sequence of N'-[$Z_{10}$]-N"; wherein N' is any modified or unmodified 5' terminal nucleotide; N" is any modified or unmodified 3' terminal nucleotide; wherein [$Z$]$_{10}$ is $Z_1$—$Z_2$-$Z_3$-$Z_4$-$Z_5$-$Z_6$-$Z_7$-$Z_8$-$Z_9$-$Z_{10}$] and each position of Z in the formula may have an independently selected positions at their respective R1, R2, R3, and R4 subgroups. As a another non-limiting example, compositions of the disclosure may comprise a nucleic acid sequence of N'-[Z]$_n$-N"; wherein N' is any modified or unmodified 5' terminal nucleotide; N" is any modified or unmodified 3' terminal nucleotide; any n is any positive integer from about 1 to about 100, wherein each position of Z in the sequence may have an independently selected positions at their respective R1, R2, R3, and R4 subgroups.

In some embodiments, the nucleotide binding domain or LNA or 2'-O-methoxyethyl (2'-MOE) domain consists of from about 1 to about 25 nucleotides; wherein the from 1 to about 25 nucleotides comprises a sequence similarity of about 90%, 91%, 92%, 93%, 94%, 95%, 96%, 97%, 98%, 99%, or 100% sequence homology to any target sequences identified. In some embodiments, the nucleotide binding domain or LNA or 2'-O-methoxyethyl (2'-MOE) domain consists of from about 8 to about 30 nucleotides; wherein the from about 8 to about 30 nucleotides comprises a sequence similarity of about 90%, 91%, 92%, 93%, 94%, 95%, 96%, 97%, 98%, 99%, or 100% sequence homology to any target sequence identified herein. In some embodiments, the nucleotide binding domain or a LNA or 2'-O-methoxyethyl (2'-MOE) domain consists of from about 10 to about 40 nucleotides; wherein the from about 10 to about 40 nucleotides comprises a sequence similarity of about 90%, 91%, 92%, 93%, 94%, 95%, 96%, 97%, 98%, 99%, or 100% sequence homology to any target sequence identified herein. In some embodiments, the nucleotide binding domain or a DNA-binding domain consists of from about 15 to about 25 nucleotides; wherein the from 15 to about 25 nucleotides comprises a sequence similarity of about 90%, 91%, 92%, 93%, 94%, 95%, 96%, 97%, 98%, 99%, or about 100% sequence homology to any target sequence identified herein. For instance, one of ordinary skill in art could identify other DNA-binding domains which may be structurally related to those sequences provided herein.

In some embodiments, any of the sequences disclosed herein may have a LNA or 2'-O-methoxyethyl (2'-MOE) domain and a DNA gap domain. Any of the domains of the disclosed oligonucleotides may be in any order from 5' to 3' orientation and may be contiguous as to each other or any one or multiple domains or elements may be non-contiguous in relation to one or more of the other domains, such that a different element, amino acid sequence, nucleotide or set of modified nucleotides may precede the 5' and/or 3' area of any domain.

In some embodiments, for instance, any one or combination of domains or sequences disclosed herein may comprise a sequence of about 1, 2, 3, 4, 5, 6, 7, 8, 9, 10, 15, 20, 25, 30, 35, 40, 45, or 50 or more modified or unmodified nucleotides flanking the 3' or 5' end of each domain. In some embodiments, for instance, any one or combination of domains or sequences disclosed herein may comprise a sequence of about 1, 2, 3, 4, 5, 6, 7, 8, 9, 10, 15, 20, 25, 30, 35, 40, 45, or 50 or more modified or unmodified uracils flanking the 3' or 5' end of each domain. Each domain may comprise from about 10 to about 15, 20, 25, 30, 35, 40, 45, 50, 60, 65, 70, 75, 80, 85, 90, 95, 100, 110, 120, 130, 140, 150, 160, 170, 180, 190, 200, 210, 220, 230, 240, or 250 or more modified or unmodified nucleic acids of DNA or RNA.

In some embodiments, the disclosure relates to a compositions comprising a nucleic acid sequence comprising, consisting essentially of, or consisting of a sequence that is 70%, 75%, 80%, 85%, 90%, 91%, 92%, 93%, 94%, 95%, 96%, 97%, 98%, 99% homologous to any one or combination of sequences disclosed herein, wherein the nucleic acid sequence comprises a fragment or variant of the sequences disclosed herein but possesses the same or substantially the same function as the full-length sequence disclosed herein. For example, in the case of a fragment or variant of a nucleic acid sequence disclosed herein that comprises modified nucleotides in the DNA-binding domain, in some embodiments, the variant or fragment would be functional insomuch as it would exceed or retain some or all of its capacity to bind DNA at that domain as compared to the full-length sequence.

Any of the disclosed nucleic acid sequences may comprise any one or combination or set of modifications disclosed herein. In some embodiments, the nucleic acid comprises RNA, DNA, or combinations of both RNA and DNA. In some embodiments, the nucleotide sequence, optionally in respect to one or a plurality of domains, comprises a modified nucleobase or a modified sugar.

Modifications to nucleotides are known in the art but include any of the disclosed modifications in the present application. Oligonucleotides particularly suited for the practice of one or more embodiments of the present disclosure comprise 2'-sugar modified oligonucleotides wherein one or more of the 2'-deoxy ribofuranosyl moieties of the nucleoside is modified with a halo, alkoxy, aminoalkoxy, alkyl, azido, or amino group. For example, the substitutions which may be independently selected from F, CN, CF3, OCF3, OCN, O-alkyl, S-alkyl, SMe, SO2Me, ONO2, NO2, NH3, NH2, NH-alkyl, OCH3=CH2 and OCCH. In each of these, alkyl is a straight or branched chain of C1 to C20, having unsaturation within the carbon chain. A preferred alkyl group is C1-C9 alkyl. A further preferred alkyl group is C5-C20 alkyl. In some embodiments, any of the nucleotide sequences disclosed herein may be modified with a 2'-O-methyl (2'-O-Me) modification, 2'O-methylphosphorothioate (2'OMePS) modification, a phosphorodiamidate morpholino (PMO) modification, a 2'methoxyethoxy (2'-MOE) modification, a vivo-morpholino (vPMO) modification, a peptide conjugate, a peptide nucleic acid (PNA), and LNA. In some embodiments, the nucleotide sequence further comprises from about 1% to about 99% modified nucleotides chosen from: 2'-O-methyl (2'-O-Me) modification, a 2'O methylphosphorothioate (2'OMePS) modification, a phosphorodiamidate morpholino (PMO) modification, a 2'methoxyethoxy (2'-MOE) modification, a vivo-morpholino (vPMO) modification, a peptide conjugate, a peptide nucleic acid (PNA), and LNA.

In further embodiments of the present disclosure, the individual nucleotides of the oligonucleotides of the disclosure are connected via phosphorus linkages. Phosphorus linkages include phosphodiester, phosphorothioate and phosphorodithioate linkages. In one preferred embodiment of this disclosure, nuclease resistance is conferred on the oligonucleotides by utilizing phosphorothioate internucleoside linkages.

In further embodiments of the disclosure, nucleosides can be joined via linkages that substitute for the internucleoside phosphate linkage. Macromolecules of this type have been identified as oligonucleosides. The term "oligonucleoside" thus refers to a plurality of nucleoside units joined by non-phosphorus linkages. In such oligonucleosides the linkages include an —O—CH2-CH2-O— linkage (i.e., an ethylene glycol linkage) as well as other novel linkages disclosed in U.S. Pat. No. 5,223,618, issued Jun. 29, 1993, U.S. Pat. No. 5,378,825, issued Jan. 3, 1995 and U.S. patent application Ser. No. 08/395,168, filed Feb. 27, 1995. Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. No. 5,138,045, issued Aug. 11, 1992, all of which are herein incorporated by reference in their entireties.

In some embodiments, a nucleic acid sequence is selected to reduce the degree of secondary structure within the nucleic sequence. Secondary structure may be determined by any suitable polynucleotide folding algorithm. Some programs are based on calculating the minimal Gibbs free energy. An example of one such algorithm is mFold, as described by Zuker and Stiegler (NUCLEIC ACIDS RES. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, CELL 106(1): 23-24; and PA Carr and GM Church, 2009, Nature Biotechnology 27(12): 1151-62). Further algorithms may be found in U.S. application Ser. No. 61/836,080 filed Jun. 17, 2013 (Broad Reference BI-2013/004A); incorporated herein by reference in its entirety.

In another embodiment, the disclosure provides a cell or a vector comprising one of the nucleic acids of the disclosure or functional fragments thereof. The cell may be an animal cell or a plant cell. In some embodiments, the cell is a mammalian cell, such as a human cell. In one aspect, the disclosure provides a vector system comprising one or more vectors. In some embodiments, the system comprises: (a) a synthetic nucleic acid sequence comprising at least one of the nucleic acid sequences disclosed herein, wherein the nucleic acid sequence directs sequence-specific portion of the DNA gap domain to a target sequence in a eukaryotic cell. In general, and throughout this specification, the term "vector" refers to a nucleic acid molecule capable of transporting another nucleic acid to which it has been linked. Vectors include, but are not limited to, nucleic acid molecules that are single stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell.

Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as expression vectors." Common expression vectors of utility in recombinant DNA techniques are often in the form of plasmids.

Another aspect of the disclosure relates to a composition comprising a nucleic acid disclosed herein and one or a plurality of recombinant expression vectors. Generally, the disclosure relates to composition comprising a synthetic nucleic acid sequence and one or a plurality of recombinant expression vectors. Recombinant expression vectors can comprise a nucleic acid of the disclosure in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences).

Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue specific promoter may direct expression primarily in a desired tissue of interest, such as a cell of the respiratory system, muscle, neuron, bone, skin, blood, specific organs (e.g. liver, pancreas), or particular cell types (e.g. lymphocytes). Regulatory elements may also direct expression in a temporal dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, CELL, 41:521-530 (1985)), the SV40 promoter, the dihydrofolate reductase promoter, the beta-actin promoter, the phosphoglycerol kinase (PGK) promoter, and the EFla promoter. Also encompassed by the term "regulatory element" are enhancer elements, such as WPRE; CMV enhancers; the R-U5' segment in LTR of HTLV-1 (Mol. Cell. Biol., Vol. 8(1), p. 466-472, 1988); SV40 enhancer; and the intron sequence between exons 2 and 3 of rabbit 3-globin (PROC. NATL. ACAD. SCI. USA., Vol. 78(3), p. 1527-31, 1981). It will be appreciated by those skilled in the art that the design of the expression vector can depend on such factors as the choice of the host cell to be transformed, the level of expression desired, etc. One or more nucleic acid sequences and one or more vectors can be introduced into host cells to form complexes with other cellular or non-natural compounds, produce transcripts, proteins, or peptides, including fusion proteins or peptides, encoded by nucleic acids as described herein.

The disclosure also relates to pharmaceutical compositions comprising: (i) one or nucleic acid sequences disclosed herein or one or more pharmaceutically acceptable salts thereof; and (ii) a pharmaceutically acceptable carrier.

The term "pharmaceutically acceptable salts" refers to physiologically and pharmaceutically acceptable salts of the nucleic acid sequences of the disclosure: i. e., salts that retain the desired biological activity of the nucleic acid sequences and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., *Pharmaceutical Salts*, J. PHARM SCI., 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present disclosure. As used herein, a "pharmaceutical addition salt" includes a pharmaceutically acceptable salt of an acid form of one of the components of the compositions of the disclosure. These include organic or inorganic acid salts of the amines. In some embodiments, a pharmaceutically acceptable salt is selected from one or a combination of hydrochlorides, acetates, salicylates, nitrates and phosphates.

Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfa or phospho acids or N-substituted sulfamic acids; for example acetic acid, propionic acid, glycolic acid, succinic acid, malefic acid, hydroxymaleic acid, methylmaleic acid, fiunaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, malefic acid, fumaric acid, glucoruc acid, citric acid, malic acid, ascorbic acid, benzoic acid, tannic acid, palimitic acid, alginic acid, polyglutamic acid, naphthalenesulfonic acid, methanesulfonic acid, p-toluenesulfonic acid, naphthalenedisulfonic acid, polygaiacturonic acid, and the like; and (d) salts formed from elemental anions such as chlorine, bromine, and iodine.

The practice of the present disclosure employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)), all of which are incorporated by reference in their entireties. In some embodiments, the nucleic acid sequence comprises one or a plurality of radioactive moieties. Radioactive moiety means a substituent or component of a compound that comprises at least one radioisotope. Any radioisotope may be used. In some embodiments, the radioisotope is selected from Table 2. In some embodiments, the substituent or component of a compound of the present invention may incorporate any one, two, three, or more radioisotopes disclosed in the following table.

administered to the subject before, contemporaneously with, substantially contemporaneously with, or after administration of the pharmaceutical composition.

Compositions of the disclosure include pharmaceutical compositions comprising: a particle comprising any of the nucleic acid sequences disclosed herein, or pharmaceutically acceptable salts thereof: and a pharmaceutically acceptable carrier. In some embodiments, the pharmaceutically acceptable carrier is distilled water or saline. In preferred embodiments, the pharmaceutically acceptable carrier is free of RNase/DNase.

As used herein, a "particle" refers to any entity having a diameter of less than 100 microns (µm). Typically, particles have a longest dimension (e.g. diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. In some embodiments, a population of particles may be relatively uniform in terms of size, shape, and/or composition. In general, inventive particles are biodegradable and/or biocompatible.

Inventive particles can be solid or hollow and can comprise one or more layers. In some embodiments, particles are spheres, spheroids, flat, plate-shaped, cubes, cuboids, ovals, ellipses, cylinders, cones, or pyramids. In some embodiments, particles can be a matrix of polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step. In some embodiments, particles can be a non-polymeric particle (e.g. a metal particle, quantum dot, ceramic, inorganic material, bone, etc.). Components of the pharmaceutical compositions disclosed herein may comprise particles or may be microparticles, nanoparticles, liposomes, and/or micelles comprising one or more disclosed nucleic acid sequences or conjugated to one or more disclosed amino acids. As used herein, the term "nanoparticle" refers to any particle having a diameter of less than 1000 nm. Examples of nanoparticles are disclosed in NATURE BIOTECHNOLOGY 31, 638-646, which is herein incorporated by reference in its entirety. In some embodiments, the particle is an exosome.

Pharmaceutical "carrier" or "excipient", as used herein, includes any and all solvents, dispersion media, diluents, or

TABLE 2

Radioisotopes that may be incorporated into pharmaceutical compositions $^{2}$H, $^{3}$H, $^{13}$C, $^{14}$C, $^{15}$N, $^{16}$O, $^{17}$O, $^{31}$P, $^{32}$P, $^{35}$S, $^{18}$F, $^{36}$Cl, $^{225}$Ac, $^{227}$Ac, $^{212}$Bi, $^{213}$Bi, $^{109}$Cd, $^{60}$Co, $^{64}$Cu, $^{67}$Cu, $^{166}$Dy, $^{169}$Er, $^{152}$Eu, $^{154}$Eu, $^{153}$Gd, $^{198}$Au, $^{166}$Ho, $^{125}$I, $^{133}$I, $^{192}$Ir, $^{177}$Lu, $^{99}$Mo, $^{194}$Os, $^{103}$Pd, $^{195m}$Pt, $^{32}$P, $^{33}$P, $^{223}$Ra, $^{186}$Re, $^{188}$Re, $^{103}$Rh, $^{145}$Sm, $^{153}$Sm, $^{47}$Sc, $^{75}$Se, $^{85}$Sr, $^{89}$Sr, $^{99m}$Tc, $^{228}$Th, $^{229}$Th, $^{170}$Tm, $^{117m}$Sn, $^{188}$W, $^{127}$Xe, $^{175}$Yb, $^{90}$Y, $^{91}$Y In some embodiments, the composition or pharmaceutical composition comprises any nucleic acid disclosed herein or its salt and one or more additional therapies, including but not limited to a corticosteroid, an anticonvulsant, an immunosuppressant, an antibiotic, an angiotensin-converting enzyme (ACE) inhibitor, and a beta blocker. In some embodiments, the pharmaceutical composition comprises any one or plurality of nucleic acids disclosed herein or its salt or variant thereof and/or one or more therapies is administered to the subject before, contemporaneously with, substantially contemporaneously with, or after administration of the pharmaceutical composition.

other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof.

Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient or carrier is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation exchange resins, calcium carbonate, silicates, sodium carbonate, cross-linked poly(vinyl pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In some embodiments, the pharmaceutical composition comprise any one or combination of nucleic acid sequence disclosed here fused, linked or conjugated to a peptide from about 6, 10, 20, 50 to about 100 amino acids long. In some embodiments, the pharmaceutical composition comprises a therapeutically effective amount of a gapmer as disclosed herein fused to a protein or peptide that is an exosome targeting domain. The exosome targeting domain comprises an amino acid sequence capable of binding or associating to a receptor on an exosome.

Compositions of the disclosure relate to LNA gapmers or other gapmers disclosed herein bound to exosome via an exosome targeting domain which is a nucleic acid sequence, amino acid sequence, or nucleic acid-amino acid fusion. In some embodiments, the composition comprises a nucleic acid sequence fused to a ligand. The ligand of the fusion typically is a heterologous amino acid sequence (i.e., relative to the engineered glycosylation site and/or relative to the exosome-targeting domain) that binds to a receptor present on the surface of a target cell (e.g., a protein receptor, a carbohydrate receptor, or a lipid receptor present on the surface of a cell). For example, suitable ligands may include a ligand for a cell receptor present on a target cell, or an antibody or binding fragment thereof that binds to a cell receptor or other membrane protein present on a target cell.

Methods of Making Compositions and Modifications. Modified oligonucleotides may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite triester with an oxidizing or sulfurizing agent), and capping (acetylation of unreacted 5'-hydroxy 1 groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exchange resin. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3 '-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneiminoand methylenehydrazino backbones; sulfonate and sulfonamide backbones; amide backbones; and others having mixed N, O, S and $CH_2$ component parts. Any of the oligonucleotide backbone modifications here may replace any one of the internucleotide linkages set forth in any of the disclosed nucleotide sequences.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., SCIENCE, 1991, 254, 1497-1500.

Some embodiments of the disclosure are oligonucleotides with phosphorothioate backbones and oligonucleosides with heteroatom backbones, and in particular —CH2-NH—O—CH2-, —CH2-N(CH3)-O—CH2-[known as a methylene (methylimino) or MMI backbone], —CH2-O—N(CH3)-CH2-, -CH2-N(CH3)-N(CH3)-CH2- and —O—N(CH3)-CH2-CH2-[wherein the native phosphodiester backbone is represented as —O—P—O—CH2-] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. In some embodiments, oligonucleotides of the disclosure comprise one of the following at the 2' position: OH; F; O- , S- , or N-alkyl; O- , S- , or N-alkenyl; O- , S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH2)nO]mCH3, O(CH2)nOCH3, O(CH2)nNH2, O(CH2)nCH3, O(CH2)nONH2, and OCH2nON[(CH2)nCH3)$_2$, where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, acetamide, substituted silyl, an RNA cleaving group, a reporter group, an intercalator, a group for improving the pharmacokinetic properties of an oligonucleotide, or a group for improving the pharmacodynamics properties of an oligonucleotide, and other substituents having similar properties. A preferred modification includes 2'-methoxyethoxy (2'-O—CH2CH2OCH3, also known as 2'-O-(2-methoxyethyl) or 2'-MOE) (Martin et al., HELV. CHIM. ACTA, 1995, 78, 486-504) i.e., an alkoxyalkoxy group.

Another modification includes 2'-dimethylaminooxyethoxy, i.e., a O(CH2)2ON(CH3)$_2$ group, also known as 2'-DMAOE, and 2'-dimethylamino-ethoxyethyl (2'-DMAEOE), i.e., 2'-OCH2-O—CH2-N(CH2)$_2$. In some embodiments, the disclosure relates to a pharmaceutical composition comprising an effective amount of a nucleotide sequence comprising: (i) an RNA-binding domain from about 5 to about 30 nucleotides complementary to a region of a SARS-CoV-2 RNA; and (ii) at least one locked nucleic acid (LNA) or 2'-O-methoxyethyl (2'-MOE) domain comprising from about 1 to about 5 nucleotides; and/or at least one 2'MOE domain comprising from about 1 to about 10 nucleotides, or a salt thereof. In some embodiments, the disclosure relates to a pharmaceutical composition comprising an effective amount of a nucleotide sequence comprising: (i) an RNA-binding domain from about 5 to about 30 nucleotides complementary to a region of a SARS-CoV-2 RNA; and (ii) at least one 2'MOE domain comprising from about 1 to about 10 nucleotides, or a salt thereof. In some embodiments, the disclosure relates to a pharmaceutical composition comprising an effective amount of a nucleotide sequence comprising: (i) an RNA-binding domain from about 5 to about 30 nucleotides complementary to a region of a SARS-CoV-2 RNA and (ii) at least one 2'MOE domain comprising from about 1 to about 10 nucleotides, or a salt thereof.

Other modifications include 2'-methoxy(2'-OCH3), 2'-aminopropoxy (2'OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide.

Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include a modified thioester group on the 2', 3' and/or 5' nucleoside. Such modifications in the 5' carbon of the ribose sugar also for formation of single 5'-S-thioester linkages between nucleotides in a synthetic nucleotide sequence. In any 3' or 5' linkage between nucleotides any one or both positions may create a series of linkages between nucleotides. The linkages at the 2' or 3' can create thioester bond, phosphorothioriate linkages between two or a plurality of nucleosides in the oligonucleotide.

Strategically placed sulfur atoms in the backbone of nucleic acids have found widespread utility in probing of specific interactions of proteins, enzymes and metals. Sulfur replacement for oxygen may be carried out at the 2'-position of RNA and in the 3'-5' position of RNA and of DNA. Polyribonucleotide containing phosphorothioate linkages were obtained as early as 1967 by Eckstein et al. using DNA-dependent RNA polymerase from *E. coli*. DNA-dependent RNA polymerase is a complex enzyme whose essential function is to transcribe the base sequence in a segment of DNA into a complementary base sequence of a messenger RNA molecule. Nucleoside triphosphates are the substrates that serve as the nucleotide units in RNA. In the polymerization of triphosphates, the enzyme requires a DNA segment that serves as a template for the base sequence in the newly synthesized RN A. In the original procedure, Uridine 5'-0-(1-thiotriphosphate), adenosine 5' O-triphosphate, and only d (AT) as a template was used. As a result, an alternating copolymer is obtained, in which every other phosphate is replaced by a phosphorothioate group. Using the same approach and uridine 5'-0-(1-thiotriphosphate) and adenosine 5'-0-(1-thiotriphosphate), polyribonucleotide containing an all phosphorothioate backbone can also synthesized.

In both cases, nucleoside 5'-0-(1-thiotriphosphates) as a mixture of two diastereomers can be used. In some embodiments, alternating phosphorothioate groups link a DNA or RNA or hybrid sequence of predominantly RNA to form alternating phosphorothioate backbones. Optionally, linkers of any cyclic or acyclic hydrocarbon chains of varying length may be incorporated into the nucleic acid. In some embodiments, linkers of the disclosure comprise one or a plurality of: branched or non-branched alkyl, hydroakyl, hydroxyl, halogen, metal, nitrogen, or other atoms.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941, and 5,750,692, each of which is herein incorporated by reference in its entirety.

In some embodiments, the nucleic acids is conjugated to other proteins, polypeptides or molecules. Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

It is not necessary for all positions in a given compound to be uniformly modified, and in fact more than one of the aforementioned modifications may be incorporated in a single sequence or compound or even at a single nucleoside or functional group within one or a plurality of positions within a nucleoside or an oligonucleotide.

For example, GalNAc-conjugated modification are known to direct oligonucleotides to liver cells. Modifications, such as GalNAc-conjugated modification, may be made to any one or combination of oligonucleotides disclosed herein with automated solid phase synthesis, similar to the solid phase synthesis that produced unconjugated oligonucleotides.

During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example in U.S. Pat. No. 8,106,022, which is herein incorporated by reference in its entirety for the description of the synthesis of carbohydrate-containing conjugates, including conjugates comprising one or more GalNAc moieties, and of the synthesis of conjugate covalently linked to solid support.

The disclosure also relates to synthesizing one or a plurality of oligonucleotides, such as LNA-DNA chimeric molecules. 2'-deoxy-2'-modified nucleosides of adenine, guanine, cytosine, thymidine and certain analogs of these nucleobases may be prepared and incorporated into oligonucleotides via solid phase nucleic acid synthesis. Novel oligonucleotides can be assayed for their hybridization properties and their ability to resist degradation by nucleases compared to the unmodified oligonucleotides. Initially, small electronegative atoms or groups can be selected because they would not be expected to sterically interfere with required Watson-Crick base pair hydrogen bonding (hybridization). However, electronic changes due to the electronegativity of the atom or group in the 2' position may profoundly affect the sugar conformation.

2'-Substituted oligonucleotides can be synthesized by standard solid phase nucleic acid synthesis using an automated synthesizer such as Model 380B (Perkin Elmer/Applied Biosystems) or MilliGen/Biosearch 7500 or 8800. Triester, phosphoramidite, or hydrogen phosphonate coupling chemistries [Oligonucleotides. Antisense Inhibitors of Gene Expression. M. Caruthers, p. 7, J. S. Cohen (Ed.), CRC Press, Boca Raton, Fla., 1989] are used with these synthesizers to provide the desired oligonucleotides. The Beaucage reagent [J. AMER. CHEM. SOC., 112, 1253 (1990)] or elemental sulfur [Beaucage et al., TET. LETT., 22, 1859 (1981)] is used with phosphoramidite or hydrogen phosphonate chemistries to provide 2'-substituted phosphorothioate oligonucleotides.

2'-substituted nucleosides (A, G, C, T(U), and other modified nucleobases) may be prepared by modification of several literature procedures as described below.

Procedure 1. Nucleophilic Displacement of 2'-Leaving Group in Arabinopurine nucleosides. Nucleophilic displacement of a leaving group in the 2'-up position (2' deoxy-2'-(leaving group)arabino sugar) of adenine or guanine or their analog nucleosides. General synthetic procedures of this type have been described by Ikehara et al., TETRAHEDRON, 34, 1133 (1978); ibid., 31, 1369 (1975); CHEMISTRY AND PHARMACEUTICAL BULLETIN, 26, 2449 (1978); ibid., 26, 240 (1978); Ikehara, ACCOUNTS OF CHEMICAL RESEARCH, 2, 47 (1969); and Ranganathan, TETRAHEDRON LETTERS, 15, 1291 (1977).

Procedure 2. Nucleophilic displacement of 2,2'-Anhydropyrimidines. Nucleosides thymine, uracil, cytosine or their analogs are converted to 2'-substituted nucleosides by the intermediacy of 2,2'-cycloanhydro nucleoside as described by Fox et al., JOURNAL OF ORGANIC CHEMISTRY, 29, 558 (1964).

Procedure 3. 2'-Coupling Reactions. Appropriately 3',5'-sugar and base protected purine and pyrimidine nucleosides having a unprotected 2'-hydroxyl group are coupled with electrophilic reagents such as methyl iodide and diazomethane to provide the mixed sequences containing a 2'-OMe group H. Inoue et al., NUCLEIC ACIDS RESEARCH, 15, 6131.

Procedure 4. 2-Deoxy-2-substituted Ribosylations. 2-Substituted-2-deoxyribosylation of the appropriately protected nucleic acid bases and nucleic acids base analogs has been reported by Jarvi et al., NUCLEOSIDES & NUCLEOTIDES, 8, 1111-1114 (1989) and Hertel et al., JOURNAL OF ORGANIC CHEMISTRY, 53, 2406 (1988).

In some embodiments, the presence of the nucleic acid molecule comprising a chimeric set of nucleic acid sequences comprising the following structure: gapmer domain 1-DNA gap-gapmer domain 2, wherein the first gapmer domain is positioned at the flank of the nucleic acid molecule and the second gapmer domain is positioned at the opposing flank of the nucleic acid molecule and one of the two domains comprises a sequence that associates with an coronavirus RNA sequence in a cell) and the other domain comprises a sequence that associates with an amino acid that is expressed by a target cell, such as a respiratory epithelial cell.

Methods. The disclosure relates to treating coronavirus-related disease, disorder or condition in an subject in need thereof comprising administering a therapeutically effective amount of a composition or pharmaceutical composition disclosed herein. In certain embodiments, the disclosure relates to methods of SARS-CoV-2 related disease, disorders or conditions. In some embodiments, the method of treating further comprises repeating the step of administering the composition or pharmaceutical composition once a day, once every other day, once a week, once every other week or once a month.

The term "administering" or "administration" and the like, refers to providing one or a plurality of compositions or nucleic acids of the disclosure to the subject in need of treatment. Preferably the subject is a mammal, such as a human. The present disclosure also relates to administering one or a plurality of the compositions of nucleic acids of the disclosure in conjunction with a second composition, such as an antiviral drug or agent including drugs that prevent, reduce or ameliorate cytokine storm. In some embodiments, the composition or pharmaceutical composition and the one or more of an antiviral drug or agent are synergistic. When one or a plurality of the compositions or nucleic acids of the disclosure are administered in conjunction with a second composition, the one or a plurality of the compositions of nucleic acids in the disclosure and the second composition can be administered simultaneously in the same composition, simultaneously in different dosage forms or sequentially or at different times. When the one or a plurality of compositions of nucleic acids of the disclosure and the second composition are administered at the same time, they can be administered as a single composition or pharmaceutical composition or they can be administered as separate pharmaceutical compositions. It is understood that when one or a plurality of the compositions of nucleic acids of the disclosure are administered, one or a plurality of the compositions of nucleic acids of the disclosure can be administered in conjunction with a second composition, that the active agents can be administered in a single combination or in multiple combinations. For example, when administered intravenously, the one or a plurality of the compositions of nucleic acids in the disclosure can be dissolved or suspended in any of the commonly used intravenous fluids and administered by infusion, and then a second composition can be dissolved or suspended in any of the commonly used intravenous fluids and administered by infusion. Conversely, the second composition can be dissolved or suspended in any of the commonly used intravenous fluids and administered by infusion, and then one or a plurality of compositions of nucleic acids of the disclosure can be dissolved or suspended in any of the commonly used intravenous fluids and administered by infusion. Alternatively, a pharmaceutical composition comprising one or a plurality of the compositions of nucleic acids in the disclosure and a second composition can be dissolved or suspended in any of the commonly used intravenous fluids and administered by infusion.

In some embodiments, the pharmaceutical composition is administered in a liposomal formulation. In some embodiments, toxicity to other cells is prevented or reduced, such that toxic doses are tolerated in the subject.

In some embodiments, administration of the effective amount of pharmaceutical composition disclosed herein is not limited to any particular delivery system and includes, without limitation, parenteral (including subcutaneous, intravenous, intramedullary, intraarticular, intramuscular, or intraperitoneal injection), rectal, topical, transdermal, mucosal or oral (for example, in capsules, suspensions, or tablets) administration. In some embodiments, administration to a subject in need thereof occurs in a single dose or in repeat administrations, and in any of a variety of physiologically acceptable salt forms, or with an acceptable pharmaceutical carrier or additive as part of a pharmaceutical composition. In some embodiments, any suitable and physiological acceptable salt forms or standard pharmaceutical formulation techniques, dosages, and excipients are utilized. In some embodiments, the step of administering comprises administering the composition or pharmaceutical composition intravenously, intramuscularly, topically, intradermally, intramucosally, subcutaneously, sub lingually, orally, intra vaginally, intracavernously, intraocularly, intranasally, intrarectally, gastrointestinally, intraductally, intrathecally, subdurally, extradurally, intraventricular, intrapulmonary, into an abscess or focus of viral infection, intra articularly, into a bursa, subpericardially, into an axilla, intrauterine, into the pleural space, intraperitoneally, transmucosally, or transdermally.

Since the SARS-CoV-2 infects the respiratory system and can affect additional organs, gapmer AOs are ideal since it can be safely delivered via either tracheal or systemic routes.

In some embodiments, effective dosages achieved in one animal are extrapolated for use in another animal, including humans, using conversion factors known in the art.

In some embodiments, the pharmaceutical composition dosing amount or schedule follows clinically approved, or experimental, guidelines. In some embodiments, the dose of the pharmaceutical composition is about 1, 2, 3, 4, 5, 6, 7, 8, 9, 10, 15, 20, 25, 30, 40, 50, 60, 70, 80, 90, 100, 125, 150, 175, 200, 225, 250 or about 500 mg/kg of the subject per day.

In some embodiments the pharmaceutical composition is administered to the individual in about I, 2, 3, 4, 5 daily doses over 5 consecutive or non-consecutive days. In some embodiments, the oligonucleotide is administered to the individual in about 1, 2, 3, 4, 5, 6, or 7 daily doses over a single week (7 days). In some embodiments, the pharmaceutical composition is administered to the individual in about 1, 2, 3, 4, 5, 6, 7, 8, 9, 10, 11, 12, 13, or 14 daily doses over 14 days. In some embodiments, the pharmaceutical composition is administered to the individual in 1, 2, 3, 4, 5, 6, 7, 8, 9, 10, 11, 12, 13, 14, 15, 16, 17, 18, 19, 20, or 21 daily doses over 21 days. In some embodiments, the pharmaceutical composition is administered to the individual in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In some embodiments, the pharmaceutical composition is provided about twice a week of a 21 or a 28 day cycle. In particular embodiments, the pharmaceutical composition is provided on about days 1, 4, 8, 11, 15 and 18 of a 21 day or 28 day cycle.

In some embodiments the pharmaceutical composition is administered for: about 2 weeks (total 14 days); about 1 week with 1 week off (total 14 days); about 3 consecutive weeks (total 21 days); about 2 weeks with 1 week off (total 21 days); about I week with 2 weeks off (total 21 days); about 4 consecutive weeks (total 28 days); about 3 consecutive weeks with 1 week off (total 28 days); about 2 weeks with 2 weeks off (total 28 days); about 1 week with 3 consecutive weeks off (total 28 days).

In some embodiments the pharmaceutical composition disclosed herein is administered on day 1 of a 7, 14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. In some embodiments, the pharmaceutical composition is administered once every 1, 2, 3, 4, 5, 6, 7, or 8 weeks. In some embodiments, the pharmaceutical composition (and optionally a combination therapy) is administered for 1, 2, 3, 4, 5, 6, 7, 8, 9, IO, I 1, or 12 cycles.

The disclosure also relates to a method of modulating or inhibiting expression of SARS-CoV-2 RNA in a subject, the method comprising administering to the subject one or a combination of compositions or pharmaceutical compositions disclosed herein. In some embodiments, the subject is suffering from or suspected of having COVID-19 in other embodiments the subject may be suspected or carrying the SARS-CoV-2 virus either asymptomatically or symptomatically.

The disclosure also relates to a method of targeting a SARS-CoV-2 mRNA in a cell, for example in a respiratory system epithelial cell, the method comprising contacting one or a combination of the compositions and/or pharmaceutical compositions disclosed herein with the cell. In some embodiments, the cell is in a human subject and the step of contacting is performed by administering to the human subject a therapeutically effective amount of the composition or pharmaceutical composition disclosed herein.

According to one aspect, a method of altering a human cell is provided including transfecting the human cell with a nucleic acid disclosed herein with a DNA gap sequence sufficiently complementary to mRNA of the cell such that the DNA gap domain hybridizes to the mRNA target sequence of the human cell and degrades the mRNA, thereby reducing expression of the one or plurality of mRNA target sequences. According to one aspect, the RNA includes between about 10 to about 250 nucleotides. According to one aspect, the RNA includes between about 20 to about 100 nucleotides. The step of transfecting a nucleic acid encoding an RNA may be added to any method disclosed herein so that there is sequential or concurrent transfection of one or a plurality of vectors that carry one or more expressible genes operably linked to a regulatory sequence active in the target cell.

The disclosure also relates to a composition comprising a cell with any one or combination of nucleic acid sequences disclosed herein. In some embodiments, the cell is a plant, insect or mammalian cell. In some embodiments, the cell is a eukaryotic cell or a prokaryotic cell. The cell may be isolated from the body, a component of a culture system, or part of an organism in an in vivo based assay or therapy. The construct(s) containing the nucleic acids can be delivered to a cell using, for example, biolistic bombardment, electrostatic potential or through transformation permeability reagents (reagents known to increase the permeability of the cell wall or cell membrane). Alternatively, the system components can be delivered using *Agrobacterium*-mediated transformation, insect vectors, grafting, or DNA abrasion, according to methods that are standard in the art, including those described herein. In some embodiments, the system components can be delivered in a viral vector (e.g., a vector from a DNA virus such as, without limitation, geminivirus, AAV, adenovirus, lentiviral strains attenuated for human use, bean yellow dwarf virus, wheat dwarf virus, tomato leaf curl virus, maize streak virus, tobacco leaf curl virus, tomato golden mosaic virus, or Faba bean necrotic yellow virus, or a vector from an RNA virus such as, without limitation, a tobravirus (e.g., tobacco rattle virus, tobacco mosaic virus), potato virus X, or barley stripe mosaic virus.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of" when used in the claims, shall have its ordinary meaning as used in the field of patent law.

Any and all journal articles, patent applications, issued patents, or other cited references disclosed herein are incorporated by reference in their respective entireties.

Table 1 is provided on the following pages.

| | |
|---|---|
| SEQ ID NO: 1 | TCCCAGGTAACAAACCAACC |
| SEQ ID NO: 2 | CCCAGGTAACAAACCAACCA |
| SEQ ID NO: 3 | CTTACGGTTTCGTCCGTGTT |
| SEQ ID NO: 4 | TTACGGTTTCGTCCGTGTTG |
| SEQ ID NO: 5 | TTTCGTCCGGGTGTGACCGA |
| SEQ ID NO: 6 | TTCGTCCGGGTGTGACCGAA |
| SEQ ID NO: 7 | TCGTCCGGGTGTGACCGAAA |
| SEQ ID NO: 8 | CCTTGTCCCTGGTTTCAACG |
| SEQ ID NO: 9 | CTTGTCCCTGGTTTCAACGA |
| SEQ ID NO: 10 | TTGTCCCTGGTTTCAACGAG |
| SEQ ID NO: 11 | TGTCCCTGGTTTCAACGAGA |
| SEQ ID NO: 12 | GTCCCTGGTTTCAACGAGAA |
| SEQ ID NO: 13 | CAACGAGAAAACACACGTCC |
| SEQ ID NO: 14 | CGAGAAAACACACGTCCAAC |
| SEQ ID NO: 15 | CACACGTCCAACTCAGTTTG |
| SEQ ID NO: 16 | TGGTGTCCTTGTCCCTCATG |
| SEQ ID NO: 17 | GGTGTCCTTGTCCCTCATGT |
| SEQ ID NO: 18 | GTGTCCTTGTCCCTCATGTG |
| SEQ ID NO: 19 | TGTCCTTGTCCCTCATGTGG |
| SEQ ID NO: 20 | GTCCTTGTCCCTCATGTGGG |
| SEQ ID NO: 21 | CACCTTCAATGGGGAATGTC |
| SEQ ID NO: 22 | ACCTTCAATGGGGAATGTCC |
| SEQ ID NO: 23 | CCTTCAATGGGGAATGTCCA |

| SEQ ID NO: 24 | CAAATTGTTGAATCCTGTGG |
| SEQ ID NO: 25 | TAGAGGGAGAAACACTTCCC |
| SEQ ID NO: 26 | AGAGGGAGAAACACTTCCCA |
| SEQ ID NO: 27 | GAGGGAGAAACACTTCCCAC |
| SEQ ID NO: 28 | AGGGAGAAACACTTCCCACA |
| SEQ ID NO: 29 | GGGAGAAACACTTCCCACAG |
| SEQ ID NO: 30 | GGAGAAACACTTCCCACAGA |
| SEQ ID NO: 31 | CTTTCTACCCTCCAGATGAG |
| SEQ ID NO: 32 | TTTCTACCCTCCAGATGAGG |
| SEQ ID NO: 33 | TTCTACCCTCCAGATGAGGA |
| SEQ ID NO: 34 | TCTACCCTCCAGATGAGGAT |
| SEQ ID NO: 35 | CTACCCTCCAGATGAGGATG |
| SEQ ID NO: 36 | TACCCTCCAGATGAGGATGA |
| SEQ ID NO: 37 | ACCCTCCAGATGAGGATGAA |
| SEQ ID NO: 38 | CCCTCCAGATGAGGATGAAG |
| SEQ ID NO: 39 | TGGACCACTTAAAGTGGGTG |
| SEQ ID NO: 40 | GGACCACTTAAAGTGGGTGG |
| SEQ ID NO: 41 | GACCACTTAAAGTGGGTGGT |
| SEQ ID NO: 42 | CACTTACCCGGGTCAGGGTT |
| SEQ ID NO: 43 | ACTTACCCGGGTCAGGGTTT |
| SEQ ID NO: 44 | CTTACCCGGGTCAGGGTTTA |
| SEQ ID NO: 45 | TTACCCGGGTCAGGGTTTAA |
| SEQ ID NO: 46 | TACCCGGGTCAGGGTTTAAA |
| SEQ ID NO: 47 | ACCCGGGTCAGGGTTTAAAT |
| SEQ ID NO: 48 | CCCGGGTCAGGGTTTAAATG |
| SEQ ID NO: 49 | CCGGGTCAGGGTTTAAATGG |
| SEQ ID NO: 50 | CGGGTCAGGGTTTAAATGGT |
| SEQ ID NO: 51 | TACACTAGTAATCCTACCAC |
| SEQ ID NO: 52 | ACACTAGTAATCCTACCACA |
| SEQ ID NO: 53 | CACTAGTAATCCTACCACAT |
| SEQ ID NO: 54 | CTAGTAATCCTACCACATTC |
| SEQ ID NO: 55 | TAGTAATCCTACCACATTCC |
| SEQ ID NO: 56 | AGTAATCCTACCACATTCCA |
| SEQ ID NO: 57 | GTAATCCTACCACATTCCAC |
| SEQ ID NO: 58 | TAATCCTACCACATTCCACC |
| SEQ ID NO: 59 | AATCCTACCACATTCCACCT |
| SEQ ID NO: 60 | ATCCTACCACATTCCACCTA |
| SEQ ID NO: 61 | TCCTACCACATTCCACCTAG |
| SEQ ID NO: 62 | CCTACCACATTCCACCTAGA |
| SEQ ID NO: 63 | CTACCACATTCCACCTAGAT |
| SEQ ID NO: 64 | TACCACATTCCACCTAGATG |
| SEQ ID NO: 65 | ACCACATTCCACCTAGATGG |
| SEQ ID NO: 66 | CCACATTCCACCTAGATGGT |
| SEQ ID NO: 67 | CACATTCCACCTAGATGGTG |
| SEQ ID NO: 68 | CAGATACCTTGTACGTGTGG |
| SEQ ID NO: 69 | CTAGTACAACAGGAGTCACC |
| SEQ ID NO: 70 | ATCCTACCATACAGAAAGAC |
| SEQ ID NO: 71 | TCCTACCATACAGAAAGACG |
| SEQ ID NO: 72 | CCTACCATACAGAAAGACGT |
| SEQ ID NO: 73 | CTACCATACAGAAAGACGTT |
| SEQ ID NO: 74 | TACCATACAGAAAGACGTTC |
| SEQ ID NO: 75 | ACCATACAGAAAGACGTTCT |
| SEQ ID NO: 76 | CCATACAGAAAGACGTTCTT |
| SEQ ID NO: 77 | CTACCGAAGTTGTAGGAGAC |
| SEQ ID NO: 78 | CTATTTGAACTCTACTAATG |
| SEQ ID NO: 79 | ATTTGAACTCTACTAATGTC |
| SEQ ID NO: 80 | TTTGAACTCTACTAATGTCA |
| SEQ ID NO: 81 | TTGAACTCTACTAATGTCAC |
| SEQ ID NO: 82 | TGAACTCTACTAATGTCACT |
| SEQ ID NO: 83 | GAACTCTACTAATGTCACTA |
| SEQ ID NO: 84 | AACTCTACTAATGTCACTAT |
| SEQ ID NO: 85 | ACTCTACTAATGTCACTATT |
| SEQ ID NO: 86 | ACGTACCAATGGAAAAACTC |
| SEQ ID NO: 87 | CGTACCAATGGAAAAACTCA |
| SEQ ID NO: 88 | GAAAACATGACACCCCGTGA |
| SEQ ID NO: 89 | AAAACATGACACCCCGTGAC |
| SEQ ID NO: 90 | AAACATGACACCCCGTGACC |
| SEQ ID NO: 91 | AACATGACACCCCGTGACCT |
| SEQ ID NO: 92 | CCTAACACCTACCTTGAAGG |
| SEQ ID NO: 93 | CACCTACCTTGAAGGTTCTG |
| SEQ ID NO: 94 | ATGTCATTCACTGTACTCTG |
| SEQ ID NO: 95 | TGTCATTCACTGTACTCTGT |
| SEQ ID NO: 96 | GTCATTCACTGTACTCTGTT |
| SEQ ID NO: 97 | TCATTCACTGTACTCTGTTT |
| SEQ ID NO: 98 | CATTCACTGTACTCTGTTTA |
| SEQ ID NO: 99 | ATTCACTGTACTCTGTTTAA |
| SEQ ID NO: 100 | CACTGTACTCTGTTTAACAC |
| SEQ ID NO: 101 | ACTGTACTCTGTTTAACACC |
| SEQ ID NO: 102 | CCAGTTTACTCATTCTTACC |

| | |
|---|---|
| SEQ ID NO: 103 | GTTTACTCATTCTTACCTGG |
| SEQ ID NO: 104 | TTACTCATTCTTACCTGGTG |
| SEQ ID NO: 105 | TACCAACCACCACAAACCTC |
| SEQ ID NO: 106 | ACCAACCACCACAAACCTCT |
| SEQ ID NO: 107 | CCAACCACCACAAACCTCTA |
| SEQ ID NO: 108 | ACCACCACAAACCTCTATCA |
| SEQ ID NO: 109 | CCACCACAAACCTCTATCAC |
| SEQ ID NO: 110 | CACCACAAACCTCTATCACC |
| SEQ ID NO: 111 | CCACAAACCTCTATCACCTC |
| SEQ ID NO: 112 | GACAGGTGGTTTCTCAATCG |
| SEQ ID NO: 113 | CAATCAAGGGTACACACCAC |
| SEQ ID NO: 114 | ATTCACAGGGACTACTCCCA |
| SEQ ID NO: 115 | TTCACAGGGACTACTCCCAC |
| SEQ ID NO: 116 | TCACAGGGACTACTCCCACC |
| SEQ ID NO: 117 | CACAGGGACTACTCCCACCC |
| SEQ ID NO: 118 | ACAGGGACTACTCCCACCCA |
| SEQ ID NO: 119 | CAGGGACTACTCCCACCCAA |
| SEQ ID NO: 120 | AGGGACTACTCCCACCCAAG |
| SEQ ID NO: 121 | GGGACTACTCCCACCCAAGA |
| SEQ ID NO: 122 | GGACTACTCCCACCCAAGAA |
| SEQ ID NO: 123 | GACTACTCCCACCCAAGAAT |
| SEQ ID NO: 124 | CTACTCCCACCCAAGAATAG |
| SEQ ID NO: 125 | GACCCAAATGTATAAACAGG |
| SEQ ID NO: 126 | ACACAACAAAGGGAGGTAGG |
| SEQ ID NO: 127 | CACAACAAAGGGAGGTAGGT |
| SEQ ID NO: 128 | CCCTAAGAGTGATGGAACTG |
| SEQ ID NO: 129 | CCTAAGAGTGATGGAACTGG |
| SEQ ID NO: 130 | GGGGGACAACCAATCACTAA |
| SEQ ID NO: 131 | CGGTGACATGGTACCACATA |
| SEQ ID NO: 132 | CCAGGTAGTGGAGTTCCTGT |
| SEQ ID NO: 133 | ATGACTTCACGGAAGAGAGG |
| SEQ ID NO: 134 | TGACTTCACGGAAGAGAGGT |
| SEQ ID NO: 135 | GACTTCACGGAAGAGAGGTT |
| SEQ ID NO: 136 | ATTGGGATCAGACATACCAC |
| SEQ ID NO: 137 | TTGGGATCAGACATACCACC |
| SEQ ID NO: 138 | TGGGATCAGACATACCACCC |
| SEQ ID NO: 139 | GGGATCAGACATACCACCCA |
| SEQ ID NO: 140 | GGATCAGACATACCACCCAA |
| SEQ ID NO: 141 | GATCAGACATACCACCCAAA |
| SEQ ID NO: 142 | ATCAGACATACCACCCAAAT |
| SEQ ID NO: 143 | TCAGACATACCACCCAAATT |
| SEQ ID NO: 144 | CTACAGTGTTCCCACCTACA |
| SEQ ID NO: 145 | ACAGTGTTCCCACCTACAAG |
| SEQ ID NO: 146 | CAGTGTTCCCACCTACAAGT |
| SEQ ID NO: 147 | CCCACCTACAAGTTTTGGAC |
| SEQ ID NO: 148 | CCACCTACAAGTTTTGGACC |
| SEQ ID NO: 149 | GAAAACCCTCACCTTATGGG |
| SEQ ID NO: 150 | AACCCTCACCTTATGGGTTG |
| SEQ ID NO: 151 | ACCCTCACCTTATGGGTTGG |
| SEQ ID NO: 152 | CCTCACCTTATGGGTTGGGA |
| SEQ ID NO: 153 | CTCACCTTATGGGTTGGGAT |
| SEQ ID NO: 154 | GTTAAACCAGGTGGAACCTC |
| SEQ ID NO: 155 | AAACCAGGTGGAACCTCATC |
| SEQ ID NO: 156 | ATGTTGGACTGAGACTGACC |
| SEQ ID NO: 157 | TGTTGGACTGAGACTGACCT |
| SEQ ID NO: 158 | GTTGGACTGAGACTGACCTT |
| SEQ ID NO: 159 | TGGACTGAGACTGACCTTAC |
| SEQ ID NO: 160 | GGACTGAGACTGACCTTACT |
| SEQ ID NO: 161 | TGTGTACCTTCCTTACCCAG |
| SEQ ID NO: 162 | GTGTACCTTCCTTACCCAGA |
| SEQ ID NO: 163 | GTACCTTCCTTACCCAGATC |
| SEQ ID NO: 164 | TACCTTCCTTACCCAGATCC |
| SEQ ID NO: 165 | ACCTTCCTTACCCAGATCCA |
| SEQ ID NO: 166 | CCTTCCTTACCCAGATCCAT |
| SEQ ID NO: 167 | CTTCCTTACCCAGATCCATC |
| SEQ ID NO: 168 | CCTTACCCAGATCCATCAAG |
| SEQ ID NO: 169 | CCCAGATCCATCAAGAATCC |
| SEQ ID NO: 170 | TCCATCAAGAATCCTAGGGG |
| SEQ ID NO: 171 | CTCCAGGTTGTGATGTCACA |
| SEQ ID NO: 172 | TCCAGGTTGTGATGTCACAG |
| SEQ ID NO: 173 | CCAGGTTGTGATGTCACAGA |
| SEQ ID NO: 174 | ACCTAGACCACCACTTAACC |
| SEQ ID NO: 175 | CCTAGACCACCACTTAACCG |
| SEQ ID NO: 176 | CTAGACCACCACTTAACCGA |
| SEQ ID NO: 177 | TGGTTATCGTGTAACTAAAA |
| SEQ ID NO: 178 | GGTTATCGTGTAACTAAAAA |
| SEQ ID NO: 179 | GTTATCGTGTAACTAAAAAC |
| SEQ ID NO: 180 | GTATTCTACACTCCAGGGAC |
| SEQ ID NO: 181 | TATTCTACACTCCAGGGACC |

| SEQ ID NO: 182 | ATTCTACACTCCAGGGACCA |
| --- | --- |
| SEQ ID NO: 183 | TTCTACACTCCAGGGACCAC |
| SEQ ID NO: 184 | TCTACACTCCAGGGACCACC |
| SEQ ID NO: 185 | CTACACTCCAGGGACCACCT |
| SEQ ID NO: 186 | TACACTCCAGGGACCACCTG |
| SEQ ID NO: 187 | ACACTCCAGGGACCACCTGG |
| SEQ ID NO: 188 | CACTCCAGGGACCACCTGGT |
| SEQ ID NO: 189 | ACTCCAGGGACCACCTGGTA |
| SEQ ID NO: 190 | CTCCAGGGACCACCTGGTAC |
| SEQ ID NO: 191 | TCCAGGGACCACCTGGTACT |
| SEQ ID NO: 192 | CCAGGGACCACCTGGTACTG |
| SEQ ID NO: 193 | CAGGGACCACCTGGTACTGG |
| SEQ ID NO: 194 | AGGGACCACCTGGTACTGGT |
| SEQ ID NO: 195 | GGGACCACCTGGTACTGGTA |
| SEQ ID NO: 196 | GGACCACCTGGTACTGGTAA |
| SEQ ID NO: 197 | GACCACCTGGTACTGGTAAG |
| SEQ ID NO: 198 | ACCACCTGGTACTGGTAAGA |
| SEQ ID NO: 199 | CCACCTGGTACTGGTAAGAG |
| SEQ ID NO: 200 | CACCTGGTACTGGTAAGAGT |
| SEQ ID NO: 201 | ACCTGGTACTGGTAAGAGTC |
| SEQ ID NO: 202 | CCTGGTACTGGTAAGAGTCA |
| SEQ ID NO: 203 | GGGACTACCAACTCAAACTG |
| SEQ ID NO: 204 | ACCTACACACCTCAGTGTTG |
| SEQ ID NO: 205 | CTTCGATGTCGAGGGGTGTC |
| SEQ ID NO: 206 | TTCGATGTCGAGGGGTGTCA |
| SEQ ID NO: 207 | TCGATGTCGAGGGGTGTCAT |
| SEQ ID NO: 208 | CGATGTCGAGGGGTGTCATG |
| SEQ ID NO: 209 | GTAGAAAGGTTCAACACATG |
| SEQ ID NO: 210 | TAGAAAGGTTCAACACATGG |
| SEQ ID NO: 211 | AGAAAGGTTCAACACATGGT |
| SEQ ID NO: 212 | CCCAGTTCTTCACGACATTG |
| SEQ ID NO: 213 | CTTCACGACATTGGTAACCC |
| SEQ ID NO: 214 | CTCTGACAGTCCATGTGAGT |
| SEQ ID NO: 215 | TCTGACAGTCCATGTGAGTC |
| SEQ ID NO: 216 | CTGACAGTCCATGTGAGTCT |
| SEQ ID NO: 217 | TGACAGTCCATGTGAGTCTC |
| SEQ ID NO: 218 | GACAGTCCATGTGAGTCTCA |
| SEQ ID NO: 219 | CAGTCCATGTGAGTCTCATG |
| SEQ ID NO: 220 | AGTCCATGTGAGTCTCATGG |
| SEQ ID NO: 221 | GTCCATGTGAGTCTCATGGA |
| SEQ ID NO: 222 | GGGACACTTTGATGGACAAC |
| SEQ ID NO: 223 | CACTTTGATGGACAACAGGG |
| SEQ ID NO: 224 | CTTTGATGGACAACAGGGTG |
| SEQ ID NO: 225 | TGATGGACAACAGGGTGAAG |
| SEQ ID NO: 226 | GATGGACAACAGGGTGAAGT |
| SEQ ID NO: 227 | TGGACAACAGGGTGAAGTAC |
| SEQ ID NO: 228 | GGACAACAGGGTGAAGTACC |
| SEQ ID NO: 229 | ACCAGAACTCAATTACCCCC |
| SEQ ID NO: 230 | CCAGAACTCAATTACCCCCT |
| SEQ ID NO: 231 | CAGAACTCAATTACCCCCTG |
| SEQ ID NO: 232 | CTATACATGTCTCTGGGACC |
| SEQ ID NO: 233 | CCTGGTGATTCTTCTTCAGG |
| SEQ ID NO: 234 | CACTTGACCCTCTCTCAGAA |
| SEQ ID NO: 235 | CTTGACCCTCTCTCAGAAAC |
| SEQ ID NO: 236 | TTGACCCTCTCTCAGAAACA |
| SEQ ID NO: 237 | TGACCCTCTCTCAGAAACAA |
| SEQ ID NO: 238 | GACCCTCTCTCAGAAACAAA |
| SEQ ID NO: 239 | TCCGTGATCCACAGACACTT |
| SEQ ID NO: 240 | CCGTGATCCACAGACACTTG |
| SEQ ID NO: 241 | CGTGATCCACAGACACTTGA |
| SEQ ID NO: 242 | GTGATCCACAGACACTTGAG |
| SEQ ID NO: 243 | GAGATTCTTGACATTACACC |
| SEQ ID NO: 244 | CAGATCAACTTACTCCTACT |
| SEQ ID NO: 245 | GATCAACTTACTCCTACTTG |
| SEQ ID NO: 246 | ATCAACTTACTCCTACTTGG |
| SEQ ID NO: 247 | CTCAGACTAATTCTCCTCGG |
| SEQ ID NO: 248 | CCAGTGTCTATGACCAAGAC |
| SEQ ID NO: 249 | TTACCAGATCCATCAAAACC |
| SEQ ID NO: 250 | TACCAGATCCATCAAAACCA |
| SEQ ID NO: 251 | ACCAGATCCATCAAAACCAA |
| SEQ ID NO: 252 | CCAGATCCATCAAAACCAAG |
| SEQ ID NO: 253 | CTTATGTCCTTCCCTCAGTC |
| SEQ ID NO: 254 | TATGAACCACAAATCATTAC |
| SEQ ID NO: 255 | ATGAACCACAAATCATTACT |
| SEQ ID NO: 256 | TGAACCACAAATCATTACTA |
| SEQ ID NO: 257 | GAACCACAAATCATTACTAC |
| SEQ ID NO: 258 | AACCACAAATCATTACTACA |
| SEQ ID NO: 259 | CCTCACTCCCTTTCGGATGG |
| SEQ ID NO: 260 | CTGTGATCCTTCGTGGACAT |

| SEQ ID NO: 261 | GTTCAAGAACTTTACTCTCC |
|---|---|
| SEQ ID NO: 262 | AAGAACTTTACTCTCCAATT |
| SEQ ID NO: 263 | AGAACTTTACTCTCCAATTT |
| SEQ ID NO: 264 | GAACTTTACTCTCCAATTTT |
| SEQ ID NO: 265 | GACCTTAAATTCCCTCGAGG |
| SEQ ID NO: 266 | CCTTAAATTCCCTCGAGGAC |
| SEQ ID NO: 267 | AAATTCCCTCGAGGACAAGG |
| SEQ ID NO: 268 | AGACGAATTCGTGGTGGTGA |
| SEQ ID NO: 269 | CAGACGTGGTCCAGAACAAA |
| SEQ ID NO: 270 | AGACGTGGTCCAGAACAAAC |
| SEQ ID NO: 271 | GACGTGGTCCAGAACAAACC |
| SEQ ID NO: 272 | ACGTGGTCCAGAACAAACCC |
| SEQ ID NO: 273 | CGTGGTCCAGAACAAACCCA |
| SEQ ID NO: 274 | GTGGTCCAGAACAAACCCAA |
| SEQ ID NO: 275 | TGGTCCAGAACAAACCCAAG |
| SEQ ID NO: 276 | GGTCCAGAACAAACCCAAGG |
| SEQ ID NO: 277 | GTCCAGAACAAACCCAAGGA |
| SEQ ID NO: 278 | GGAAATTTTGGGGACCAGGA |
| SEQ ID NO: 279 | AGTCACACCTTCGGGAACGT |
| SEQ ID NO: 280 | TCACACCTTCGGGAACGTGG |
| SEQ ID NO: 281 | CACACCTTCGGGAACGTGGT |
| SEQ ID NO: 282 | CACCTTCGGGAACGTGGTTG |
| SEQ ID NO: 283 | TTCGGGAACGTGGTTGACCT |
| SEQ ID NO: 284 | TCGGGAACGTGGTTGACCTA |
| SEQ ID NO: 285 | CGGGAACGTGGTTGACCTAC |
| SEQ ID NO: 286 | GGGAACGTGGTTGACCTACA |
| SEQ ID NO: 287 | GGAACGTGGTTGACCTACAC |
| SEQ ID NO: 288 | GAACGTGGTTGACCTACACA |
| SEQ ID NO: 289 | AACGTGGTTGACCTACACAG |
| SEQ ID NO: 290 | ACGTGGTTGACCTACACAGG |
| SEQ ID NO: 291 | CCACCACATTTTCACCGAGG |
| SEQ ID NO: 292 | CTATTAAGTGTGTACCTCAA |
| SEQ ID NO: 293 | CATACTAGGACCTCTTTCTG |

The invention claimed is:

1. A composition comprising a single oligonucleotide sequence comprising:
   (i) an RNA-binding domain from 8 to 30 nucleotides fully complementary to a region of a SARS-COV-2 RNA and
   (ii) at least one locked nucleic acid (LNA) domain comprising from 1 to 10 nucleotides; at least one 2'-O-methyl (2'-O-Me) domain comprising from 1 to 10 nucleotides; and/or at least one 2'-O-methoxyethyl (2'-MOE) domain comprising from 1 to 10 nucleotides, or a salt thereof;

wherein the single oligonucleotide sequence comprises a sequence fully complementary to SEQ ID NO: 206-213, 292 or 293.

2. The composition of claim 1 that comprises at least two sequences which are complementary to any two of SEQ ID NO: 206-213, 292 or 293, and which each bind to RNA encoding different viral antigens or regulatory sequences.

3. The composition of claim 1, wherein the oligonucleotide sequence comprises one or a plurality of locked nucleic acid (LNA) domains, of 2'-O-methyl (2'-O-Me) domains or of 2'-O-methoxyethyl (2'-MOE) domains.

4. The composition of claim 1, wherein the oligonucleotide sequence comprises two locked nucleic acid (LNA) domains, two 2'-O-methyl (2'-O-Me) domains or two 2'-O-methoxyethyl (2'-MOE) domains.

5. The composition of claim 1, wherein the oligonucleotide sequence comprises one or a plurality of DNA gap domains.

6. The composition of claim 5, wherein the DNA gap domain comprises from 6 to 11 nucleotides.

7. The composition of claim 1, wherein the oligonucleotide sequence comprises a central DNA gap domain flanked by a first LNA domain or 2'-O-methoxyethyl (2'-MOE) domain at a 5' end of the nucleotide sequence and a second LNA domain or 2'-O-methoxyethyl (2'-MOE) domain on a 3' end of the nucleotide sequence.

8. The composition of claim 1, wherein the oligonucleotide sequence further comprises from 1% to 99% modified nucleotides chosen from: 2'-O-methyl (2'-O-Me) modification, a 2'-O-methylphosphorothioate (2'-O-MePS) modification, a phosphorodiamidate morpholino (PMO) modification, a 2'methoxyethoxy (2'-MOE) modification, a vivo-morpholino (vPMO) modification, a peptide conjugate, a peptide nucleic acid (PNA), or LNA.

9. A pharmaceutical composition comprising: (i) a therapeutically effective amount of the composition of claim 1; and (ii) a pharmaceutically acceptable carrier.

10. The pharmaceutical composition of claim 9, further comprising a particle that encapsulates the oligonucleotide sequence.

11. A method for degrading coronavirus RNA or inhibiting replication of coronavirus comprising contacting coronavirus RNA with the composition of claim 1, optionally, after addition of RNAse H.

12. A method of treating a subject infected with SARS-COV-2 who has one or more symptoms of COVID-19 infection comprising administering the composition of claim 1.

13. A method of treating a subject who has been infected with SARS-COV-2 comprising administering the composition of claim 1.

14. The method of claim 12 that comprises administering the composition or pharmaceutical composition intranasally or into the upper or lower respiratory system.

15. The composition of claim 1, wherein the RNA-binding domain is fully complementary to a region of a SARS-COV-2 RNA is DNA.

* * * * *

SEQUENCE LISTING

```
<160> NUMBER OF SEQ ID NOS: 293

<210> SEQ ID NO 1
<211> LENGTH: 20
<212> TYPE: DNA
<213> ORGANISM: Homo sapiens

<400> SEQUENCE: 1
tcccaggtaa caaaccaacc                                               20

<210> SEQ ID NO 2
<211> LENGTH: 20
<212> TYPE: DNA
<213> ORGANISM: Homo sapiens

<400> SEQUENCE: 2
cccaggtaac aaaccaacca                                               20

<210> SEQ ID NO 3
<211> LENGTH: 20
<212> TYPE: DNA
<213> ORGANISM: Homo sapiens

<400> SEQUENCE: 3
cttacggttt cgtccgtgtt                                               20

<210> SEQ ID NO 4
<211> LENGTH: 20
<212> TYPE: DNA
<213> ORGANISM: Homo sapiens

<400> SEQUENCE: 4
ttacggtttc gtccgtgttg                                               20
```

```
<210> SEQ ID NO 5
<211> LENGTH: 20
<212> TYPE: DNA
<213> ORGANISM: Homo sapiens

<400> SEQUENCE: 5
tttcgtccgg gtgtgaccga                                                    20

<210> SEQ ID NO 6
<211> LENGTH: 20
<212> TYPE: DNA
<213> ORGANISM: Homo sapiens

<400> SEQUENCE: 6
ttcgtccggg tgtgaccgaa                                                    20

<210> SEQ ID NO 7
<211> LENGTH: 20
<212> TYPE: DNA
<213> ORGANISM: Homo sapiens

<400> SEQUENCE: 7
tcgtccgggt gtgaccgaaa                                                    20

<210> SEQ ID NO 8
<211> LENGTH: 20
<212> TYPE: DNA
<213> ORGANISM: Homo sapiens

<400> SEQUENCE: 8
ccttgtccct ggtttcaacg                                                    20

<210> SEQ ID NO 9
<211> LENGTH: 20
<212> TYPE: DNA
<213> ORGANISM: Homo sapiens

<400> SEQUENCE: 9
cttgtccctg gtttcaacga                                                    20

<210> SEQ ID NO 10
<211> LENGTH: 20
<212> TYPE: DNA
<213> ORGANISM: Homo sapiens

<400> SEQUENCE: 10
ttgtccctgg tttcaacgag                                                    20

<210> SEQ ID NO 11
<211> LENGTH: 20
<212> TYPE: DNA
<213> ORGANISM: Homo sapiens

<400> SEQUENCE: 11
tgtccctggt ttcaacgaga                                                    20

<210> SEQ ID NO 12
<211> LENGTH: 20
<212> TYPE: DNA
<213> ORGANISM: Homo sapiens

<400> SEQUENCE: 12
```

```
gtccctggtt tcaacgagaa                                              20

<210> SEQ ID NO 13
<211> LENGTH: 20
<212> TYPE: DNA
<213> ORGANISM: Homo sapiens

<400> SEQUENCE: 13
caacgagaaa acacacgtcc                                              20

<210> SEQ ID NO 14
<211> LENGTH: 20
<212> TYPE: DNA
<213> ORGANISM: Homo sapiens

<400> SEQUENCE: 14
cgagaaaaca cacgtccaac                                              20

<210> SEQ ID NO 15
<211> LENGTH: 20
<212> TYPE: DNA
<213> ORGANISM: Homo sapiens

<400> SEQUENCE: 15
cacacgtcca actcagtttg                                              20

<210> SEQ ID NO 16
<211> LENGTH: 20
<212> TYPE: DNA
<213> ORGANISM: Homo sapiens

<400> SEQUENCE: 16
tggtgtcctt gtccctcatg                                              20

<210> SEQ ID NO 17
<211> LENGTH: 20
<212> TYPE: DNA
<213> ORGANISM: Homo sapiens

<400> SEQUENCE: 17
ggtgtccttg tccctcatgt                                              20

<210> SEQ ID NO 18
<211> LENGTH: 20
<212> TYPE: DNA
<213> ORGANISM: Homo sapiens

<400> SEQUENCE: 18
gtgtccttgt ccctcatgtg                                              20

<210> SEQ ID NO 19
<211> LENGTH: 20
<212> TYPE: DNA
<213> ORGANISM: Homo sapiens

<400> SEQUENCE: 19
tgtccttgtc cctcatgtgg                                              20

<210> SEQ ID NO 20
<211> LENGTH: 20
<212> TYPE: DNA
<213> ORGANISM: Homo sapiens

<400> SEQUENCE: 20
```

```
gtccttgtcc ctcatgtggg                                               20

<210> SEQ ID NO 21
<211> LENGTH: 20
<212> TYPE: DNA
<213> ORGANISM: Homo sapiens

<400> SEQUENCE: 21
caccttcaat ggggaatgtc                                               20

<210> SEQ ID NO 22
<211> LENGTH: 20
<212> TYPE: DNA
<213> ORGANISM: Homo sapiens

<400> SEQUENCE: 22
accttcaatg gggaatgtcc                                               20

<210> SEQ ID NO 23
<211> LENGTH: 20
<212> TYPE: DNA
<213> ORGANISM: Homo sapiens

<400> SEQUENCE: 23
ccttcaatgg ggaatgtcca                                               20

<210> SEQ ID NO 24
<211> LENGTH: 20
<212> TYPE: DNA
<213> ORGANISM: Homo sapiens

<400> SEQUENCE: 24
caaattgttg aatcctgtgg                                               20

<210> SEQ ID NO 25
<211> LENGTH: 20
<212> TYPE: DNA
<213> ORGANISM: Homo sapiens

<400> SEQUENCE: 25
tagagggaga aacacttccc                                               20

<210> SEQ ID NO 26
<211> LENGTH: 20
<212> TYPE: DNA
<213> ORGANISM: Homo sapiens

<400> SEQUENCE: 26
agagggagaa acacttccca                                               20

<210> SEQ ID NO 27
<211> LENGTH: 20
<212> TYPE: DNA
<213> ORGANISM: Homo sapiens

<400> SEQUENCE: 27
gagggagaaa cacttcccac                                               20

<210> SEQ ID NO 28
<211> LENGTH: 20
<212> TYPE: DNA
<213> ORGANISM: Homo sapiens
```

-continued

<400> SEQUENCE: 28
agggagaaac acttcccaca                                              20

<210> SEQ ID NO 29
<211> LENGTH: 20
<212> TYPE: DNA
<213> ORGANISM: Homo sapiens

<400> SEQUENCE: 29
gggagaaaca cttcccacag                                              20

<210> SEQ ID NO 30
<211> LENGTH: 20
<212> TYPE: DNA
<213> ORGANISM: Homo sapiens

<400> SEQUENCE: 30
ggagaaacac ttcccacaga                                              20

<210> SEQ ID NO 31
<211> LENGTH: 20
<212> TYPE: DNA
<213> ORGANISM: Homo sapiens

<400> SEQUENCE: 31
ctttctaccc tccagatgag                                              20

<210> SEQ ID NO 32
<211> LENGTH: 20
<212> TYPE: DNA
<213> ORGANISM: Homo sapiens

<400> SEQUENCE: 32
tttctaccct ccagatgagg                                              20

<210> SEQ ID NO 33
<211> LENGTH: 20
<212> TYPE: DNA
<213> ORGANISM: Homo sapiens

<400> SEQUENCE: 33
ttctaccctc cagatgagga                                              20

<210> SEQ ID NO 34
<211> LENGTH: 20
<212> TYPE: DNA
<213> ORGANISM: Homo sapiens

<400> SEQUENCE: 34
tctaccctcc agatgaggat                                              20

<210> SEQ ID NO 35
<211> LENGTH: 20
<212> TYPE: DNA
<213> ORGANISM: Homo sapiens

<400> SEQUENCE: 35
ctaccctcca gatgaggatg                                              20

<210> SEQ ID NO 36
<211> LENGTH: 20
<212> TYPE: DNA
<213> ORGANISM: Homo sapiens

<400> SEQUENCE: 36
taccctccag atgaggatga                                                    20

<210> SEQ ID NO 37
<211> LENGTH: 20
<212> TYPE: DNA
<213> ORGANISM: Homo sapiens

<400> SEQUENCE: 37
accctccaga tgaggatgaa                                                    20

<210> SEQ ID NO 38
<211> LENGTH: 20
<212> TYPE: DNA
<213> ORGANISM: Homo sapiens

<400> SEQUENCE: 38
ccctccagat gaggatgaag                                                    20

<210> SEQ ID NO 39
<211> LENGTH: 20
<212> TYPE: DNA
<213> ORGANISM: Homo sapiens

<400> SEQUENCE: 39
tggaccactt aaagtgggtg                                                    20

<210> SEQ ID NO 40
<211> LENGTH: 20
<212> TYPE: DNA
<213> ORGANISM: Homo sapiens

<400> SEQUENCE: 40
ggaccactta aagtgggtgg                                                    20

<210> SEQ ID NO 41
<211> LENGTH: 20
<212> TYPE: DNA
<213> ORGANISM: Homo sapiens

<400> SEQUENCE: 41
gaccacttaa agtgggtggt                                                    20

<210> SEQ ID NO 42
<211> LENGTH: 20
<212> TYPE: DNA
<213> ORGANISM: Homo sapiens

<400> SEQUENCE: 42
cacttacccg ggtcagggtt                                                    20

<210> SEQ ID NO 43
<211> LENGTH: 20
<212> TYPE: DNA
<213> ORGANISM: Homo sapiens

<400> SEQUENCE: 43
acttacccgg gtcagggttt                                                    20

<210> SEQ ID NO 44
<211> LENGTH: 20
<212> TYPE: DNA

```
<213> ORGANISM: Homo sapiens

<400> SEQUENCE: 44
cttacccggg tcagggttta                                              20

<210> SEQ ID NO 45
<211> LENGTH: 20
<212> TYPE: DNA
<213> ORGANISM: Homo sapiens

<400> SEQUENCE: 45
ttacccgggt cagggtttaa                                              20

<210> SEQ ID NO 46
<211> LENGTH: 20
<212> TYPE: DNA
<213> ORGANISM: Homo sapiens

<400> SEQUENCE: 46
tacccgggtc agggtttaaa                                              20

<210> SEQ ID NO 47
<211> LENGTH: 20
<212> TYPE: DNA
<213> ORGANISM: Homo sapiens

<400> SEQUENCE: 47
acccgggtca gggtttaaat                                              20

<210> SEQ ID NO 48
<211> LENGTH: 20
<212> TYPE: DNA
<213> ORGANISM: Homo sapiens

<400> SEQUENCE: 48
cccgggtcag ggtttaaatg                                              20

<210> SEQ ID NO 49
<211> LENGTH: 20
<212> TYPE: DNA
<213> ORGANISM: Homo sapiens

<400> SEQUENCE: 49
ccgggtcagg gtttaaatgg                                              20

<210> SEQ ID NO 50
<211> LENGTH: 20
<212> TYPE: DNA
<213> ORGANISM: Homo sapiens

<400> SEQUENCE: 50
cgggtcaggg tttaaatggt                                              20

<210> SEQ ID NO 51
<211> LENGTH: 20
<212> TYPE: DNA
<213> ORGANISM: Homo sapiens

<400> SEQUENCE: 51
tacactagta atcctaccac                                              20

<210> SEQ ID NO 52
<211> LENGTH: 20
```

```
<212> TYPE: DNA
<213> ORGANISM: Homo sapiens

<400> SEQUENCE: 52
acactagtaa tcctaccaca                                               20

<210> SEQ ID NO 53
<211> LENGTH: 20
<212> TYPE: DNA
<213> ORGANISM: Homo sapiens

<400> SEQUENCE: 53
cactagtaat cctaccacat                                               20

<210> SEQ ID NO 54
<211> LENGTH: 20
<212> TYPE: DNA
<213> ORGANISM: Homo sapiens

<400> SEQUENCE: 54
ctagtaatcc taccacattc                                               20

<210> SEQ ID NO 55
<211> LENGTH: 20
<212> TYPE: DNA
<213> ORGANISM: Homo sapiens

<400> SEQUENCE: 55
tagtaatcct accacattcc                                               20

<210> SEQ ID NO 56
<211> LENGTH: 20
<212> TYPE: DNA
<213> ORGANISM: Homo sapiens

<400> SEQUENCE: 56
agtaatccta ccacattcca                                               20

<210> SEQ ID NO 57
<211> LENGTH: 20
<212> TYPE: DNA
<213> ORGANISM: Homo sapiens

<400> SEQUENCE: 57
gtaatcctac cacattccac                                               20

<210> SEQ ID NO 58
<211> LENGTH: 20
<212> TYPE: DNA
<213> ORGANISM: Homo sapiens

<400> SEQUENCE: 58
taatcctacc acattccacc                                               20

<210> SEQ ID NO 59
<211> LENGTH: 20
<212> TYPE: DNA
<213> ORGANISM: Homo sapiens

<400> SEQUENCE: 59
aatcctacca cattccacct                                               20

<210> SEQ ID NO 60
```

```
<211> LENGTH: 20
<212> TYPE: DNA
<213> ORGANISM: Homo sapiens

<400> SEQUENCE: 60
atcctaccac attccaccta                                               20

<210> SEQ ID NO 61
<211> LENGTH: 20
<212> TYPE: DNA
<213> ORGANISM: Homo sapiens

<400> SEQUENCE: 61
tcctaccaca ttccacctag                                               20

<210> SEQ ID NO 62
<211> LENGTH: 20
<212> TYPE: DNA
<213> ORGANISM: Homo sapiens

<400> SEQUENCE: 62
cctaccacat tccacctaga                                               20

<210> SEQ ID NO 63
<211> LENGTH: 20
<212> TYPE: DNA
<213> ORGANISM: Homo sapiens

<400> SEQUENCE: 63
ctaccacatt ccacctagat                                               20

<210> SEQ ID NO 64
<211> LENGTH: 20
<212> TYPE: DNA
<213> ORGANISM: Homo sapiens

<400> SEQUENCE: 64
taccacattc cacctagatg                                               20

<210> SEQ ID NO 65
<211> LENGTH: 20
<212> TYPE: DNA
<213> ORGANISM: Homo sapiens

<400> SEQUENCE: 65
accacattcc acctagatgg                                               20

<210> SEQ ID NO 66
<211> LENGTH: 20
<212> TYPE: DNA
<213> ORGANISM: Homo sapiens

<400> SEQUENCE: 66
ccacattcca cctagatggt                                               20

<210> SEQ ID NO 67
<211> LENGTH: 20
<212> TYPE: DNA
<213> ORGANISM: Homo sapiens

<400> SEQUENCE: 67
cacattccac ctagatggtg                                               20
```

```
<210> SEQ ID NO 68
<211> LENGTH: 20
<212> TYPE: DNA
<213> ORGANISM: Homo sapiens

<400> SEQUENCE: 68
cagatacctt gtacgtgtgg                                              20

<210> SEQ ID NO 69
<211> LENGTH: 20
<212> TYPE: DNA
<213> ORGANISM: Homo sapiens

<400> SEQUENCE: 69
ctagtacaac aggagtcacc                                              20

<210> SEQ ID NO 70
<211> LENGTH: 20
<212> TYPE: DNA
<213> ORGANISM: Homo sapiens

<400> SEQUENCE: 70
atcctaccat acagaaagac                                              20

<210> SEQ ID NO 71
<211> LENGTH: 20
<212> TYPE: DNA
<213> ORGANISM: Homo sapiens

<400> SEQUENCE: 71
tcctaccata cagaaagacg                                              20

<210> SEQ ID NO 72
<211> LENGTH: 20
<212> TYPE: DNA
<213> ORGANISM: Homo sapiens

<400> SEQUENCE: 72
cctaccatac agaaagacgt                                              20

<210> SEQ ID NO 73
<211> LENGTH: 20
<212> TYPE: DNA
<213> ORGANISM: Homo sapiens

<400> SEQUENCE: 73
ctaccataca gaaagacgtt                                              20

<210> SEQ ID NO 74
<211> LENGTH: 20
<212> TYPE: DNA
<213> ORGANISM: Homo sapiens

<400> SEQUENCE: 74
taccatacag aaagacgttc                                              20

<210> SEQ ID NO 75
<211> LENGTH: 20
<212> TYPE: DNA
<213> ORGANISM: Homo sapiens

<400> SEQUENCE: 75
accatacaga aagacgttct                                              20
```

```
<210> SEQ ID NO 76
<211> LENGTH: 20
<212> TYPE: DNA
<213> ORGANISM: Homo sapiens

<400> SEQUENCE: 76
ccatacagaa agacgttctt                                              20

<210> SEQ ID NO 77
<211> LENGTH: 20
<212> TYPE: DNA
<213> ORGANISM: Homo sapiens

<400> SEQUENCE: 77
ctaccgaagt tgtaggagac                                              20

<210> SEQ ID NO 78
<211> LENGTH: 20
<212> TYPE: DNA
<213> ORGANISM: Homo sapiens

<400> SEQUENCE: 78
ctatttgaac tctactaatg                                              20

<210> SEQ ID NO 79
<211> LENGTH: 20
<212> TYPE: DNA
<213> ORGANISM: Homo sapiens

<400> SEQUENCE: 79
atttgaactc tactaatgtc                                              20

<210> SEQ ID NO 80
<211> LENGTH: 20
<212> TYPE: DNA
<213> ORGANISM: Homo sapiens

<400> SEQUENCE: 80
tttgaactct actaatgtca                                              20

<210> SEQ ID NO 81
<211> LENGTH: 20
<212> TYPE: DNA
<213> ORGANISM: Homo sapiens

<400> SEQUENCE: 81
ttgaactcta ctaatgtcac                                              20

<210> SEQ ID NO 82
<211> LENGTH: 20
<212> TYPE: DNA
<213> ORGANISM: Homo sapiens

<400> SEQUENCE: 82
tgaactctac taatgtcact                                              20

<210> SEQ ID NO 83
<211> LENGTH: 20
<212> TYPE: DNA
<213> ORGANISM: Homo sapiens

<400> SEQUENCE: 83
gaactctact aatgtcacta                                              20
```

<210> SEQ ID NO 84
<211> LENGTH: 20
<212> TYPE: DNA
<213> ORGANISM: Homo sapiens

<400> SEQUENCE: 84
aactctacta atgtcactat                                               20

<210> SEQ ID NO 85
<211> LENGTH: 20
<212> TYPE: DNA
<213> ORGANISM: Homo sapiens

<400> SEQUENCE: 85
actctactaa tgtcactatt                                               20

<210> SEQ ID NO 86
<211> LENGTH: 20
<212> TYPE: DNA
<213> ORGANISM: Homo sapiens

<400> SEQUENCE: 86
acgtaccaat ggaaaaactc                                               20

<210> SEQ ID NO 87
<211> LENGTH: 20
<212> TYPE: DNA
<213> ORGANISM: Homo sapiens

<400> SEQUENCE: 87
cgtaccaatg gaaaaactca                                               20

<210> SEQ ID NO 88
<211> LENGTH: 20
<212> TYPE: DNA
<213> ORGANISM: Homo sapiens

<400> SEQUENCE: 88
gaaaacatga caccccgtga                                               20

<210> SEQ ID NO 89
<211> LENGTH: 20
<212> TYPE: DNA
<213> ORGANISM: Homo sapiens

<400> SEQUENCE: 89
aaaacatgac accccgtgac                                               20

<210> SEQ ID NO 90
<211> LENGTH: 20
<212> TYPE: DNA
<213> ORGANISM: Homo sapiens

<400> SEQUENCE: 90
aaacatgaca ccccgtgacc                                               20

<210> SEQ ID NO 91
<211> LENGTH: 20
<212> TYPE: DNA
<213> ORGANISM: Homo sapiens

<400> SEQUENCE: 91
aacatgacac cccgtgacct                                          20

<210> SEQ ID NO 92
<211> LENGTH: 20
<212> TYPE: DNA
<213> ORGANISM: Homo sapiens

<400> SEQUENCE: 92
cctaacacct accttgaagg                                          20

<210> SEQ ID NO 93
<211> LENGTH: 20
<212> TYPE: DNA
<213> ORGANISM: Homo sapiens

<400> SEQUENCE: 93
cacctacctt gaaggttctg                                          20

<210> SEQ ID NO 94
<211> LENGTH: 20
<212> TYPE: DNA
<213> ORGANISM: Homo sapiens

<400> SEQUENCE: 94
atgtcattca ctgtactctg                                          20

<210> SEQ ID NO 95
<211> LENGTH: 20
<212> TYPE: DNA
<213> ORGANISM: Homo sapiens

<400> SEQUENCE: 95
tgtcattcac tgtactctgt                                          20

<210> SEQ ID NO 96
<211> LENGTH: 20
<212> TYPE: DNA
<213> ORGANISM: Homo sapiens

<400> SEQUENCE: 96
gtcattcact gtactctgtt                                          20

<210> SEQ ID NO 97
<211> LENGTH: 20
<212> TYPE: DNA
<213> ORGANISM: Homo sapiens

<400> SEQUENCE: 97
tcattcactg tactctgttt                                          20

<210> SEQ ID NO 98
<211> LENGTH: 20
<212> TYPE: DNA
<213> ORGANISM: Homo sapiens

<400> SEQUENCE: 98
cattcactgt actctgttta                                          20

<210> SEQ ID NO 99
<211> LENGTH: 20
<212> TYPE: DNA
<213> ORGANISM: Homo sapiens

<400> SEQUENCE: 99

```
attcactgta ctctgtttaa                                               20

<210> SEQ ID NO 100
<211> LENGTH: 20
<212> TYPE: DNA
<213> ORGANISM: Homo sapiens

<400> SEQUENCE: 100
cactgtactc tgtttaacac                                               20

<210> SEQ ID NO 101
<211> LENGTH: 20
<212> TYPE: DNA
<213> ORGANISM: Homo sapiens

<400> SEQUENCE: 101
actgtactct gtttaacacc                                               20

<210> SEQ ID NO 102
<211> LENGTH: 20
<212> TYPE: DNA
<213> ORGANISM: Homo sapiens

<400> SEQUENCE: 102
ccagtttact cattcttacc                                               20

<210> SEQ ID NO 103
<211> LENGTH: 20
<212> TYPE: DNA
<213> ORGANISM: Homo sapiens

<400> SEQUENCE: 103
gtttactcat tcttacctgg                                               20

<210> SEQ ID NO 104
<211> LENGTH: 20
<212> TYPE: DNA
<213> ORGANISM: Homo sapiens

<400> SEQUENCE: 104
ttactcattc ttacctggtg                                               20

<210> SEQ ID NO 105
<211> LENGTH: 20
<212> TYPE: DNA
<213> ORGANISM: Homo sapiens

<400> SEQUENCE: 105
taccaaccac cacaaacctc                                               20

<210> SEQ ID NO 106
<211> LENGTH: 20
<212> TYPE: DNA
<213> ORGANISM: Homo sapiens

<400> SEQUENCE: 106
accaaccacc acaaacctct                                               20

<210> SEQ ID NO 107
<211> LENGTH: 20
<212> TYPE: DNA
<213> ORGANISM: Homo sapiens
```

```
<400> SEQUENCE: 107
ccaaccacca caaacctcta                                          20

<210> SEQ ID NO 108
<211> LENGTH: 20
<212> TYPE: DNA
<213> ORGANISM: Homo sapiens

<400> SEQUENCE: 108
accaccacaa acctctatca                                          20

<210> SEQ ID NO 109
<211> LENGTH: 20
<212> TYPE: DNA
<213> ORGANISM: Homo sapiens

<400> SEQUENCE: 109
ccaccacaaa cctctatcac                                          20

<210> SEQ ID NO 110
<211> LENGTH: 20
<212> TYPE: DNA
<213> ORGANISM: Homo sapiens

<400> SEQUENCE: 110
caccacaaac ctctatcacc                                          20

<210> SEQ ID NO 111
<211> LENGTH: 20
<212> TYPE: DNA
<213> ORGANISM: Homo sapiens

<400> SEQUENCE: 111
ccacaaacct ctatcacctc                                          20

<210> SEQ ID NO 112
<211> LENGTH: 20
<212> TYPE: DNA
<213> ORGANISM: Homo sapiens

<400> SEQUENCE: 112
gacaggtggt ttctcaatcg                                          20

<210> SEQ ID NO 113
<211> LENGTH: 20
<212> TYPE: DNA
<213> ORGANISM: Homo sapiens

<400> SEQUENCE: 113
caatcaaggg tacacaccac                                          20

<210> SEQ ID NO 114
<211> LENGTH: 20
<212> TYPE: DNA
<213> ORGANISM: Homo sapiens

<400> SEQUENCE: 114
attcacaggg actactccca                                          20

<210> SEQ ID NO 115
<211> LENGTH: 20
<212> TYPE: DNA
```

```
<400> SEQUENCE: 115
ttcacaggga ctactcccac                                                     20

<210> SEQ ID NO 116
<211> LENGTH: 20
<212> TYPE: DNA
<213> ORGANISM: Homo sapiens

<400> SEQUENCE: 116
tcacagggac tactcccacc                                                     20

<210> SEQ ID NO 117
<211> LENGTH: 20
<212> TYPE: DNA
<213> ORGANISM: Homo sapiens

<400> SEQUENCE: 117
cacagggact actcccaccc                                                     20

<210> SEQ ID NO 118
<211> LENGTH: 20
<212> TYPE: DNA
<213> ORGANISM: Homo sapiens

<400> SEQUENCE: 118
acagggacta ctcccaccca                                                     20

<210> SEQ ID NO 119
<211> LENGTH: 20
<212> TYPE: DNA
<213> ORGANISM: Homo sapiens

<400> SEQUENCE: 119
cagggactac tcccacccaa                                                     20

<210> SEQ ID NO 120
<211> LENGTH: 20
<212> TYPE: DNA
<213> ORGANISM: Homo sapiens

<400> SEQUENCE: 120
agggactact cccacccaag                                                     20

<210> SEQ ID NO 121
<211> LENGTH: 20
<212> TYPE: DNA
<213> ORGANISM: Homo sapiens

<400> SEQUENCE: 121
gggactactc ccacccaaga                                                     20

<210> SEQ ID NO 122
<211> LENGTH: 20
<212> TYPE: DNA
<213> ORGANISM: Homo sapiens

<400> SEQUENCE: 122
ggactactcc cacccaagaa                                                     20

<210> SEQ ID NO 123
<211> LENGTH: 20
<212> TYPE: DNA
```

```
<213> ORGANISM: Homo sapiens

<400> SEQUENCE: 123
gactactccc acccaagaat                                               20

<210> SEQ ID NO 124
<211> LENGTH: 20
<212> TYPE: DNA
<213> ORGANISM: Homo sapiens

<400> SEQUENCE: 124
ctactcccac ccaagaatag                                               20

<210> SEQ ID NO 125
<211> LENGTH: 20
<212> TYPE: DNA
<213> ORGANISM: Homo sapiens

<400> SEQUENCE: 125
gacccaaatg tataaacagg                                               20

<210> SEQ ID NO 126
<211> LENGTH: 20
<212> TYPE: DNA
<213> ORGANISM: Homo sapiens

<400> SEQUENCE: 126
acacaacaaa gggaggtagg                                               20

<210> SEQ ID NO 127
<211> LENGTH: 20
<212> TYPE: DNA
<213> ORGANISM: Homo sapiens

<400> SEQUENCE: 127
cacaacaaag ggaggtaggt                                               20

<210> SEQ ID NO 128
<211> LENGTH: 20
<212> TYPE: DNA
<213> ORGANISM: Homo sapiens

<400> SEQUENCE: 128
ccctaagagt gatggaactg                                               20

<210> SEQ ID NO 129
<211> LENGTH: 20
<212> TYPE: DNA
<213> ORGANISM: Homo sapiens

<400> SEQUENCE: 129
cctaagagtg atggaactgg                                               20

<210> SEQ ID NO 130
<211> LENGTH: 20
<212> TYPE: DNA
<213> ORGANISM: Homo sapiens

<400> SEQUENCE: 130
gggggacaac caatcactaa                                               20

<210> SEQ ID NO 131
<211> LENGTH: 20
```

```
<212> TYPE: DNA
<213> ORGANISM: Homo sapiens

<400> SEQUENCE: 131
cggtgacatg gtaccacata                                              20

<210> SEQ ID NO 132
<211> LENGTH: 20
<212> TYPE: DNA
<213> ORGANISM: Homo sapiens

<400> SEQUENCE: 132
ccaggtagtg gagttcctgt                                              20

<210> SEQ ID NO 133
<211> LENGTH: 20
<212> TYPE: DNA
<213> ORGANISM: Homo sapiens

<400> SEQUENCE: 133
atgacttcac ggaagagagg                                              20

<210> SEQ ID NO 134
<211> LENGTH: 20
<212> TYPE: DNA
<213> ORGANISM: Homo sapiens

<400> SEQUENCE: 134
tgacttcacg gaagagaggt                                              20

<210> SEQ ID NO 135
<211> LENGTH: 20
<212> TYPE: DNA
<213> ORGANISM: Homo sapiens

<400> SEQUENCE: 135
gacttcacgg aagagaggtt                                              20

<210> SEQ ID NO 136
<211> LENGTH: 20
<212> TYPE: DNA
<213> ORGANISM: Homo sapiens

<400> SEQUENCE: 136
attgggatca gacataccac                                              20

<210> SEQ ID NO 137
<211> LENGTH: 20
<212> TYPE: DNA
<213> ORGANISM: Homo sapiens

<400> SEQUENCE: 137
ttgggatcag acataccacc                                              20

<210> SEQ ID NO 138
<211> LENGTH: 20
<212> TYPE: DNA
<213> ORGANISM: Homo sapiens

<400> SEQUENCE: 138
tgggatcaga cataccaccc                                              20

<210> SEQ ID NO 139
```

```
<211> LENGTH: 20
<212> TYPE: DNA
<213> ORGANISM: Homo sapiens

<400> SEQUENCE: 139
gggatcagac ataccaccca                                              20

<210> SEQ ID NO 140
<211> LENGTH: 20
<212> TYPE: DNA
<213> ORGANISM: Homo sapiens

<400> SEQUENCE: 140
ggatcagaca taccacccaa                                              20

<210> SEQ ID NO 141
<211> LENGTH: 20
<212> TYPE: DNA
<213> ORGANISM: Homo sapiens

<400> SEQUENCE: 141
gatcagacat accacccaaa                                              20

<210> SEQ ID NO 142
<211> LENGTH: 20
<212> TYPE: DNA
<213> ORGANISM: Homo sapiens

<400> SEQUENCE: 142
atcagacata ccacccaaat                                              20

<210> SEQ ID NO 143
<211> LENGTH: 20
<212> TYPE: DNA
<213> ORGANISM: Homo sapiens

<400> SEQUENCE: 143
tcagacatac cacccaaatt                                              20

<210> SEQ ID NO 144
<211> LENGTH: 20
<212> TYPE: DNA
<213> ORGANISM: Homo sapiens

<400> SEQUENCE: 144
ctacagtgtt cccacctaca                                              20

<210> SEQ ID NO 145
<211> LENGTH: 20
<212> TYPE: DNA
<213> ORGANISM: Homo sapiens

<400> SEQUENCE: 145
acagtgttcc cacctacaag                                              20

<210> SEQ ID NO 146
<211> LENGTH: 20
<212> TYPE: DNA
<213> ORGANISM: Homo sapiens

<400> SEQUENCE: 146
cagtgttccc acctacaagt                                              20
```

```
<210> SEQ ID NO 147
<211> LENGTH: 20
<212> TYPE: DNA
<213> ORGANISM: Homo sapiens

<400> SEQUENCE: 147
cccacctaca agttttggac                                              20

<210> SEQ ID NO 148
<211> LENGTH: 20
<212> TYPE: DNA
<213> ORGANISM: Homo sapiens

<400> SEQUENCE: 148
ccacctacaa gttttggacc                                              20

<210> SEQ ID NO 149
<211> LENGTH: 20
<212> TYPE: DNA
<213> ORGANISM: Homo sapiens

<400> SEQUENCE: 149
gaaaaccctc accttatggg                                              20

<210> SEQ ID NO 150
<211> LENGTH: 20
<212> TYPE: DNA
<213> ORGANISM: Homo sapiens

<400> SEQUENCE: 150
aaccctcacc ttatgggttg                                              20

<210> SEQ ID NO 151
<211> LENGTH: 20
<212> TYPE: DNA
<213> ORGANISM: Homo sapiens

<400> SEQUENCE: 151
accctcacct tatgggttgg                                              20

<210> SEQ ID NO 152
<211> LENGTH: 20
<212> TYPE: DNA
<213> ORGANISM: Homo sapiens

<400> SEQUENCE: 152
cctcacctta tgggttggga                                              20

<210> SEQ ID NO 153
<211> LENGTH: 20
<212> TYPE: DNA
<213> ORGANISM: Homo sapiens

<400> SEQUENCE: 153
ctcaccttat gggttgggat                                              20

<210> SEQ ID NO 154
<211> LENGTH: 20
<212> TYPE: DNA
<213> ORGANISM: Homo sapiens

<400> SEQUENCE: 154
gttaaaccag gtggaacctc                                              20
```

```
<210> SEQ ID NO 155
<211> LENGTH: 20
<212> TYPE: DNA
<213> ORGANISM: Homo sapiens

<400> SEQUENCE: 155
aaaccaggtg gaacctcatc                                               20

<210> SEQ ID NO 156
<211> LENGTH: 20
<212> TYPE: DNA
<213> ORGANISM: Homo sapiens

<400> SEQUENCE: 156
atgttggact gagactgacc                                               20

<210> SEQ ID NO 157
<211> LENGTH: 20
<212> TYPE: DNA
<213> ORGANISM: Homo sapiens

<400> SEQUENCE: 157
tgttggactg agactgacct                                               20

<210> SEQ ID NO 158
<211> LENGTH: 20
<212> TYPE: DNA
<213> ORGANISM: Homo sapiens

<400> SEQUENCE: 158
gttggactga gactgacctt                                               20

<210> SEQ ID NO 159
<211> LENGTH: 20
<212> TYPE: DNA
<213> ORGANISM: Homo sapiens

<400> SEQUENCE: 159
tggactgaga ctgaccttac                                               20

<210> SEQ ID NO 160
<211> LENGTH: 20
<212> TYPE: DNA
<213> ORGANISM: Homo sapiens

<400> SEQUENCE: 160
ggactgagac tgaccttact                                               20

<210> SEQ ID NO 161
<211> LENGTH: 20
<212> TYPE: DNA
<213> ORGANISM: Homo sapiens

<400> SEQUENCE: 161
tgtgtacctt ccttacccag                                               20

<210> SEQ ID NO 162
<211> LENGTH: 20
<212> TYPE: DNA
<213> ORGANISM: Homo sapiens

<400> SEQUENCE: 162
gtgtaccttc cttacccaga                                               20
```

<210> SEQ ID NO 163
<211> LENGTH: 20
<212> TYPE: DNA
<213> ORGANISM: Homo sapiens

<400> SEQUENCE: 163
gtaccttcct tacccagatc                                               20

<210> SEQ ID NO 164
<211> LENGTH: 20
<212> TYPE: DNA
<213> ORGANISM: Homo sapiens

<400> SEQUENCE: 164
taccttcctt acccagatcc                                               20

<210> SEQ ID NO 165
<211> LENGTH: 20
<212> TYPE: DNA
<213> ORGANISM: Homo sapiens

<400> SEQUENCE: 165
accttcctta cccagatcca                                               20

<210> SEQ ID NO 166
<211> LENGTH: 20
<212> TYPE: DNA
<213> ORGANISM: Homo sapiens

<400> SEQUENCE: 166
ccttccttac ccagatccat                                               20

<210> SEQ ID NO 167
<211> LENGTH: 20
<212> TYPE: DNA
<213> ORGANISM: Homo sapiens

<400> SEQUENCE: 167
cttccttacc cagatccatc                                               20

<210> SEQ ID NO 168
<211> LENGTH: 20
<212> TYPE: DNA
<213> ORGANISM: Homo sapiens

<400> SEQUENCE: 168
ccttacccag atccatcaag                                               20

<210> SEQ ID NO 169
<211> LENGTH: 20
<212> TYPE: DNA
<213> ORGANISM: Homo sapiens

<400> SEQUENCE: 169
cccagatcca tcaagaatcc                                               20

<210> SEQ ID NO 170
<211> LENGTH: 20
<212> TYPE: DNA
<213> ORGANISM: Homo sapiens

<400> SEQUENCE: 170
tccatcaaga atcctagggg                                           20

<210> SEQ ID NO 171
<211> LENGTH: 20
<212> TYPE: DNA
<213> ORGANISM: Homo sapiens

<400> SEQUENCE: 171
ctccaggttg tgatgtcaca                                           20

<210> SEQ ID NO 172
<211> LENGTH: 20
<212> TYPE: DNA
<213> ORGANISM: Homo sapiens

<400> SEQUENCE: 172
tccaggttgt gatgtcacag                                           20

<210> SEQ ID NO 173
<211> LENGTH: 20
<212> TYPE: DNA
<213> ORGANISM: Homo sapiens

<400> SEQUENCE: 173
ccaggttgtg atgtcacaga                                           20

<210> SEQ ID NO 174
<211> LENGTH: 20
<212> TYPE: DNA
<213> ORGANISM: Homo sapiens

<400> SEQUENCE: 174
acctagacca ccacttaacc                                           20

<210> SEQ ID NO 175
<211> LENGTH: 20
<212> TYPE: DNA
<213> ORGANISM: Homo sapiens

<400> SEQUENCE: 175
cctagaccac cacttaaccg                                           20

<210> SEQ ID NO 176
<211> LENGTH: 20
<212> TYPE: DNA
<213> ORGANISM: Homo sapiens

<400> SEQUENCE: 176
ctagaccacc acttaaccga                                           20

<210> SEQ ID NO 177
<211> LENGTH: 20
<212> TYPE: DNA
<213> ORGANISM: Homo sapiens

<400> SEQUENCE: 177
tggttatcgt gtaactaaaa                                           20

<210> SEQ ID NO 178
<211> LENGTH: 20
<212> TYPE: DNA
<213> ORGANISM: Homo sapiens

<400> SEQUENCE: 178
ggttatcgtg taactaaaaa                                           20

<210> SEQ ID NO 179
<211> LENGTH: 20
<212> TYPE: DNA
<213> ORGANISM: Homo sapiens

<400> SEQUENCE: 179
gttatcgtgt aactaaaaac                                           20

<210> SEQ ID NO 180
<211> LENGTH: 20
<212> TYPE: DNA
<213> ORGANISM: Homo sapiens

<400> SEQUENCE: 180
gtattctaca ctccagggac                                           20

<210> SEQ ID NO 181
<211> LENGTH: 20
<212> TYPE: DNA
<213> ORGANISM: Homo sapiens

<400> SEQUENCE: 181
tattctacac tccagggacc                                           20

<210> SEQ ID NO 182
<211> LENGTH: 20
<212> TYPE: DNA
<213> ORGANISM: Homo sapiens

<400> SEQUENCE: 182
attctacact ccagggacca                                           20

<210> SEQ ID NO 183
<211> LENGTH: 20
<212> TYPE: DNA
<213> ORGANISM: Homo sapiens

<400> SEQUENCE: 183
ttctacactc cagggaccac                                           20

<210> SEQ ID NO 184
<211> LENGTH: 20
<212> TYPE: DNA
<213> ORGANISM: Homo sapiens

<400> SEQUENCE: 184
tctacactcc agggaccacc                                           20

<210> SEQ ID NO 185
<211> LENGTH: 20
<212> TYPE: DNA
<213> ORGANISM: Homo sapiens

<400> SEQUENCE: 185
ctacactcca gggaccacct                                           20

<210> SEQ ID NO 186
<211> LENGTH: 20
<212> TYPE: DNA
<213> ORGANISM: Homo sapiens

```
<400> SEQUENCE: 186
tacactccag ggaccacctg                                               20

<210> SEQ ID NO 187
<211> LENGTH: 20
<212> TYPE: DNA
<213> ORGANISM: Homo sapiens

<400> SEQUENCE: 187
acactccagg gaccacctgg                                               20

<210> SEQ ID NO 188
<211> LENGTH: 20
<212> TYPE: DNA
<213> ORGANISM: Homo sapiens

<400> SEQUENCE: 188
cactccaggg accacctggt                                               20

<210> SEQ ID NO 189
<211> LENGTH: 20
<212> TYPE: DNA
<213> ORGANISM: Homo sapiens

<400> SEQUENCE: 189
actccaggga ccacctggta                                               20

<210> SEQ ID NO 190
<211> LENGTH: 20
<212> TYPE: DNA
<213> ORGANISM: Homo sapiens

<400> SEQUENCE: 190
ctccagggac cacctggtac                                               20

<210> SEQ ID NO 191
<211> LENGTH: 20
<212> TYPE: DNA
<213> ORGANISM: Homo sapiens

<400> SEQUENCE: 191
tccagggacc acctggtact                                               20

<210> SEQ ID NO 192
<211> LENGTH: 20
<212> TYPE: DNA
<213> ORGANISM: Homo sapiens

<400> SEQUENCE: 192
ccagggacca cctggtactg                                               20

<210> SEQ ID NO 193
<211> LENGTH: 20
<212> TYPE: DNA
<213> ORGANISM: Homo sapiens

<400> SEQUENCE: 193
cagggaccac ctggtactgg                                               20

<210> SEQ ID NO 194
<211> LENGTH: 20
<212> TYPE: DNA
<213> ORGANISM: Homo sapiens
```

```
<400> SEQUENCE: 194
agggaccacc tggtactggt                                              20

<210> SEQ ID NO 195
<211> LENGTH: 20
<212> TYPE: DNA
<213> ORGANISM: Homo sapiens

<400> SEQUENCE: 195
gggaccacct ggtactggta                                              20

<210> SEQ ID NO 196
<211> LENGTH: 20
<212> TYPE: DNA
<213> ORGANISM: Homo sapiens

<400> SEQUENCE: 196
ggaccacctg gtactggtaa                                              20

<210> SEQ ID NO 197
<211> LENGTH: 20
<212> TYPE: DNA
<213> ORGANISM: Homo sapiens

<400> SEQUENCE: 197
gaccacctgg tactggtaag                                              20

<210> SEQ ID NO 198
<211> LENGTH: 20
<212> TYPE: DNA
<213> ORGANISM: Homo sapiens

<400> SEQUENCE: 198
accacctggt actggtaaga                                              20

<210> SEQ ID NO 199
<211> LENGTH: 20
<212> TYPE: DNA
<213> ORGANISM: Homo sapiens

<400> SEQUENCE: 199
ccacctggta ctggtaagag                                              20

<210> SEQ ID NO 200
<211> LENGTH: 20
<212> TYPE: DNA
<213> ORGANISM: Homo sapiens

<400> SEQUENCE: 200
cacctggtac tggtaagagt                                              20

<210> SEQ ID NO 201
<211> LENGTH: 20
<212> TYPE: DNA
<213> ORGANISM: Homo sapiens

<400> SEQUENCE: 201
acctggtact ggtaagagtc                                              20

<210> SEQ ID NO 202
<211> LENGTH: 20
<212> TYPE: DNA
```

-continued

<213> ORGANISM: Homo sapiens

<400> SEQUENCE: 202
cctggtactg gtaagagtca                                           20

<210> SEQ ID NO 203
<211> LENGTH: 20
<212> TYPE: DNA
<213> ORGANISM: Homo sapiens

<400> SEQUENCE: 203
gggactacca actcaaactg                                           20

<210> SEQ ID NO 204
<211> LENGTH: 20
<212> TYPE: DNA
<213> ORGANISM: Homo sapiens

<400> SEQUENCE: 204
acctacacac ctcagtgttg                                           20

<210> SEQ ID NO 205
<211> LENGTH: 20
<212> TYPE: DNA
<213> ORGANISM: Homo sapiens

<400> SEQUENCE: 205
cttcgatgtc gagggtgtc                                            20

<210> SEQ ID NO 206
<211> LENGTH: 20
<212> TYPE: DNA
<213> ORGANISM: Homo sapiens

<400> SEQUENCE: 206
ttcgatgtcg agggtgtca                                            20

<210> SEQ ID NO 207
<211> LENGTH: 20
<212> TYPE: DNA
<213> ORGANISM: Homo sapiens

<400> SEQUENCE: 207
tcgatgtcga ggggtgtcat                                           20

<210> SEQ ID NO 208
<211> LENGTH: 20
<212> TYPE: DNA
<213> ORGANISM: Homo sapiens

<400> SEQUENCE: 208
cgatgtcgag gggtgtcatg                                           20

<210> SEQ ID NO 209
<211> LENGTH: 20
<212> TYPE: DNA
<213> ORGANISM: Homo sapiens

<400> SEQUENCE: 209
gtagaaaggt tcaacacatg                                           20

<210> SEQ ID NO 210
<211> LENGTH: 20

```
<212> TYPE: DNA
<213> ORGANISM: Homo sapiens

<400> SEQUENCE: 210
tagaaaggtt caacacatgg                                              20

<210> SEQ ID NO 211
<211> LENGTH: 20
<212> TYPE: DNA
<213> ORGANISM: Homo sapiens

<400> SEQUENCE: 211
agaaaggttc aacacatggt                                              20

<210> SEQ ID NO 212
<211> LENGTH: 20
<212> TYPE: DNA
<213> ORGANISM: Homo sapiens

<400> SEQUENCE: 212
cccagttctt cacgacattg                                              20

<210> SEQ ID NO 213
<211> LENGTH: 20
<212> TYPE: DNA
<213> ORGANISM: Homo sapiens

<400> SEQUENCE: 213
cttcacgaca ttggtaaccc                                              20

<210> SEQ ID NO 214
<211> LENGTH: 20
<212> TYPE: DNA
<213> ORGANISM: Homo sapiens

<400> SEQUENCE: 214
ctctgacagt ccatgtgagt                                              20

<210> SEQ ID NO 215
<211> LENGTH: 20
<212> TYPE: DNA
<213> ORGANISM: Homo sapiens

<400> SEQUENCE: 215
tctgacagtc catgtgagtc                                              20

<210> SEQ ID NO 216
<211> LENGTH: 20
<212> TYPE: DNA
<213> ORGANISM: Homo sapiens

<400> SEQUENCE: 216
ctgacagtcc atgtgagtct                                              20

<210> SEQ ID NO 217
<211> LENGTH: 20
<212> TYPE: DNA
<213> ORGANISM: Homo sapiens

<400> SEQUENCE: 217
tgacagtcca tgtgagtctc                                              20

<210> SEQ ID NO 218
```

```
<211> LENGTH: 20
<212> TYPE: DNA
<213> ORGANISM: Homo sapiens

<400> SEQUENCE: 218
gacagtccat gtgagtctca                                               20

<210> SEQ ID NO 219
<211> LENGTH: 20
<212> TYPE: DNA
<213> ORGANISM: Homo sapiens

<400> SEQUENCE: 219
cagtccatgt gagtctcatg                                               20

<210> SEQ ID NO 220
<211> LENGTH: 20
<212> TYPE: DNA
<213> ORGANISM: Homo sapiens

<400> SEQUENCE: 220
agtccatgtg agtctcatgg                                               20

<210> SEQ ID NO 221
<211> LENGTH: 20
<212> TYPE: DNA
<213> ORGANISM: Homo sapiens

<400> SEQUENCE: 221
gtccatgtga gtctcatgga                                               20

<210> SEQ ID NO 222
<211> LENGTH: 20
<212> TYPE: DNA
<213> ORGANISM: Homo sapiens

<400> SEQUENCE: 222
gggacacttt gatggacaac                                               20

<210> SEQ ID NO 223
<211> LENGTH: 20
<212> TYPE: DNA
<213> ORGANISM: Homo sapiens

<400> SEQUENCE: 223
cactttgatg gacaacaggg                                               20

<210> SEQ ID NO 224
<211> LENGTH: 20
<212> TYPE: DNA
<213> ORGANISM: Homo sapiens

<400> SEQUENCE: 224
ctttgatgga caacagggtg                                               20

<210> SEQ ID NO 225
<211> LENGTH: 20
<212> TYPE: DNA
<213> ORGANISM: Homo sapiens

<400> SEQUENCE: 225
tgatggacaa cagggtgaag                                               20
```

```
<210> SEQ ID NO 226
<211> LENGTH: 20
<212> TYPE: DNA
<213> ORGANISM: Homo sapiens

<400> SEQUENCE: 226
gatggacaac agggtgaagt                                                 20

<210> SEQ ID NO 227
<211> LENGTH: 20
<212> TYPE: DNA
<213> ORGANISM: Homo sapiens

<400> SEQUENCE: 227
tggacaacag ggtgaagtac                                                 20

<210> SEQ ID NO 228
<211> LENGTH: 20
<212> TYPE: DNA
<213> ORGANISM: Homo sapiens

<400> SEQUENCE: 228
ggacaacagg gtgaagtacc                                                 20

<210> SEQ ID NO 229
<211> LENGTH: 20
<212> TYPE: DNA
<213> ORGANISM: Homo sapiens

<400> SEQUENCE: 229
accagaactc aattaccccc                                                 20

<210> SEQ ID NO 230
<211> LENGTH: 20
<212> TYPE: DNA
<213> ORGANISM: Homo sapiens

<400> SEQUENCE: 230
ccagaactca attacccccT                                                 20

<210> SEQ ID NO 231
<211> LENGTH: 20
<212> TYPE: DNA
<213> ORGANISM: Homo sapiens

<400> SEQUENCE: 231
cagaactcaa ttaccccctg                                                 20

<210> SEQ ID NO 232
<211> LENGTH: 20
<212> TYPE: DNA
<213> ORGANISM: Homo sapiens

<400> SEQUENCE: 232
ctatacatgt ctctgggacc                                                 20

<210> SEQ ID NO 233
<211> LENGTH: 20
<212> TYPE: DNA
<213> ORGANISM: Homo sapiens

<400> SEQUENCE: 233
cctggtgatt cttcttcagg                                                 20
```

```
<210> SEQ ID NO 234
<211> LENGTH: 20
<212> TYPE: DNA
<213> ORGANISM: Homo sapiens

<400> SEQUENCE: 234
cacttgaccc tctctcagaa                                               20

<210> SEQ ID NO 235
<211> LENGTH: 20
<212> TYPE: DNA
<213> ORGANISM: Homo sapiens

<400> SEQUENCE: 235
cttgaccctc tctcagaaac                                               20

<210> SEQ ID NO 236
<211> LENGTH: 20
<212> TYPE: DNA
<213> ORGANISM: Homo sapiens

<400> SEQUENCE: 236
ttgaccctct ctcagaaaca                                               20

<210> SEQ ID NO 237
<211> LENGTH: 20
<212> TYPE: DNA
<213> ORGANISM: Homo sapiens

<400> SEQUENCE: 237
tgaccctctc tcagaaacaa                                               20

<210> SEQ ID NO 238
<211> LENGTH: 20
<212> TYPE: DNA
<213> ORGANISM: Homo sapiens

<400> SEQUENCE: 238
gaccctctct cagaaacaaa                                               20

<210> SEQ ID NO 239
<211> LENGTH: 20
<212> TYPE: DNA
<213> ORGANISM: Homo sapiens

<400> SEQUENCE: 239
tccgtgatcc acagacactt                                               20

<210> SEQ ID NO 240
<211> LENGTH: 20
<212> TYPE: DNA
<213> ORGANISM: Homo sapiens

<400> SEQUENCE: 240
ccgtgatcca cagacacttg                                               20

<210> SEQ ID NO 241
<211> LENGTH: 20
<212> TYPE: DNA
<213> ORGANISM: Homo sapiens

<400> SEQUENCE: 241
cgtgatccac agacacttga                                               20
```

```
<210> SEQ ID NO 242
<211> LENGTH: 20
<212> TYPE: DNA
<213> ORGANISM: Homo sapiens

<400> SEQUENCE: 242
gtgatccaca gacacttgag                                              20

<210> SEQ ID NO 243
<211> LENGTH: 20
<212> TYPE: DNA
<213> ORGANISM: Homo sapiens

<400> SEQUENCE: 243
gagattcttg acattacacc                                              20

<210> SEQ ID NO 244
<211> LENGTH: 20
<212> TYPE: DNA
<213> ORGANISM: Homo sapiens

<400> SEQUENCE: 244
cagatcaact tactcctact                                              20

<210> SEQ ID NO 245
<211> LENGTH: 20
<212> TYPE: DNA
<213> ORGANISM: Homo sapiens

<400> SEQUENCE: 245
gatcaactta ctcctacttg                                              20

<210> SEQ ID NO 246
<211> LENGTH: 20
<212> TYPE: DNA
<213> ORGANISM: Homo sapiens

<400> SEQUENCE: 246
atcaacttac tcctacttgg                                              20

<210> SEQ ID NO 247
<211> LENGTH: 20
<212> TYPE: DNA
<213> ORGANISM: Homo sapiens

<400> SEQUENCE: 247
ctcagactaa ttctcctcgg                                              20

<210> SEQ ID NO 248
<211> LENGTH: 20
<212> TYPE: DNA
<213> ORGANISM: Homo sapiens

<400> SEQUENCE: 248
ccagtgtcta tgaccaagac                                              20

<210> SEQ ID NO 249
<211> LENGTH: 20
<212> TYPE: DNA
<213> ORGANISM: Homo sapiens

<400> SEQUENCE: 249
```
ttaccagatc catcaaaacc                                           20

<210> SEQ ID NO 250
<211> LENGTH: 20
<212> TYPE: DNA
<213> ORGANISM: Homo sapiens

<400> SEQUENCE: 250
taccagatcc atcaaaacca                                           20

<210> SEQ ID NO 251
<211> LENGTH: 20
<212> TYPE: DNA
<213> ORGANISM: Homo sapiens

<400> SEQUENCE: 251
accagatcca tcaaaaccaa                                           20

<210> SEQ ID NO 252
<211> LENGTH: 20
<212> TYPE: DNA
<213> ORGANISM: Homo sapiens

<400> SEQUENCE: 252
ccagatccat caaaaccaag                                           20

<210> SEQ ID NO 253
<211> LENGTH: 20
<212> TYPE: DNA
<213> ORGANISM: Homo sapiens

<400> SEQUENCE: 253
cttatgtcct tccctcagtc                                           20

<210> SEQ ID NO 254
<211> LENGTH: 20
<212> TYPE: DNA
<213> ORGANISM: Homo sapiens

<400> SEQUENCE: 254
tatgaaccac aaatcattac                                           20

<210> SEQ ID NO 255
<211> LENGTH: 20
<212> TYPE: DNA
<213> ORGANISM: Homo sapiens

<400> SEQUENCE: 255
atgaaccaca aatcattact                                           20

<210> SEQ ID NO 256
<211> LENGTH: 20
<212> TYPE: DNA
<213> ORGANISM: Homo sapiens

<400> SEQUENCE: 256
tgaaccacaa atcattacta                                           20

<210> SEQ ID NO 257
<211> LENGTH: 20
<212> TYPE: DNA
<213> ORGANISM: Homo sapiens

<400> SEQUENCE: 257

```
gaaccacaaa tcattactac                                              20

<210> SEQ ID NO 258
<211> LENGTH: 20
<212> TYPE: DNA
<213> ORGANISM: Homo sapiens

<400> SEQUENCE: 258
aaccacaaat cattactaca                                              20

<210> SEQ ID NO 259
<211> LENGTH: 20
<212> TYPE: DNA
<213> ORGANISM: Homo sapiens

<400> SEQUENCE: 259
cctcactccc tttcggatgg                                              20

<210> SEQ ID NO 260
<211> LENGTH: 20
<212> TYPE: DNA
<213> ORGANISM: Homo sapiens

<400> SEQUENCE: 260
ctgtgatcct tcgtggacat                                              20

<210> SEQ ID NO 261
<211> LENGTH: 20
<212> TYPE: DNA
<213> ORGANISM: Homo sapiens

<400> SEQUENCE: 261
gttcaagaac tttactctcc                                              20

<210> SEQ ID NO 262
<211> LENGTH: 20
<212> TYPE: DNA
<213> ORGANISM: Homo sapiens

<400> SEQUENCE: 262
aagaacttta ctctccaatt                                              20

<210> SEQ ID NO 263
<211> LENGTH: 20
<212> TYPE: DNA
<213> ORGANISM: Homo sapiens

<400> SEQUENCE: 263
agaactttac tctccaattt                                              20

<210> SEQ ID NO 264
<211> LENGTH: 20
<212> TYPE: DNA
<213> ORGANISM: Homo sapiens

<400> SEQUENCE: 264
gaactttact ctccaatttt                                              20

<210> SEQ ID NO 265
<211> LENGTH: 20
<212> TYPE: DNA
<213> ORGANISM: Homo sapiens
```

```
<400> SEQUENCE: 265
gaccttaaat tccctcgagg                                              20

<210> SEQ ID NO 266
<211> LENGTH: 20
<212> TYPE: DNA
<213> ORGANISM: Homo sapiens

<400> SEQUENCE: 266
ccttaaattc cctcgaggac                                              20

<210> SEQ ID NO 267
<211> LENGTH: 20
<212> TYPE: DNA
<213> ORGANISM: Homo sapiens

<400> SEQUENCE: 267
aaattccctc gaggacaagg                                              20

<210> SEQ ID NO 268
<211> LENGTH: 20
<212> TYPE: DNA
<213> ORGANISM: Homo sapiens

<400> SEQUENCE: 268
agacgaattc gtggtggtga                                              20

<210> SEQ ID NO 269
<211> LENGTH: 20
<212> TYPE: DNA
<213> ORGANISM: Homo sapiens

<400> SEQUENCE: 269
cagacgtggt ccagaacaaa                                              20

<210> SEQ ID NO 270
<211> LENGTH: 20
<212> TYPE: DNA
<213> ORGANISM: Homo sapiens

<400> SEQUENCE: 270
agacgtggtc cagaacaaac                                              20

<210> SEQ ID NO 271
<211> LENGTH: 20
<212> TYPE: DNA
<213> ORGANISM: Homo sapiens

<400> SEQUENCE: 271
gacgtggtcc agaacaaacc                                              20

<210> SEQ ID NO 272
<211> LENGTH: 20
<212> TYPE: DNA
<213> ORGANISM: Homo sapiens

<400> SEQUENCE: 272
acgtggtcca gaacaaaccc                                              20

<210> SEQ ID NO 273
<211> LENGTH: 20
<212> TYPE: DNA
<213> ORGANISM: Homo sapiens
```

```
<400> SEQUENCE: 273
cgtggtccag aacaaaccca                                              20

<210> SEQ ID NO 274
<211> LENGTH: 20
<212> TYPE: DNA
<213> ORGANISM: Homo sapiens

<400> SEQUENCE: 274
gtggtccaga acaaacccaa                                              20

<210> SEQ ID NO 275
<211> LENGTH: 20
<212> TYPE: DNA
<213> ORGANISM: Homo sapiens

<400> SEQUENCE: 275
tggtccagaa caaacccaag                                              20

<210> SEQ ID NO 276
<211> LENGTH: 20
<212> TYPE: DNA
<213> ORGANISM: Homo sapiens

<400> SEQUENCE: 276
ggtccagaac aaacccaagg                                              20

<210> SEQ ID NO 277
<211> LENGTH: 20
<212> TYPE: DNA
<213> ORGANISM: Homo sapiens

<400> SEQUENCE: 277
gtccagaaca aacccaagga                                              20

<210> SEQ ID NO 278
<211> LENGTH: 20
<212> TYPE: DNA
<213> ORGANISM: Homo sapiens

<400> SEQUENCE: 278
ggaaattttg gggaccagga                                              20

<210> SEQ ID NO 279
<211> LENGTH: 20
<212> TYPE: DNA
<213> ORGANISM: Homo sapiens

<400> SEQUENCE: 279
agtcacacct tcgggaacgt                                              20

<210> SEQ ID NO 280
<211> LENGTH: 20
<212> TYPE: DNA
<213> ORGANISM: Homo sapiens

<400> SEQUENCE: 280
tcacaccttc gggaacgtgg                                              20

<210> SEQ ID NO 281
<211> LENGTH: 20
<212> TYPE: DNA
```

```
<213> ORGANISM: Homo sapiens

<400> SEQUENCE: 281
cacaccttcg ggaacgtggt                                               20

<210> SEQ ID NO 282
<211> LENGTH: 20
<212> TYPE: DNA
<213> ORGANISM: Homo sapiens

<400> SEQUENCE: 282
caccttcggg aacgtggttg                                               20

<210> SEQ ID NO 283
<211> LENGTH: 20
<212> TYPE: DNA
<213> ORGANISM: Homo sapiens

<400> SEQUENCE: 283
ttcgggaacg tggttgacct                                               20

<210> SEQ ID NO 284
<211> LENGTH: 20
<212> TYPE: DNA
<213> ORGANISM: Homo sapiens

<400> SEQUENCE: 284
tcgggaacgt ggttgaccta                                               20

<210> SEQ ID NO 285
<211> LENGTH: 20
<212> TYPE: DNA
<213> ORGANISM: Homo sapiens

<400> SEQUENCE: 285
cgggaacgtg gttgacctac                                               20

<210> SEQ ID NO 286
<211> LENGTH: 20
<212> TYPE: DNA
<213> ORGANISM: Homo sapiens

<400> SEQUENCE: 286
gggaacgtgg ttgacctaca                                               20

<210> SEQ ID NO 287
<211> LENGTH: 20
<212> TYPE: DNA
<213> ORGANISM: Homo sapiens

<400> SEQUENCE: 287
ggaacgtggt tgacctacac                                               20

<210> SEQ ID NO 288
<211> LENGTH: 20
<212> TYPE: DNA
<213> ORGANISM: Homo sapiens

<400> SEQUENCE: 288
gaacgtggtt gacctacaca                                               20

<210> SEQ ID NO 289
<211> LENGTH: 20
```

```
<212> TYPE: DNA
<213> ORGANISM: Homo sapiens

<400> SEQUENCE: 289
aacgtggttg acctacacag                                                  20

<210> SEQ ID NO 290
<211> LENGTH: 20
<212> TYPE: DNA
<213> ORGANISM: Homo sapiens

<400> SEQUENCE: 290
acgtggttga cctacacagg                                                  20

<210> SEQ ID NO 291
<211> LENGTH: 20
<212> TYPE: DNA
<213> ORGANISM: Homo sapiens

<400> SEQUENCE: 291
ccaccacatt ttcaccgagg                                                  20

<210> SEQ ID NO 292
<211> LENGTH: 20
<212> TYPE: DNA
<213> ORGANISM: Homo sapiens

<400> SEQUENCE: 292
ctattaagtg tgtacctcaa                                                  20

<210> SEQ ID NO 293
<211> LENGTH: 20
<212> TYPE: DNA
<213> ORGANISM: Homo sapiens

<400> SEQUENCE: 293
catactagga cctctttctg                                                  20
```